US012807669B2

(12) United States Patent
Weiss et al.

(10) Patent No.: US 12,807,669 B2
(45) Date of Patent: Nov. 24, 2026

(54) STABILIZATION OF PRANDIAL OR BASAL INSULIN ANALOGUES BY AN INTERNAL DISELENIDE BRIDGE

(71) Applicants: THE TRUSTEES OF INDIANA UNIVERSITY, Bloomington, IN (US); YISSUM RESEARCH AND DEVELOPMENT COMPANY OF THE HEBREW UNIVERSITY OF JERUSALEM LTD., Jerusalem (IL)

(72) Inventors: Michael A. Weiss, Indianapolis, IN (US); Norman Metanis, Maghar (IL); Orit Ktorza, Jerusalem (IL); Gil Shoham, Jerusalem (IL)

(73) Assignees: THE TRUSTEES OF INDIANA UNIVERSITY, Bloomington, IN (US); YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 1092 days.

(21) Appl. No.: 17/439,590

(22) PCT Filed: Apr. 17, 2020

(86) PCT No.: PCT/US2020/028770

§ 371 (c)(1),
(2) Date: Sep. 15, 2021

(87) PCT Pub. No.: WO2020/214955

PCT Pub. Date: Oct. 22, 2020

(65) Prior Publication Data

US 2022/0144915 A1 May 12, 2022

Related U.S. Application Data

(60) Provisional application No. 62/836,264, filed on Apr. 19, 2019.

(51) Int. Cl.

| | |
|---|---|
| ***A61K 38/28*** | (2006.01) |
| ***A61K 38/00*** | (2006.01) |
| ***A61P 3/08*** | (2006.01) |
| ***C07K 14/62*** | (2006.01) |

(52) U.S. Cl.
CPC .............. *C07K 14/62* (2013.01); *A61K 38/28* (2013.01)

(58) Field of Classification Search
CPC ........... A61K 38/00; A61K 38/28; A61P 3/08; C07K 14/62
See application file for complete search history.

(56) References Cited

U.S. PATENT DOCUMENTS

| | | | | |
|---|---|---|---|---|
| 8,748,570 | B2 * | 6/2014 | Robinson | C07K 1/107 556/136 |
| 8,946,148 | B2 * | 2/2015 | Miao | A61P 3/06 514/6.3 |
| 11,492,650 | B2 * | 11/2022 | Mandell | C07K 14/62 |
| 2005/0039235 | A1 | 2/2005 | Moloney et al. | |
| 2006/0217290 | A1 * | 9/2006 | Kohn | C07K 14/62 514/6.9 |
| 2015/0174209 | A1 * | 6/2015 | Chiquette | G16H 20/17 604/151 |
| 2015/0274802 | A1 | 10/2015 | Dimarchi et al. | |
| 2018/0118801 | A1 | 5/2018 | Delong et al. | |

FOREIGN PATENT DOCUMENTS

| | | | |
|---|---|---|---|
| CN | 103068842 | A | 4/2013 |
| CN | 104981251 | A | 10/2015 |
| WO | 2016172269 | A2 | 10/2016 |
| WO | 2018/045018 | A1 | 3/2018 |

OTHER PUBLICATIONS

Veronese et al., "PEGylation, successful approach to drug delivery," Drug Discovery Today, 2005, 10(21): 1451-1458. (Year: 2005).*
PCT International Search Report and Written Opinion completed Aug. 21, 2020 by the ISA/US and issued in connection with PCT/US2020/028770.
Arai et al. "Preparation of Selenoinsulin as a Long-Lasting Insulin Analogue" Angew Chem Int Ed Engl., 2017, vol. 129, pp. 5614-5618.
Extended European Search Report for counterpart EP patent application No. 20791191.8 dated Dec. 21, 2022.
Weil-Ktorza et al., "Substitution of an Internal Disulfide Bridge with a Diselenide Enhances both Foldability and Stability of Human Insulin", Chemistry—A European Journal, John Wiley & Sons, Inc, DE, vol. 25, No. 36, (May 16, 2019), pp. 8513-8521, XP071849593, ISSN: 0947-6539, DOI: 10.1002/CHEM.201900892.
Dhayalan et al., "Reassessment of an Innovative Insulin Analogue Excludes Protracted Action yet Highlights the Distinction between External and Internal Diselenide Bridges", Chemistry—A European Journal, John Wiley & Sons, Inc, DE, vol. 26, No. 21, (Mar. 18, 2020), pp. 4695-4700, XP071851216, ISSN: 0947-6539, DOI: 10.1002/CHEM.202000309.
Chi Quan, "Research on the Effect of Nitration on the Structure and Function of Insulin", China Doctoral Dissertation Full-text Database, Medical and Health Science and Technology, No. 2008, pp. 059-17.

(Continued)

*Primary Examiner* — Julie Ha
(74) *Attorney, Agent, or Firm* — Barnes & Thornburg LLP

(57) ABSTRACT

Disclosed herein are insulin analogues containing a pairwise substitution of cysteine at positions A6 and A11 with selenocysteine residues such that a diselenide bridge forms between these positions. The disleenide bridge of the [$Sec^{A6}$, $Sec^{A11}$] insulin analogues stabilizes the analogue relative to its [$Cys^{A6}$, $Cys^{A11}$] parent structure, providing formulations with extended shelf life at or above room temperature. Also provide are methods of treating diabetes mellitus using the [$Sec^{A6}$, $Sec^{A11}$] insulin analogue.

17 Claims, 28 Drawing Sheets

Specification includes a Sequence Listing.

(56) References Cited

OTHER PUBLICATIONS

Chinese Office Action for Application No. CN202080029534.0, dated Aug. 16, 2023.
Dr. Kenta Arai, "Preparation of Selenoinsulin as a Long-Lasting Insulin Analogue", Angewandte Chemie, vol. 56, No. 20, (2017), doi:10.1002/anie.201701654, pp. 5522-5526, XP055672085.
Office Action for copending Chinese patent application No. 202080029534.0, issued Sep. 26, 2024.

* cited by examiner pK$_a$ *ca.* 8.3
atomic radius S: 105 pm
$E_a$ = -220 mV pK$_a$ *ca.* 5.2
atomic radius Se: 120 pm
$E_a$ = -388 mV Amide and aromatic region of ¹H-NMR spectrum

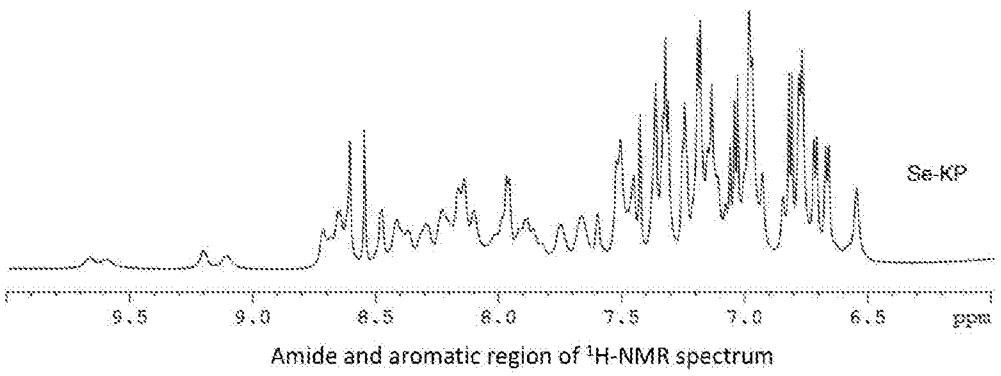
FIG. 12B
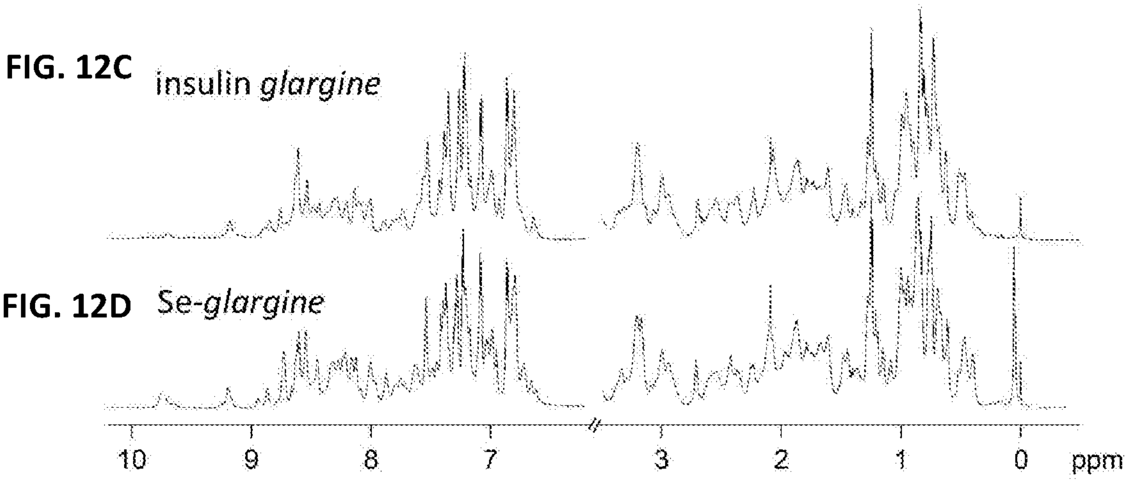
FIG. 12C
FIG. 12D

```
                              SEQUENCE LISTING


<160> NUMBER OF SEQ ID NOS: 54

<210> SEQ ID NO 1
<211> LENGTH: 86
<212> TYPE: PRT
<213> ORGANISM: Homo sapiens

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85


<210> SEQ ID NO 2
<211> LENGTH: 21
<212> TYPE: PRT
<213> ORGANISM: Homo sapiens

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20


<210> SEQ ID NO 3
<211> LENGTH: 21
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa at position 6 is selenocysteine
<220> FEATURE:
<221> NAME/KEY: MISC_FEATURE
<222> LOCATION: (8)..(8)
<223> OTHER INFORMATION: Xaa at position 8 is Thr, His, Lys, Arg or Trp
<220> FEATURE:
<221> NAME/KEY: MISC_FEATURE
<222> LOCATION: (8)..(8)
<223> OTHER INFORMATION: Xaa at position 8 is Thr, His, Lys, Arg or Trp
<220> FEATURE:
<221> NAME/KEY: MISC_FEATURE
```

<222> LOCATION: (11)..(11)
<223> OTHER INFORMATION: Xaa at position 11 is selenocysteine
<220> FEATURE:
<221> NAME/KEY: MISC_FEATURE
<222> LOCATION: (21)..(21)
<223> OTHER INFORMATION: Xaa at position 21 is Asn, Asp, Ala, Gly, Ser or Thr

<400> SEQUENCE: 3

Gly Ile Val Glu Gln Xaa Cys Xaa Ser Ile Xaa Ser Leu Tyr Gln Leu
1 5 10 15

Glu Asn Tyr Cys Xaa
20

<210> SEQ ID NO 4
<211> LENGTH: 30
<212> TYPE: PRT
<213> ORGANISM: Homo sapiens

<400> SEQUENCE: 4

Phe Val Asn Gln His Leu Cys Gly Ser His Leu Val Glu Ala Leu Tyr
1 5 10 15

Leu Val Cys Gly Glu Arg Gly Phe Phe Tyr Thr Pro Lys Thr
20 25 30

<210> SEQ ID NO 5
<211> LENGTH: 30
<212> TYPE: PRT
<213> ORGANISM: Homo sapiens

<400> SEQUENCE: 5

Phe Val Asn Gln His Leu Cys Gly Ser His Leu Val Glu Ala Leu Tyr
1 5 10 15

Leu Val Cys Gly Glu Arg Gly Phe Phe Tyr Thr Asp Lys Thr
20 25 30

<210> SEQ ID NO 6
<211> LENGTH: 30
<212> TYPE: PRT
<213> ORGANISM: Homo sapiens

<400> SEQUENCE: 6

Phe Val Asn Gln His Leu Cys Gly Ser His Leu Val Glu Ala Leu Tyr
1 5 10 15

Leu Val Cys Gly Glu Arg Gly Phe Phe Tyr Thr Lys Pro Thr
20 25 30

<210> SEQ ID NO 7
<211> LENGTH: 30
<212> TYPE: PRT
<213> ORGANISM: Homo sapiens

<400> SEQUENCE: 7

Phe Val Lys Gln His Leu Cys Gly Ser His Leu Val Glu Ala Leu Tyr
1 5 10 15

Leu Val Cys Gly Glu Arg Gly Phe Phe Tyr Thr Pro Glu Thr
20 25 30

<210> SEQ ID NO 8
<211> LENGTH: 32
<212> TYPE: PRT
<213> ORGANISM: Homo sapiens

<400> SEQUENCE: 8

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30


<210> SEQ ID NO 9
<211> LENGTH: 30
<212> TYPE: PRT
<213> ORGANISM: Homo sapiens
<220> FEATURE:
<221> NAME/KEY: MISC_FEATURE
<222> LOCATION: (29)..(29)
<223> OTHER INFORMATION: Xaa at position 29 is an acyl derivative of
      Lysine or glutamic-acid-bridged acyl derivative of Lysine
<220> FEATURE:
<221> NAME/KEY: MISC_FEATURE
<222> LOCATION: (30)..(30)
<223> OTHER INFORMATION: Xaa at position 30 is Thr, Ala, Ser or absent

<400> SEQUENCE: 9

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Xaa Xaa
            20                  25                  30


<210> SEQ ID NO 10
<211> LENGTH: 21
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa at position 4 is aspartic acid or glutamic
      acid
<220> FEATURE:
<221> NAME/KEY: MISC_FEATURE
<222> LOCATION: (5)..(5)
<223> OTHER INFORMATION: Xaa at position 5 is glutamine or glutamic acid
<220> FEATURE:
<221> NAME/KEY: MISC_FEATURE
<222> LOCATION: (6)..(6)
<223> OTHER INFORMATION: Xaa at position 6 is selenocysteine
<220> FEATURE:
<221> NAME/KEY: MISC_FEATURE
<222> LOCATION: (8)..(8)
<223> OTHER INFORMATION: Xaa at position 8 is histidine, threonine,
      lysine, arginine, tryptophan or phenylalanine
<220> FEATURE:
<221> NAME/KEY: MISC_FEATURE
<222> LOCATION: (9)..(9)
<223> OTHER INFORMATION: Xaa at position 9 is serine, arginine,
      ornithine, lysine or alanine
<220> FEATURE:
<221> NAME/KEY: MISC_FEATURE
<222> LOCATION: (10)..(10)
<223> OTHER INFORMATION: Xaa at position 10 is isoleucine or serine
<220> FEATURE:
<221> NAME/KEY: MISC_FEATURE
<222> LOCATION: (11)..(11)
<223> OTHER INFORMATION: Xaa at position 11 is selenocysteine
<220> FEATURE:
<221> NAME/KEY: MISC_FEATURE
<222> LOCATION: (12)..(12)
<223> OTHER INFORMATION: Xaa at position 12 is serine or aspartic acid
<220> FEATURE:
<221> NAME/KEY: MISC_FEATURE
<222> LOCATION: (14)..(14)
<223> OTHER INFORMATION: Xaa at position 14 is tyrosine, arginine,
      ornathine, lysine or alanine
<220> FEATURE:
<221> NAME/KEY: MISC_FEATURE
<222> LOCATION: (15)..(15)
<223> OTHER INFORMATION: Xaa at position 15 is glutamine, glutamic acid,
```

```
      arginine, ornithine, alanine, lysine or leucine
<220> FEATURE:
<221> NAME/KEY: MISC_FEATURE
<222> LOCATION: (17)..(17)
<223> OTHER INFORMATION: Xaa at position 17 is glutamic acid, aspartic
      acid, asparagine, lysine, ornithine or glutamine
<220> FEATURE:
<221> NAME/KEY: MISC_FEATURE
<222> LOCATION: (18)..(18)
<223> OTHER INFORMATION: Xaa at position 18 is methionine, asparagine,
      glutamine, glutamic acid, aspartic acid or threonine
<220> FEATURE:
<221> NAME/KEY: MISC_FEATURE
<222> LOCATION: (21)..(21)
<223> OTHER INFORMATION: Xaa at position 21 is alanine, glycine, serine,
      valine, threonine, isoleucine, leucine, glutamine, glutamic acid,
      asparagine, aspartic acid, histidine, tryptophan, tyrosine, or
      methionine

<400> SEQUENCE: 10

Gly Ile Val Xaa Xaa Xaa Cys Xaa Xaa Xaa Xaa Xaa Leu Xaa Xaa Leu
1               5                   10                  15

Xaa Xaa Tyr Cys Xaa
            20


<210> SEQ ID NO 11
<211> LENGTH: 21
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid
<220> FEATURE:
<221> NAME/KEY: MISC_FEATURE
<222> LOCATION: (9)..(9)
<223> OTHER INFORMATION: Xaa at position 9 is aspartic acid or glutamic
      acid
<220> FEATURE:
<221> NAME/KEY: MISC_FEATURE
<222> LOCATION: (10)..(10)
<223> OTHER INFORMATION: Xaa at position 10 is alanine or threonine
<220> FEATURE:
<221> NAME/KEY: MISC_FEATURE
<222> LOCATION: (17)..(17)
<223> OTHER INFORMATION: Xaa at position 17 is glutamic acid, aspartic
      acid or asparagine
<220> FEATURE:
<221> NAME/KEY: MISC_FEATURE
<222> LOCATION: (18)..(18)
<223> OTHER INFORMATION: Xaa at position 18 is alanine, ornithine,
      lysine or arginine
<220> FEATURE:
<221> NAME/KEY: MISC_FEATURE
<222> LOCATION: (21)..(21)
<223> OTHER INFORMATION: Xaa at position 21 is tyrosine or phenylalanine

<400> SEQUENCE: 11

Xaa Leu Cys Gly Xaa Xaa Leu Val Xaa Xaa Leu Tyr Leu Val Cys Gly
1               5                   10                  15

Xaa Xaa Gly Phe Xaa
            20


<210> SEQ ID NO 12
```

```
<211> LENGTH: 6
<212> TYPE: PRT
<213> ORGANISM: Homo sapiens

<400> SEQUENCE: 12

Ala Tyr Arg Pro Ser Glu
1               5


<210> SEQ ID NO 13
<211> LENGTH: 4
<212> TYPE: PRT
<213> ORGANISM: Homo sapiens

<400> SEQUENCE: 13

Phe Val Asn Gln
1


<210> SEQ ID NO 14
<211> LENGTH: 4
<212> TYPE: PRT
<213> ORGANISM: Homo sapiens

<400> SEQUENCE: 14

Pro Gly Pro Glu
1


<210> SEQ ID NO 15
<211> LENGTH: 21
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa at position 6 is selenocysteine
<220> FEATURE:
<221> NAME/KEY: MISC_FEATURE
<222> LOCATION: (8)..(8)
<223> OTHER INFORMATION: Xaa at position 8 is histidine, threonine,
      lysine, arginine, tryptophan or phenylalanine
<220> FEATURE:
<221> NAME/KEY: MISC_FEATURE
<222> LOCATION: (11)..(11)
<223> OTHER INFORMATION: Xaa at position 11 is selenocysteine
<220> FEATURE:
<221> NAME/KEY: MISC_FEATURE
<222> LOCATION: (21)..(21)
<223> OTHER INFORMATION: Xaa at position 21 is alanine, glycine, serine,
      threonine, glutamine, asparagine or aspartic acid

<400> SEQUENCE: 15

Gly Ile Val Glu Gln Xaa Cys Xaa Ser Ile Xaa Ser Leu Tyr Gln Leu
1               5                   10                  15

Glu Asn Tyr Cys Xaa
            20


<210> SEQ ID NO 16
<211> LENGTH: 30
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa at position 3 is asparagine or lysine
<220> FEATURE:
<221> NAME/KEY: MISC_FEATURE
<222> LOCATION: (5)..(5)
<223> OTHER INFORMATION: Xaa at position 5 is histidine or threonine
<220> FEATURE:
<221> NAME/KEY: MISC_FEATURE
<222> LOCATION: (28)..(28)
```

<223> OTHER INFORMATION: Xaa at position 28 is proline, lysine or aspartic acid
<220> FEATURE:
<221> NAME/KEY: MISC_FEATURE
<222> LOCATION: (29)..(29)
<223> OTHER INFORMATION: Xaa at position 29 is proline, lysine or glycine
<220> FEATURE:
<221> NAME/KEY: MISC_FEATURE
<222> LOCATION: (30)..(30)
<223> OTHER INFORMATION: Xaa at position 30 is threonine, alanine or serine

<400> SEQUENCE: 16

```
Phe Val Xaa Gln Xaa Leu Cys Gly Ser His Leu Val Glu Ala Leu Tyr
1               5                   10                  15

Leu Val Cys Gly Glu Arg Gly Phe Phe Tyr Thr Xaa Xaa Xaa
            20                  25                  30
```

<210> SEQ ID NO 17
<211> LENGTH: 21
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa at position 6 is selenocysteine
<220> FEATURE:
<221> NAME/KEY: MISC_FEATURE
<222> LOCATION: (8)..(8)
<223> OTHER INFORMATION: Xaa at position 8 is histidine or threonine
<220> FEATURE:
<221> NAME/KEY: MISC_FEATURE
<222> LOCATION: (9)..(9)
<223> OTHER INFORMATION: Xaa at position 9 is serine, lysine, or alanine
<220> FEATURE:
<221> NAME/KEY: MISC_FEATURE
<222> LOCATION: (11)..(11)
<223> OTHER INFORMATION: Xaa at position 11 is selenocysteine
<220> FEATURE:
<221> NAME/KEY: MISC_FEATURE
<222> LOCATION: (21)..(21)
<223> OTHER INFORMATION: Xaa at position 21 is alanine, glycine or asparagine

<400> SEQUENCE: 17

```
Gly Ile Val Glu Gln Xaa Cys Xaa Xaa Ile Xaa Ser Leu Tyr Gln Leu
1               5                   10                  15

Glu Asn Tyr Cys Xaa
            20
```

<210> SEQ ID NO 18
<211> LENGTH: 25
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa at position 3 is asparagine or lysine
<220> FEATURE:
<221> NAME/KEY: MISC_FEATURE
<222> LOCATION: (5)..(5)
<223> OTHER INFORMATION: Xaa at position 5 is histidine, arginine or threonine
<220> FEATURE:
<221> NAME/KEY: MISC_FEATURE
<222> LOCATION: (9)..(9)
<223> OTHER INFORMATION: Xaa at position 9 is alanine, glycine or serine
<220> FEATURE:
<221> NAME/KEY: MISC_FEATURE
<222> LOCATION: (10)..(10)
<223> OTHER INFORMATION: Xaa at position 10 is histidine, aspartic acid, glutamic acid, homocysteic acid or cysteic acid
<220> FEATURE:
<221> NAME/KEY: MISC_FEATURE
<222> LOCATION: (13)..(13)
<223> OTHER INFORMATION: Xaa at position 13 is aspartic acid or glutamic acid
<220> FEATURE:
<221> NAME/KEY: MISC_FEATURE
<222> LOCATION: (14)..(14)
<223> OTHER INFORMATION: Xaa at position 14 is alanine or threonine
<220> FEATURE:
<221> NAME/KEY: MISC_FEATURE
<222> LOCATION: (21)..(21)
<223> OTHER INFORMATION: Xaa at position 21 is glutamic acid, aspartic acid or asparagine
<220> FEATURE:
<221> NAME/KEY: MISC_FEATURE
<222> LOCATION: (22)..(22)
<223> OTHER INFORMATION: Xaa at position 22 is alanine, ornithine, lysine or arginine
<220> FEATURE:
<221> NAME/KEY: MISC_FEATURE
<222> LOCATION: (25)..(25)
<223> OTHER INFORMATION: Xaa at position 25 is tyrosine or phenylalanine

<400> SEQUENCE: 18

```
Phe Val Xaa Gln Xaa Leu Cys Gly Xaa Xaa Leu Val Xaa Xaa Leu Tyr
1               5                   10                  15

Leu Val Cys Gly Xaa Xaa Gly Phe Xaa
            20                  25
```

<210> SEQ ID NO 19
<211> LENGTH: 26
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: Xaa at position 12 is aspartic acid or glutamic acid
<220> FEATURE:
<221> NAME/KEY: MISC_FEATURE
<222> LOCATION: (20)..(20)
<223> OTHER INFORMATION: Xaa at position 20 is glutamic acid, aspartic acid or asparagine
<220> FEATURE:
<221> NAME/KEY: MISC_FEATURE
<222> LOCATION: (26)..(26)
<223> OTHER INFORMATION: Xaa at position 26 is tyrosine or phenylalanine

<400> SEQUENCE: 19

```
Gly Pro Glu Thr Leu Cys Gly Ala Glu Leu Val Xaa Ala Leu Tyr Leu
1               5                   10                  15

Val Cys Gly Xaa Arg Gly Phe Tyr Phe Xaa
            20                  25
```

<210> SEQ ID NO 20
<211> LENGTH: 25
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa at position 5 is histidine or threonine

<400> SEQUENCE: 20

```
Phe Val Asn Gln Xaa Leu Cys Gly Ser His Leu Val Glu Ala Leu Tyr
1               5                   10                  15

Leu Val Cys Gly Glu Arg Gly Phe Phe
            20                  25
```

<210> SEQ ID NO 21
<211> LENGTH: 25
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa at position 5 is histidine or threonine

<400> SEQUENCE: 21

Phe Val Lys Gln Xaa Leu Cys Gly Ser His Leu Val Glu Ala Leu Tyr
1               5                   10                  15

Leu Val Cys Gly Glu Arg Gly Phe Phe
            20                  25

<210> SEQ ID NO 22
<211> LENGTH: 5
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa at position 3 is proline, lysine, aspartic acid or glutamic acid

<400> SEQUENCE: 22

Tyr Thr Xaa Lys Thr
1               5

<210> SEQ ID NO 23
<211> LENGTH: 5
<212> TYPE: PRT
<213> ORGANISM: Homo sapiens

<400> SEQUENCE: 23

Tyr Thr Lys Pro Thr
1               5

<210> SEQ ID NO 24
<211> LENGTH: 4
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa at position 3 is alanine lysine, ornithine or arginine
<220> FEATURE:
<221> NAME/KEY: MISC_FEATURE
<222> LOCATION: (3)..(3)
<223> OTHER INFORMATION: Xaa at position 3 is proline, lysine, aspartic acid or glutamic acid

<400> SEQUENCE: 24

Tyr Thr Xaa Lys
1

<210> SEQ ID NO 25
<211> LENGTH: 4
<212> TYPE: PRT
<213> ORGANISM: Homo sapiens

<400> SEQUENCE: 25

Tyr Thr Pro Lys
1

<210> SEQ ID NO 26
<211> LENGTH: 30

```
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa at position 5 is histidine or threonine

<400> SEQUENCE: 26

Phe Val Asn Gln Xaa Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30


<210> SEQ ID NO 27
<211> LENGTH: 30
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa at position 5 is histidine or threonine

<400> SEQUENCE: 27

Phe Val Lys Gln Xaa Leu Cys Gly Ser His Leu Val Glu Ala Leu Tyr
1               5                   10                  15

Leu Val Cys Gly Glu Arg Gly Phe Phe Tyr Thr Glu Lys Thr
            20                  25                  30


<210> SEQ ID NO 28
<211> LENGTH: 30
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa at position 5 is histidine or threonine

<400> SEQUENCE: 28

Phe Val Asn Gln Xaa Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30


<210> SEQ ID NO 29
<211> LENGTH: 30
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa at position 5 is histidine or threonine

<400> SEQUENCE: 29

Phe Val Asn Gln Xaa Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30


<210> SEQ ID NO 30
<211> LENGTH: 21
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa at position 6 is selenocysteine
<220> FEATURE:
```

<221> NAME/KEY: MISC_FEATURE
<222> LOCATION: (11)..(11)
<223> OTHER INFORMATION: Xaa at position 11 is selenocysteine

<400> SEQUENCE: 30

```
Gly Ile Val Glu Gln Xaa Cys Thr Ser Ile Xaa Ser Leu Tyr Gln Leu
1               5                   10                  15

Glu Asn Tyr Cys Asn
            20
```

<210> SEQ ID NO 31
<211> LENGTH: 21
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa at position 6 is selenocysteine
<220> FEATURE:
<221> NAME/KEY: MISC_FEATURE
<222> LOCATION: (11)..(11)
<223> OTHER INFORMATION: Xaa at position 11 is selenocysteine

<400> SEQUENCE: 31

```
Gly Ile Val Asp Glu Xaa Cys Phe Arg Ser Xaa Asp Leu Arg Arg Leu
1               5                   10                  15

Glu Met Tyr Cys Ala
            20
```

<210> SEQ ID NO 32
<211> LENGTH: 29
<212> TYPE: PRT
<213> ORGANISM: Homo sapiens

<400> SEQUENCE: 32

```
Gly Pro Glu Thr Leu Cys Gly Ala Glu Leu Val Asp Ala Leu Tyr Leu
1               5                   10                  15

Val Cys Gly Asp Arg Gly Phe Tyr Phe Asn Lys Pro Thr
            20                  25
```

<210> SEQ ID NO 33
<211> LENGTH: 32
<212> TYPE: PRT
<213> ORGANISM: Homo sapiens

<400> SEQUENCE: 33

```
Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30
```

<210> SEQ ID NO 34
<211> LENGTH: 29
<212> TYPE: PRT
<213> ORGANISM: Homo sapiens

<400> SEQUENCE: 34

```
Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln Arg
            20                  25
```

<210> SEQ ID NO 35
<211> LENGTH: 29

```
<212> TYPE: PRT
<213> ORGANISM: Homo sapiens

<400> SEQUENCE: 35

Ser Ser Ser Ser Arg Ala Pro Pro Pro Ser Leu Pro Ser Pro Ser Arg
1               5                   10                  15

Leu Pro Gly Pro Ser Asp Thr Pro Ile Leu Pro Gln Arg
            20                  25


<210> SEQ ID NO 36
<211> LENGTH: 8
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa at position 7 is arginine, lysine or
      ornithine
<220> FEATURE:
<221> NAME/KEY: MISC_FEATURE
<222> LOCATION: (8)..(8)
<223> OTHER INFORMATION: Xaa at position 8 is arginine, lysine or
      ornithine

<400> SEQUENCE: 36

Gly Ala Gly Ser Ser Ser Xaa Xaa
1               5


<210> SEQ ID NO 37
<211> LENGTH: 8
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa at position 7 is arginine, lysine or
      ornithine
<220> FEATURE:
<221> NAME/KEY: MISC_FEATURE
<222> LOCATION: (8)..(8)
<223> OTHER INFORMATION: Xaa at position 8 is arginine, lysine or
      ornithine

<400> SEQUENCE: 37

Gly Tyr Gly Ser Ser Ser Xaa Xaa
1               5


<210> SEQ ID NO 38
<211> LENGTH: 12
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa at position 7 is arginine, lysine or
      ornithine
<220> FEATURE:
<221> NAME/KEY: MISC_FEATURE
<222> LOCATION: (8)..(8)
<223> OTHER INFORMATION: Xaa at position 8 is arginine, lysine or
      ornithine

<400> SEQUENCE: 38

Gly Tyr Gly Ser Ser Ser Xaa Xaa Ala Pro Gln Thr
1               5                   10


<210> SEQ ID NO 39
<211> LENGTH: 8
<212> TYPE: PRT
<213> ORGANISM: Homo sapiens
```

<400> SEQUENCE: 39

Gly Ala Gly Ser Ser Ser Arg Arg
1 5

<210> SEQ ID NO 40
<211> LENGTH: 8
<212> TYPE: PRT
<213> ORGANISM: Homo sapiens

<400> SEQUENCE: 40

Gly Tyr Gly Ser Ser Ser Arg Arg
1 5

<210> SEQ ID NO 41
<211> LENGTH: 70
<212> TYPE: PRT
<213> ORGANISM: Homo sapiens

<400> SEQUENCE: 41

Gly Pro Glu Thr Leu Cys Gly Ala Glu Leu Val Asp Ala Leu Gln Phe
1 5 10 15

Val Cys Gly Asp Arg Gly Phe Tyr Phe Asn Lys Pro Thr Gly Tyr Gly
20 25 30

Ser Ser Ser Arg Arg Ala Pro Gln Thr Gly Ile Val Asp Glu Cys Cys
35 40 45

Phe Arg Ser Cys Asp Leu Arg Arg Leu Glu Met Tyr Cys Ala Pro Leu
50 55 60

Lys Pro Ala Lys Ser Ala
65 70

<210> SEQ ID NO 42
<211> LENGTH: 67
<212> TYPE: PRT
<213> ORGANISM: Homo sapiens

<400> SEQUENCE: 42

Ala Tyr Arg Pro Ser Glu Thr Leu Cys Gly Gly Glu Leu Val Asp Thr
1 5 10 15

Leu Gln Phe Val Cys Gly Asp Arg Gly Phe Tyr Phe Ser Arg Pro Ala
20 25 30

Ser Arg Val Ser Arg Arg Ser Arg Gly Ile Val Glu Glu Cys Cys Phe
35 40 45

Arg Ser Cys Asp Leu Ala Leu Leu Glu Thr Tyr Cys Ala Thr Pro Ala
50 55 60

Lys Ser Glu
65

<210> SEQ ID NO 43
<211> LENGTH: 21
<212> TYPE: PRT
<213> ORGANISM: Homo sapiens

<400> SEQUENCE: 43

Gly Ile Val Asp Glu Cys Cys Phe Arg Ser Cys Asp Leu Arg Arg Leu
1 5 10 15

Glu Met Tyr Cys Ala
20

<210> SEQ ID NO 44

<211> LENGTH: 29
<212> TYPE: PRT
<213> ORGANISM: Homo sapiens

<400> SEQUENCE: 44

Gly Pro Glu Thr Leu Cys Gly Ala Glu Leu Val Asp Ala Leu Tyr Leu
1 5 10 15

Val Cys Gly Asp Arg Gly Phe Tyr Phe Asn Lys Pro Thr
20 25

<210> SEQ ID NO 45
<211> LENGTH: 21
<212> TYPE: PRT
<213> ORGANISM: Homo sapiens

<400> SEQUENCE: 45

Gly Ile Val Glu Glu Cys Cys Phe Arg Ser Cys Asp Leu Ala Leu Leu
1 5 10 15

Glu Thr Tyr Cys Ala
20

<210> SEQ ID NO 46
<211> LENGTH: 32
<212> TYPE: PRT
<213> ORGANISM: Homo sapiens

<400> SEQUENCE: 46

Ala Tyr Arg Pro Ser Glu Thr Leu Cys Gly Gly Glu Leu Val Asp Thr
1 5 10 15

Leu Gln Phe Val Cys Gly Asp Arg Gly Phe Tyr Phe Ser Arg Pro Ala
20 25 30

<210> SEQ ID NO 47
<211> LENGTH: 21
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa at position 6 is selenocysteine
<220> FEATURE:
<221> NAME/KEY: MISC_FEATURE
<222> LOCATION: (11)..(11)
<223> OTHER INFORMATION: Xaa at position 11 is selenocysteine
<220> FEATURE:
<221> NAME/KEY: MISC_FEATURE
<222> LOCATION: (14)..(14)
<223> OTHER INFORMATION: Xaa at position 14 is arginine or alanine
<220> FEATURE:
<221> NAME/KEY: MISC_FEATURE
<222> LOCATION: (15)..(15)
<223> OTHER INFORMATION: Xaa at position 11 is arginine or leucine
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: MISC_FEATURE
<222> LOCATION: (21)..(21)
<223> OTHER INFORMATION: Xaa at position 21 is alanine, glycine or
asparagine

<400> SEQUENCE: 47

Gly Ile Val Xaa Glu Xaa Cys Phe Arg Ser Xaa Asp Leu Xaa Xaa Leu
1 5 10 15

```
Glu Xaa Tyr Cys Xaa
            20


<210> SEQ ID NO 48
<211> LENGTH: 28
<212> TYPE: PRT
<213> ORGANISM: Homo sapiens
<220> FEATURE:
<221> NAME/KEY: MISC_FEATURE
<222> LOCATION: (15)..(15)
<223> OTHER INFORMATION: Xaa at position 15 is aspartic acid or glutamic
      acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 48

Ala Tyr Arg Pro Ser Glu Thr Leu Cys Gly Gly Glu Leu Val Xaa Thr
1               5                   10                  15

Leu Tyr Leu Val Cys Gly Xaa Arg Gly Phe Tyr Phe
            20                  25


<210> SEQ ID NO 49
<211> LENGTH: 4
<212> TYPE: PRT
<213> ORGANISM: Homo sapiens

<400> SEQUENCE: 49

Ser Arg Pro Ala
1


<210> SEQ ID NO 50
<211> LENGTH: 26
<212> TYPE: PRT
<213> ORGANISM: Homo sapiens

<400> SEQUENCE: 50

Phe Val Asn Gln His Leu Cys Gly Ser His Leu Val Glu Ala Leu Tyr
1               5                   10                  15

Leu Val Cys Gly Glu Arg Gly Phe Phe Tyr
            20                  25


<210> SEQ ID NO 51
<211> LENGTH: 26
<212> TYPE: PRT
<213> ORGANISM: Homo sapiens

<400> SEQUENCE: 51

Phe Val Asn Gln His Leu Cys Gly Ser His Leu Val Glu Ala Leu Tyr
1               5                   10                  15

Leu Val Cys Gly Glu Arg Gly Phe Phe Tyr
            20                  25


<210> SEQ ID NO 52
<211> LENGTH: 29
<212> TYPE: PRT
<213> ORGANISM: Homo sapiens

<400> SEQUENCE: 52

Gly Pro Glu Thr Leu Cys Gly Ala Glu Leu Val Asp Ala Leu Tyr Leu
1               5                   10                  15

Val Cys Gly Asp Arg Gly Phe Tyr Phe Asn Lys Pro Thr
            20                  25
```

-continued

```
<210> SEQ ID NO 53
<211> LENGTH: 32
<212> TYPE: PRT
<213> ORGANISM: Homo sapiens

<400> SEQUENCE: 53

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30


<210> SEQ ID NO 54
<211> LENGTH: 30
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 54

Phe Val Asn Gln Xaa Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

STABILIZATION OF PRANDIAL OR BASAL INSULIN ANALOGUES BY AN INTERNAL DISELENIDE BRIDGE

CROSS-REFERENCE TO RELATED APPLICATIONS

This application is a U.S. national counterpart application of international application serial No. PCT/US2020/028770 filed Apr. 17, 2020, which claims priority to U.S. Provisional Patent Application No. 62/836,264, filed Apr. 19, 2019, the disclosures of which are hereby expressly incorporated by reference in their entireties.

STATEMENT OF GOVERNMENT SUPPORT

This invention was made with government support under DK040949 and DK118536 awarded by National Institutes of Health. The government has certain rights in the invention.

INCORPORATION BY REFERENCE OF MATERIAL SUBMITTED ELECTRONICALLY

Incorporated by reference in its entirety is a computer-readable nucleotide/amino-acid sequence listing submitted concurrently herewith and identified as follows: 24 kilobytes ACII (text) file named "315514_ST25_ST25.txt," created on Jan. 8, 2025.

BACKGROUND

Insulin is a peptide hormone comprised of a two-chain heterodimer that is biosynthetically derived from a low-potency single-chain proinsulin precursor through enzymatic processing. Human insulin is comprised of two peptide chains (an "A chain" (SEQ ID NO: 2) and "B chain" (SEQ ID NO: 4)) bound together by disulfide bonds and having a total of 51 amino acids (aa). The A chain and B chain associate in a three-dimensional structure to assemble contact surfaces to enable high-affinity binding to the insulin receptor. These surfaces in part reorganize on receptor binding relative to the free hormone.

Insulin and its analogues demonstrate unparalleled ability to lower the concentration of glucose in the blood via cellular entry. An abnormal increase in blood-glucose concentration is a key issue in virtually all forms of diabetes mellitus (DM). Wild-type (WT) human insulin and other animal insulin molecules (as encoded in the genomes of other vertebrates) bind to insulin receptors (IRs) in multiple organs and diverse types of cells, irrespective of the receptor isoform generated by alternative modes of RNA splicing (designated isoform A or B; IR-A or IR-B) and further elaborated by patterns of post-translational glycosylation, which may be tissue-specific. The pharmacokinetic and pharmacodynamic (PK/PD) properties of WT human insulin and other animal insulins are often suboptimal in subsets of patients with DM. The associated unmet medical needs have led over the past three decades to the design, development and clinical use of insulin analogues (Sharma, A. K., et al., 2019). The two major classes of insulin analogue formulations are (i) those that are absorbed more rapidly from a subcutaneous depot (and so faster acting) than are regular human insulin formulations (Nørgaard, K., et al., 2018) and (ii) those that are absorbed less rapidly (and so slower acting and more prolonged) than are micro-crystalline suspensions of protamine-associated WT human insulin (Hompesch, M., et al. 2019). These classes are respectively designated as prandial analogue formulations or basal analogue formulations.

Unfortunately, prandial and basal insulin analogue formulations in current clinical use are typically more susceptible to chemical and physical degradation at or above room temperature than are formulations containing WT human insulin, especially rapid-acting insulin analogue formulations as used in insulin pumps (Woods, R. J., et al., 2012). Indeed, only one clinical insulin analogue formulation known in the art exhibits a shelf life stability greater than that of WT insulin (basal product Tresiba®; Novo-Nordisk). Accordingly, there is a continuing need for therapeutic insulin analogues that exhibit enhanced pharmaceutical properties, such as increased thermodynamic stability and augmented resistance to thermal fibrillation at or above room temperature.

It would therefore be of medical benefit to augment the thermodynamic stability of an insulin analogue (or any therapeutic protein) and particularly to mitigate its susceptibility to physical degradation (fibrillation). Administration of insulin in some form (an animal insulin, human insulin or human insulin analogue) has long been established as a treatment for DM. A major goal of conventional insulin replacement therapy in patients with DM is tight control of the blood-glucose concentration to prevent its excursion above or below the normal range characteristic of healthy human subjects. Excursions below the normal range are associated with immediate adrenergic or neuroglycopenic symptoms, which in severe episodes can lead to convulsions, coma, and death. Excursions above the normal range are associated with increased long-term risk of microvascular disease (including retinapathy, blindness and renal failure) and probably also the long-term risk macrovascular disease. Critical to the safe and convenient achievement of tight glycemic control by patients with Type 1 DM and by a subset of patients with Type 2 DM has been the development of novel insulin analogues that differ in sequence from naturally occurring mammalian insulins due to the presence of amino-acid substitutions or modified amino-acid side chains. Such substitutions and modifications have been introduced in the art to make canonical "regular" WT insulin formulations (soluble formulations of zinc-stabilized hexamers at neutral pH as known in the art) even more rapid and likewise to make canonical long-acting WT insulin formulations (typically microcrystalline suspensions) even longer acting. Despite their favorable PK/PD properties, such insulin analogue formulations may exhibit reduced thermodynamic stability and/or increased susceptibility to fibrillation, limiting shelf life at or above room temperature.

Insulin is a small globular protein that plays a central role in regulating the metabolism of vertebrates. Insulin is stored in the secretory granules of pancreatic β-cells as $Zn^{2+}$-stabilized hexamers, but functions as a $Zn^{2+}$-free monomer in the bloodstream. Insulin is the product of a single-chain precursor, proinsulin, in which a connecting region (35 residues) links the C-terminal residue of B chain (residue B30) to the N-terminal residue of the A chain (FIG. 1A, SEQ ID NO: 3). A variety of evidence indicates that the three-dimensional (3D) structure of proinsulin consists of an insulin-like core and disordered connecting peptide (FIG. 1B). Formation of three specific disulfide bridges (pairings A6-A11, A7-B7, and A20-B19; FIGS. 1A and 1B) is thought to be coupled to oxidative folding of proinsulin in the rough endoplasmic reticulum (ER). Proinsulin assembles to form soluble $Zn^{2+}$-coordinated hexamers shortly after export from the ER to the Golgi apparatus. Endoproteolytic digestion and conversion to insulin (FIG. 1C, SEQ ID NO: 19) occurs in immature secretory granules followed by morphological condensation. Crystalline arrays of zinc insulin hexamers within mature storage granules have been visualized in mouse islets by electron microscopy (EM).

The sequence of proinsulin (with component A and B domains) is shown in schematic form in FIG. 1A. Individual residues are indicated by the identity of the amino acid (typically using a standard three-letter code), the chain and sequence position (typically as a superscript). Pertinent to the present disclosure are the conserved cysteine residues at positions A6 and A11 ($Cys^{A6}$ and $Cys^{A11}$). These sulfur-containing side chains pair to form an internal disulfide bridge. The atoms of this bridge are not in contact with the insulin receptor (IR), as visualized in structures of insulin bound to fragments of the IR by X-ray crystallography and cryo-electron microscopic image reconstruction. Formation of the A6-A11 bridge (also designated cystine A6-A11) does, however, make a critical contribution to the packing of the hydrophobic core of insulin and to its thermodynamic stability.

The present disclosure is directed to insulin analogue formulations having (a) increased shelf life at or above room temperature and (b) in the case of prandial analogues, increased stability within the reservoir of an insulin pump. The latter is important to prevent pump occlusion and potential life-threatening diabetic ketoacidosis. Because WT human insulin formulations are ordinarily stabilized by zinc ions (which promote zinc-coordinated hexamer assembly), these needs are especially prominent in the context of amino-acid substitutions that are known in the art either to (i) reduce the stability of the zinc insulin hexamer (as exemplified by insulin lispro and insulin aspart; respectively the active components of Humalog® [Lilly] and Novolog® [Novo-Nordisk]), (ii) be used in zinc-free formulations (as exemplified by insulin glulisine, the active component of Apidra® [Sanofi]), (iii) be used in zinc-containing formulations at acidic pH wherein zinc ions do not bind to the protein and so do not promote protective hexamer assembly (as exemplified by insulin glargine, the active component of Lantus® and Toujeo® [Sanofi]). Restrictions regarding the storage and use of such products at or above room temperature have been imposed by the U.S. Food & Drug Administration as a result of these properties.

Previous efforts to mitigate the instability of insulin analogue formulations have employed conventional amino-acid substitutions on the surface of insulin, including introduction of one or more additional disulfide bridges spanning a surface not engaged in receptor binding. The utility of such surface substitutions or modifications has been confounded by unexpected and undesirable changes in receptor-binding properties or in signaling properties, such as increased mitogenicity leading to elevated risk of cancer on chronic administration of the insulin analogue (in the case of the stabilizing $Asp^{B10}$ substitution on the surface of the B chain) or aberrantly prolonged cellular signaling (in the case of an engineered disulfide bridge between residues B4 and A10). The utility of additional disulfide bridges has thus been confounded by unexpected and undesirable changes in biological properties, such as prolonged signaling once the IR is engaged, also creating concern for induction of cancer. Because of the evolutionary conservation of the core of insulin and its structural elegance, conventional amino-acid substitutions in the interior of insulin are generally associated with decreased themodynamic stability; to our knowledge, no such core substitution has been identified with enhanced stability.

The challenge of finding modifications that forestall fibrillation has been magnified by the lack of a consistent association between the free energy of unfolding ($\Delta G_u$) and the lag time prior to onset of fibrillation. The present invention exploits the distinctive physico-chemical properties of selenio-cysteine relative to cysteine (Sec versus Cys; FIG. 2A). Just as two Cys residues may pair to form a disulfide bridge (cystine), two Sec residues may pair to form a diselenide bridge (FIGS. 2B and 2C). A surprising aspect of the present disclosure is that pairwise substitution of the sulfur atoms in residues A6 and A11 in the interior of a rapid-acting insulin analogue or in the interior of a basal insulin analogue by selenium atoms should enhance stability and forestall fibrillation without change in receptor-binding affinity. The location of cystine A6-A11 is shown in FIG. 3; a mechanistic scheme describing the pathway of insulin fibrillation is shown in FIG. 4. The present disclosure thus views the chemistry of selenocysteine and selenocystine from a perspective unrelated to traditional views of oxidation-reduction chemistry as known in the art (Beld, J. et al. 2007, 2008, 2010).

The baseline instability of WT animal insulins and their intrinsic susceptibility to chemical and physical degradation in a pharmaceutical formulation has generally been mitigated through the inclusion of zinc ions, which promote the native assembly of $Zn^{2+}$-coordinated insulin hexamers. Such hexamers contain two axial zinc ions in their interior and exhibit greater stability than zinc-free insulin solutions. Zinc-containing insulin formulations generally exhibit shelf lives than corresponding formulations lacking zinc ions (Brange, J. (1987) in Galenics of Insulin, Springer, Berlin, Germany [https://doi.org/10.1007/978-3-662-02526-0_3]). The requirement for zinc ions is exacerbated by the amino-acid substitutions in certain insulin analogues in current clinical use (such as insulin lispro and insulin aspart) due to their lower thermodynamic stabilities and increased susceptibility to fibrillation. It would therefore be desirable to enhance the intrinsic stability of insulin analogues and their resistance to fibrillation such that pharmaceutical formulations could include excipients that could favorably enhance the speed or efficiency of insulin absorption from a subcutaneous depot but would compete with insulin for the binding of zinc ions. Examples of such excipients known in the art include triphosphate ions, trisulfate ions, and divalent-ion chelating agents, including ethylene-diamine-tetra-acetic acid (EDTA) and ethylene glycol-bis(O-aminoethyl ether)-N,N,N',N'-tetraacetic acid (EGTA).

It would be desirable, therefore, to provide a novel class of rapid-acting and long-acting insulin analogues whose monomeric structure is stabilized on a thermodynamic basis, such that global unfolding is minimized in the conformational folding equilibrium and such that subglobal conformational fluctuations are also damped. Enhanced stability and damped fluctuations are respectively associated with decreased rates of chemical degradation and physical degradation, together leading to an extended shelf life at or above room temperature. More generally, there is a need for a molecular design strategy to stabilize the insulin molecule without altering its receptor-binding surfaces.

Applicant has met that need by providing insulin analogues containing pairwise substitution of cysteines at position A6 and A11 by selenocysteine (Sec). The latter amino acid (which occurs naturally in the human body and is considered as the "$21^{st}$ encoded amino acid") contains a single atomic substitution: replacement of the sulfur atom in the side-chain thiol group by selenium. Pairs of Sec residues may form diselenide bridges, which are similar to disulfide bridges but with certain changes in physico-chemical properties. Pairwise Cys→Sec substitutions in a polypeptide may be favorable or unfavorable depending on the structural environment of the particular residues. The present application discloses that a specific diselenide bridge in a rapid-acting insulin analogue or a basal insulin analogue will be useful in enhancing their pharmacologic properties with respect to shelf life at or above room temperature, i.e., to mitigate the susceptibility of such protein formulations to chemical and physical degradation.

SUMMARY

In accordance with the present disclosure, insulin analogues are provided wherein a pairwise substitution of the cysteines at positions corresponding to A6 and A11 of native insulin have been replaced by selenocysteine. In one embodiment an analogue is a rapid-acting or long-acting insulin analogue that comprises a pairwise substitution of the cysteines at positions corresponding to A6 and A11 of native insulin. This pairwise substitution has been discovered to stabilize the 3D structure of the protein and/or delay the onset of fibrillation. The A6 and A11 positions in the A chain of mammalian insulins (and indeed in all vertebrate insulins, proinsulins and insulin-like growth factors, including IGF-I, IGF-II and relaxin family members) are conserved as cysteine. The two cysteines pair to form cystine A6-A11, one of three disulfide bridges in the vertebrate insulin superfamily. In 3D structures of the zinc-free insulin dimer and zinc insulin hexamers, the A6-A11 disulfide bridge packs within a cluster of aromatic and aliphatic side chains within the hydrophobic core of an individual monomer (FIG. 3). Although not wishing to be restricted by theory, gaps between side chains occur within this cluster such that atoms slightly larger than sulfur might be accommodated without nonlocal structural perturbations—and indeed a "sweet spot" of atomic radii might exist such that a slightly larger atom than sulfur would improve the efficiency of side-chain packing within this cluster.

As disclosed herein, pairwise substitution of the two sulfur atoms in cystine A6-A11 by selenium atoms stabilizes WT insulin and diverse insulin analogue molecules (Table 1); in the case of the three prandial insulin analogues in current clinical use (insulin lispro, insulin aspart and insulin glulisine) forestalls its fibrillation at or above room temperature (Table 2 and FIG. 11C, below). Because these paired modifications occur within the core of insulin (and not at its receptor-binding surfaces and not at its self-assembly surfaces), the analogues of the present disclosure are compatible with a broad range of conventional amino-acid modifications to the surface of an insulin monomer and with a broad range of non-peptidic surface modifications (such as acetylation or derivatization by carbohydrates, polyethylene glycol or phenyl-boronic acids) that are known in the art to alter the assembly, PK, PD or clearance properties of insulin analogue formulations.

In another embodiment a rapid-acting or long-acting insulin analogue is provided that contains a diselenide bridge between residues A6 and A11 that extends the shelf life of the active insulin receptor agonist in a pharmaceutical formulation for the treatment of diabetes mellitus. A further aspect of the present invention holds that the aforementioned pharmaceutical formulations may, in the case of rapid-acting formulations, not require inclusion of zinc ions (known in the art to enhance the stability of insulin analogues and promote its native self-assembly) and thereby enable inclusion of a broad range of excipients that would otherwise interact with or chelate zinc ions, including excipients intended to accelerate the absorption of insulin from a subcutaneous depot. It is yet another aspect of the present analogues that the A6 and A11 paired Sec substitutions provides a method to enhance the speed and fidelity of insulin chain combination (Kung, Y. T., et al., 1965; Katsoyannis, P. G., 1966), especially in the context of B-chain variants known to impair this reaction in combination with the WT A chain. A mechanistic scheme for insulin chain combination is shown in FIG. 5; its enhancement via pairwise substitutions $Cys^{A6}$→Sec and $Cys^{A11}$→Sec is depicted in FIG. 6.

In one embodiment an insulin analogue is provided wherein the insulin A chain comprises the sequence GIVEQ$X_6$C$X_8$SI$X_{11}$SLYQLENYC$X_{21}$-$R_{53}$ (SEQ ID NO: 15) and the insulin B chain comprises the sequence FV$X_{23}$Q$X_{25}$LCGSHLVEALYLVCGERGFFYT$X_{48}X_{49}X_{50}$ (SEQ ID NO: 16), wherein $X_6$ is selenocysteine;

$X_8$ is histidine, threonine, lysine, arginine, phenylalanine or tryptophan;

$X_{11}$ is selenocysteine; and $X_{21}$ is selected from the group consisting of alanine, glycine, serine, threonine, glutamine, asparagine, and aspartic acid;

$X_{23}$ is Asn or Lys:

$X_{25}$ is histidine or threonine;

$X_{48}$ is proline, lysine or aspartic acid;

$X_{49}$ is proline, lysine or glycine;

$X_{50}$ is threonine, alanine or serine; and $R_{53}$ is COOH or $CONH_2$.

In one embodiment an insulin analogue is provided wherein the A chain comprises the sequence of GIVEQ$X_6$CTSI$X_{11}$SLYQLENYCN (SEQ ID NO: 30) and the B chain comprises the sequence FVNQHLCGSHLVEALYLVCGERGFFYTPKT (SEQ ID NO: 4), wherein $X_6$ and $X_{11}$ are both selenocysteine.

In accordance with one embodiment the insulin analogue is a two-chain analogue wherein the A and B chains are joined to one another by disulfide (S—S) and/or diselenide (Se—Se) covalent bonds.

The solubility and retention times of the A6-A11 diselenide bridged insulin analogues disclosed herein can be modified by the attachment of hydrophilic moieties and/or long-chain hydrocarbons such as fatty acid chains. In one embodiment the A6-A11 diselenide bridged insulin analogues are modified by the covalent linkage of a hydrophilic moiety at one or more positions corresponding to A14, A15, B0, B1, B10, B22, B28, B29. In one embodiment the hydrophilic moiety is albumin, including for example, albumins such as human serum albumin (HSA) and recombinant human albumin (rHA). In one embodiment the hydrophilic moiety is a polyethylene glycol (PEG) chain, having a molecular weight selected from the range of about 500 to about 40,000 Daltons. In one embodiment the polyethylene glycol chain has a molecular weight selected from the range of about 500 to about 5,000 Daltons. In another embodiment the polyethylene glycol chain has a molecular weight of about 10,000 to about 20,000 Daltons.

Acylation or alkylation can increase the half-life of the insulin polypeptides in circulation. Acylation or alkylation can advantageously delay the onset of action and/or extend the duration of action at the insulin receptors. The insulin analogues may be acylated or alkylated at the same amino acid position where a hydrophilic moiety is linked. In one embodiment the acyl group or alkyl group is covalently linked to one or more positions selected from A14, A15, B0, B1, B10, B22, B28, B29 of the insulin peptide. The analogue can also be prepared as dimers or multimers comprising two or more of any of the A6-A11 diselenide bridged insulin analogues disclosed herein either as homodimers/homomultimers or as heterodimers/heteromultimers.

Also encompassed by the present disclosure are pharmaceutical compositions comprising the A6-A11 diselenide bridged insulin analogues disclosed herein, and a pharmaceutically acceptable carrier. In accordance with one embodiment a pharmaceutical composition is provided comprising any of the A6-A11 diselenide bridged insulin analogues disclosed herein, preferably at a purity level of at least 90%, 91%, 92%, 93%, 94%, 95%, 96%, 97%, 98% or 99%, and a pharmaceutically acceptable diluent, carrier or excipient. Such compositions may contain an A6-A11 diselenide bridged insulin analogue as disclosed herein at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored within various package containers. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

In accordance with one embodiment an improved method of regulating blood-glucose levels in insulin dependent patients is provided, and more particularly, a method of treating diabetes with a reduced risk of hypoglycemia is provided. The method comprises the steps of administering to a patient an A6-A11 diselenide bridged insulin analogues as disclosed herein in an amount therapeutically effective for the control of diabetes. In one embodiment the A6-A11 diselenide bridged insulin analogues comprises a two-chain prandial insulin analogue comprising an A chain and a B chain linked via interchain disulfide bonds.

BRIEF DESCRIPTION OF THE DRAWINGS

FIG. 1A (SEQ ID NO: 3) is a schematic representation of the sequence of human proinsulin including the A and B chains, and the connecting region, shown with flanking dibasic cleavage sites (filled circles) and C-peptide (open circles). FIG. 1B is a structural model of proinsulin, consisting of an insulin-like moiety and a disordered connecting peptide (dashed line). FIG. 1C (SEQ ID NO: 19) is a schematic drawing of mature insulin showing the naïve disulfide linkages.

FIG. 2A highlights the thiol group (—SH) of Cys compared to the —SeH group contained in Sec. Differences in physicochemical parameters between —SH and —SeH with respect to $pK_a$ (approximately 8.3 for Cys vs approximately 5.2 for Sec) atomic radius (for S, 105 pm vs Se, 120 p,) and $E_o$−220 mV for Cys vs −388 mV for Sec). FIG. 2B is a schematic representation of a diselenide bridge (—Se—Se—) formed between two selenocysteine residues.

FIGS. 8A and 8B provide data for two separate functional studies of insulin or insulin analogues in male Sprague-Dawley rats rendered diabetic by 3-cell poison streptozotocin (STZ). Comparison of insulin lispro (■) versus an analogue of insulin lispro containing paired substitutions [$C6U^A$, $C11U^A$](▲) respectively. Injection of protein-free buffer provided a control (X). Nine rats were studied per group. FIGS. 8C-8E depicts studies of the biological activity of insulin analogues in cell culture of human liver cell-line HepG2. The studies probed transcriptional responses with respect to genes important in respective pathways of gluconeogenesis or lipid synthesis: phosphoenolpyruvate carboxykinase (PEPCK; gluconeogenesis, FIG. 8C), carbohydrate-responsive element-binding protein (ChREBP; lipid synthesis, FIG. 8D) sterol regulatory element-binding proteins (SREBP; lipid synthesis, FIG. 8E) as analyzed by real-time quantitative reverse-transcriptase polymerase chain reaction (rt-q-rtPCR). The decreased downstream accumulation of PEPCK mRNA and increased accumulation of ChREBP and SREBP mRNA provide readouts for insulin-induced transcriptional signaling in liver metabolism. Brackets designate p values (*)<0.05 or (**)<0.01; "ns" indicates p values>0.05.

FIG. 9A contains histograms showing the relative mitogenic signaling (left). Brackets designate p values (*)<0.05 or (**)<0.01; "ns" indicates p values>0.05. Increased expression of the gene encoding cyclin D1 and decreased expression of the gene encoding cyclin G2 are characteristic of cellular proliferation in response to signaling by mitogenic insulin analogues or IGFs. These two-dimensions are simultaneously shown in the panel at right. Mitogenic analogue Asp$^{B10}$-insulin (as known in the art) and mitogenic growth factor IGF-1 provided positive controls as highlighted in the "mitogenic zone" of this plot (gray dashed box). FIG. 9B provides histograms describing IR- and Akt signaling as monitored by their respective phosphorylation. Vertical bars provide the average fold-increase over diluent as analyzed by Western blots of p-IR/IR (left) and p-Akt/Akt (right); * indicates p-value<0.05.

FIG. 10A presents a comparison of CD spectra of WT human insulin versus Se-insulin[C6U$^{A}$, C11U$^{A}$]. FIG. 10B presents a comparison of the unfolding transitions of WT human insulin and Se-insulin[C6U$^{A}$, C11U$^{A}$] as a function of the concentration of guanidine hydrochloride. The unfolding reactions were monitored at 25° C. by ellipticity at helix-sensitive wavelength 222 nm. FIG. 10C presents a comparison of CD spectra of insulin lispro (an engineered insulin monomer and active component of Humalog®; Eli Lilly) versus an analogue of insulin lispro containing paired substitutions [C6U$^{A}$, C11U$^{A}$]. FIG. 10D presents a comparison of the unfolding transitions of WT human insulin and Se-insulin [C6U$^{A}$, C11U$^{A}$] as a function of the concentration of guanidine hydrochloride; the unfolding reactions were monitored as in (B). FIG. 10E depicts the CD spectra of four selenium-containing [C6U$^{A}$, C11U$^{A}$] insulin analogues relative to their native counterparts: WT human insulin, insulin lispro, insulin aspart (Asp$^{B28}$_insulin), and insulin glulisine (Lys$^{B3}$, Glu$^{B29}$-insulin). FIG. 10F provides the respective guanidine unfolding transitions of the eight analogues shown in FIG. 10E; data were obtained under the same conditions employed in FIG. 10D.

FIG. 11A is a graph showing the time course of degradation of WT-insulin and Se-insulin[C6U$^{A}$, C11U$^{A}$] by V8 protease. In this kinetic assay the seleno-analogue is roughly four times more stable than the WT-insulin, with half life $t_{1/2}$=92±3 min versus 25±2 min, respectively. FIG. 11B is a graph showing the resistance to reductive unfolding of WT-insulin and Se-insulin[C6U$^{A}$, C11U$^{A}$] by glutathione in its reduced form. Se-insulin[C6U$^{A}$, C11U$^{A}$] was more resistant to reductive conditions with $t_{1/2}$=40±3 h versus 11±1 h for the WT-insulin. Standard deviations were within ±5%. The data points were fit to a first-order decay function using KaleidaGraph to estimate rate constants, which were used in turn to calculate half lives ($t_{1/2}$). FIG. 11C is a graph summarizing the respective kinetic features of insulin fibrillation for each analogue. Box plot of lag times prior to onset of fibrillations under accelerated conditions at 37° C. The upper- and lower boundaries of boxes represent first and third quartiles, respectively. Upper and lower whiskers demarcate 1.5 times the interquartile range. Mean lag times are represented by gray horizontal lines, and median lag times by black horizontal lines. Lag times of individual replicates are represented by black diamonds; p values of each pair were <0.05.

FIG. 12A-D provide $^{1}$H-NMR spectra of insulin analogs. FIGS. 12A & 12B are one-dimensional (1D) $^{1}$H-NMR spectra of insulin lispro (FIG. 12A) versus its [C6U$^{A}$, C11U$^{A}$] analogue (FIG. 12B) in 10 mM deuterio-acetic acid at pH 3.0 and 25° C. (90% $H_2O$ and 10% $D_2O$). An overall similarity was observed in chemical shifts and extent of chemical-shift dispersion. Sharpening of amide resonances was observed in the diselenide-stabilized analogue (inset; shaded box at top left), suggesting damping of conformational exchange on the millisecond time scale leading to resonance broadening in the parent analogue. FIGS. 12C & 12D provide corresponding 1D spectra of insulin glargine (FIG. 12C) versus its [C6U$^{A}$, C11U$^{A}$] analogue (FIG. 12D). The latter spectrum exhibits more prominent amide resonances and upfield-shifted aliphatic resonances. Conditions were as in FIGS. 12A and 12B. The magnetic field strength corresponded to a proton resonance frequency of 700 MHz.

FIGS. 13A and 13C provide respective 2D NOE cross peaks between aromatic protons (horizontal axis) and aliphatic protons (vertical axis; predominantly the methyl resonances of Ile, Leu and Val). FIGS. 13B and 13D show the respective aromatic regions of the 2D TOCSY spectra. Spectra were obtained in 10 mM deuterio-acetic acid at pD 3.0 (direct meter reading) and 25° C. (99.9% $D_2O$) at 700 MHz. FIG. 13E provides the solution structure of the [C6U$^{A}$, C11U$^{A}$] analogue of insulin lispro. An ensemble of structures is shown at left, and a representative ribbon model at right. The solution structure closely resembles that of insulin lispro. The NMR-derived structure of [C6U$^{A}$, C11U$^{A}$]-modified insulin lispro was calculated on the basis of 866 NOEs as interproton distance restraints and 77 dihedral-angle restraints.

FIGS. 14A & 14B provide 2D TOCSY spectra of [C6U$^{A}$, C11U$^{A}$]-insulin lispro (FIG. 14A) and parent analogue (FIG. 14B) obtained two hours after dissolution in $D_2O$. FIGS. 14C & 14D provide 2D TOCSY spectra of [C6U$^{A}$, C11U$^{A}$]-insulin lispro (FIG. 14C; obtained 69 hours after dissolution in $D_2O$) and parent analogue (FIG. 14D; obtained 58 hours after dissolution in $D_2O$). FIGS. 14E and 14F provides plots of the time course of amide-proton exchange for two (Try$^{A19}$; FIG. 14E and Leu$^{A16}$; FIG. 14F) whose exchange requires global unfolding. In each case exchange of insulin lispro (black) is more rapid than that of the corresponding amide proton in [C6U$^{A}$, C11U$^{A}$]-insulin lispro (gray). This difference at pH 3.0 is smaller than is inferred at pH 7.4 from two-state modeling of guanidine unfolding transitions (see FIGS. 10D & 10F above), but in the same general direction.

FIG. 15A depicts the X-ray crystal structure of Se-insulin[C6U$^{A}$, C11U$^{A}$] and representative electron density. The electron density map corresponding to the region surrounding the A6-A11 diselenide bridge, demonstrating a very good fit of the model of this segment to the corresponding experimental density. FIG. 15B provides a representative structure of a Se-insulin monomer, displaying the diselenide bridge formed between Sec6 and Sec11 of chain A. The structure was extracted from an octameric assembly of Se-insulin protomers in the asymmetric unit of the crystal (not shown).

FIG. 16A depicts the structure of an WT $R_6$ insulin hexamer. The tetrahedral $Zn^{2+}$-coordination site shown as ball-and-stick model in dotted box (insert): three $His^{B10}$ side chains and one chloride ion. FIG. 16B provides visible absorbance spectra of d-d bands in corresponding $Co^{2+}$ complex; the analogue codes are indicated. FIG. 16C presents hexamer dissociation curves as monitored at 574 nm after addition of excess EDTA; the analogue code is as in FIG. 16B. FIG. 16D presents the corresponding dissociation data pertaining to [$C6U^{A}$, $C11U^{A}$]-insulin hexamers. The lifetime of the [$C6U^{A}$, $C11U^{A}$]-insulin analogues were profoundly accelerated (compare solid black line for WT human insulin).

DETAILED DESCRIPTION

Definitions

Figure 1A:
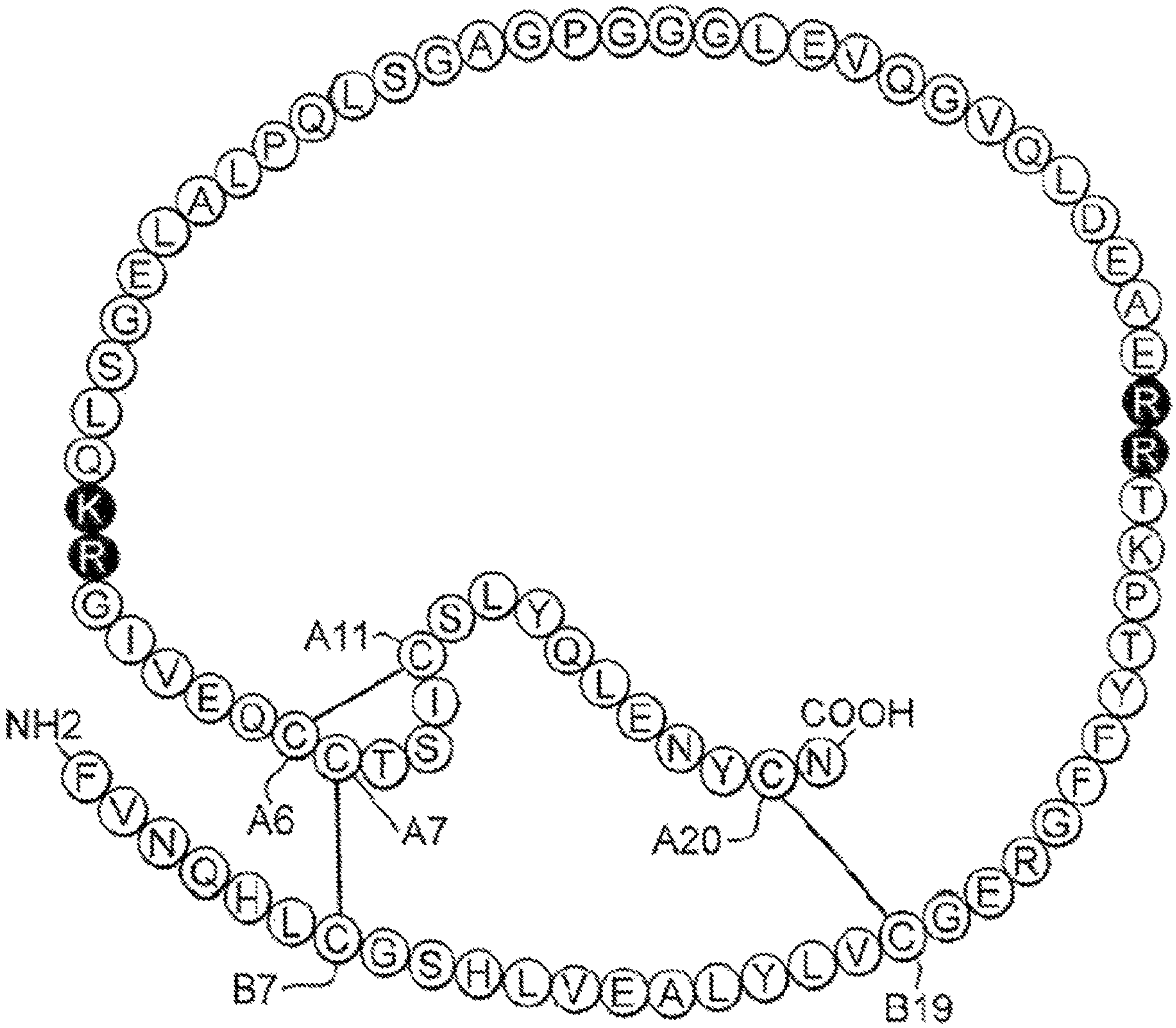
FIGS. 1A-1C are schematic drawings of human insulin.
Figure 1B:
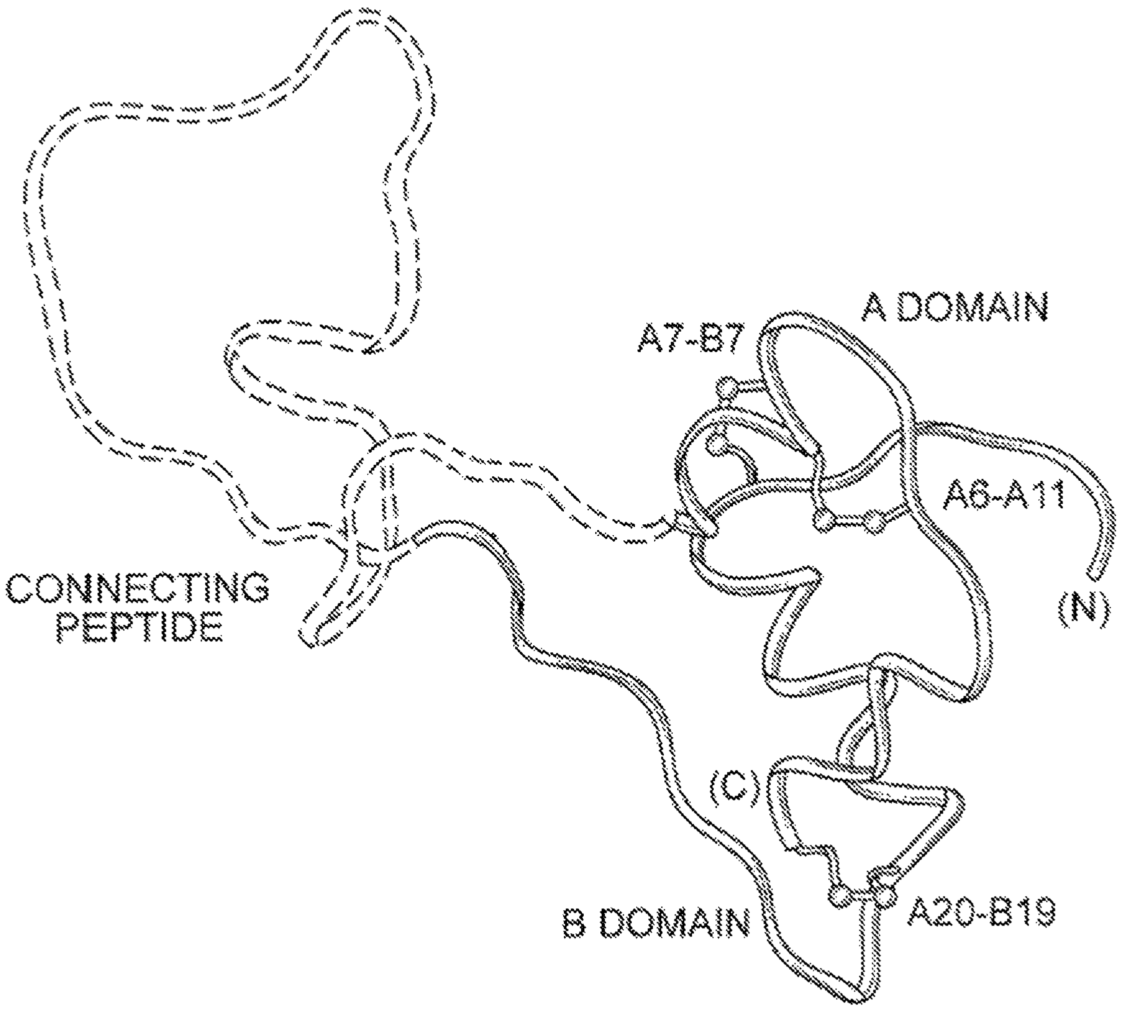
Figure 1C:
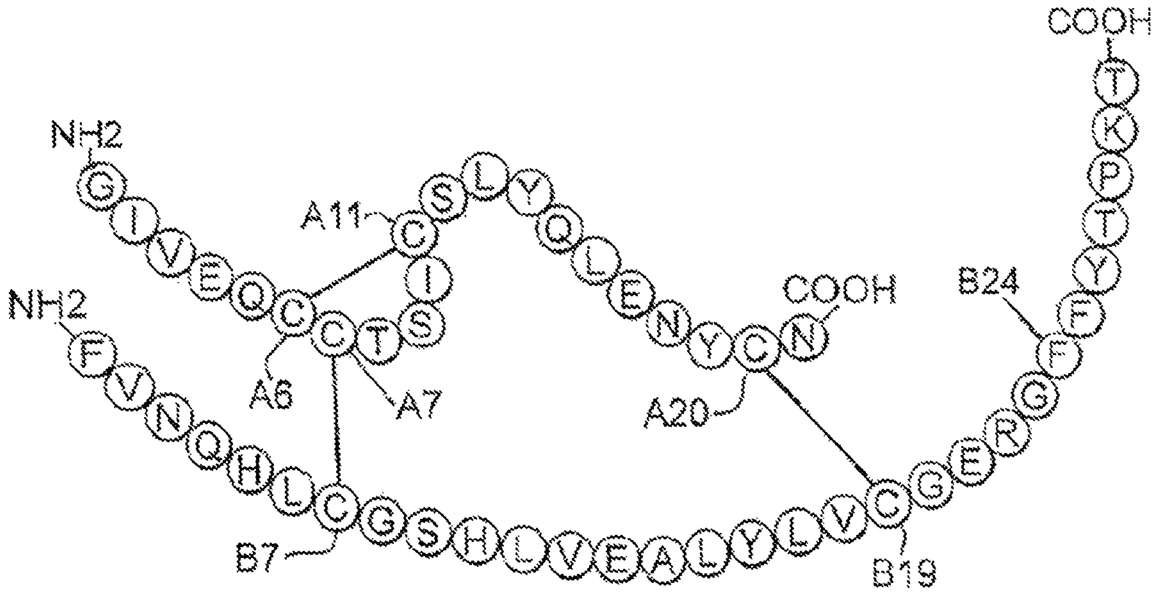

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein the term "amino acid" encompasses any molecule containing both amino and carboxyl functional groups, wherein the amino and carboxylate groups are attached to the same carbon (the alpha carbon). The alpha carbon optionally may have one or two further organic substituents. For the purposes of the present disclosure designation of an amino acid (e.g., by reference to the amino-acid single-letter code) without specifying its stereochemistry is intended to encompass either the L or D form of the amino acid, or a racemic mixture. However, in the instance where an amino acid is designated by its three-letter code and includes a superscript number, the D form of the amino acid is specified by inclusion of a lower case d before the three-letter code and superscript number (e.g., $dLys^{-1}$), wherein the designation lacking the lower case d (e.g., $Lys^{-1}$) is intended to specify the native L form of the amino acid. In this nomenclature, the inclusion of the superscript number designates the position of the amino acid in the sequence of the insulin analogue, wherein amino acids that are located within this sequence are designated by positive superscript numbers numbered consecutively from the N-terminus. Additional amino acids linked to the insulin analogue peptide either at the N-terminus or through a side chain are numbered starting with 0 and increasing in negative integer value as they are further removed from the insulin analogue sequence. Additional amino acids linked to the C-terminal residues of an A- or B chain are numbered as consequetive residues; for example, the C-terminal Arg-Arg extension of the 32-residue B chain in insulin glargine is designed $Arg^{B31}$-$Arg^{B32}$.

As used herein the term "non-coded amino acid" encompasses any amino acid that is not an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr.

A "bioactive polypeptide" refers to polypeptides that are capable of exerting a biological effect in vitro and/or in vivo.

As used herein a general reference to a peptide/polypeptide is intended to encompass peptides/polypeptides that have modified amino- and/or carboxy termini. For example, an amino-acid sequence designating the standard amino acids is intended to encompass standard amino acids at the N- and C terminus as well as modified amino acids, such as a corresponding C-terminal amino acid modified to comprise an amide group in place of the terminal carboxylic acid.

As used herein an "acylated" amino acid is an amino acid comprising an acyl group that is non-native to a naturally-occurring amino acid, regardless by the means by which it is produced. Exemplary methods of producing acylated amino acids and acylated peptides are known in the art; these include acylating an amino acid before inclusion in the peptide or chemical acylation of the peptide following its complete synthesis. In some embodiments the acyl group causes the peptide to have one or more of (i) a prolonged half-life in circulation, (ii) a delayed onset of action, (iii) an extended duration of action, (iv) an improved resistance to proteases and (v) increased or decreased potency at insulin receptor isoforms.

As used herein, an "alkylated" amino acid is an amino acid containing an alkyl group that is non-native to a naturally-occurring amino acid, regardless of the means by which it is produced. Exemplary methods of producing alkylated amino acids and alkylated peptides are known in the art; these include alkylating an amino acid before inclusion in the peptide or chemical alkylation of the peptide following its synthesis. Without being held to any particular theory, it is believed that alkylation of peptides will achieve similar, if not the same, effects as acylation of the peptides, e.g., a prolonged half-life in circulation, a delayed onset of action, an extended duration of action, an improved resistance to proteases and increased or decreased potency.

As used herein, the term "pharmaceutically acceptable carrier" includes any of the standard pharmaceutical carriers, such as a phosphate-buffered saline (PBS) solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" encompasses salts of compounds that retain the biological activity of the parent compound and that are not biologically or otherwise undesirable. Many of the compounds disclosed herein are capable of forming acid and/or base salts by virtue of the presence of amino and/or carboxyl groups or groups similar thereto.

As used herein, the term "hydrophilic moiety" encompasses any compound that is readily water-soluble or readily absorbs water, and that are tolerated in vivo by mammalian species without toxic effects (i.e., are biocompatible). Examples of hydrophilic moieties include polyethylene glycol (PEG), polylactic acid, polyglycolic acid, a polylactic-polyglycolic acid copolymer, polyvinyl alcohol, polyvinylpyrrolidone, polymethoxazoline, polyethyloxazoline, polyhydroxyethyl methacrylate, polyhydroxypropyl methacrylamide, polymethacrylamide, polydimethylacrylamide, and derivatised celluloses such as hydroxymethylcellulose or hydroxyethylcellulose and co-polymers thereof, as well as natural polymers including, for example, albumin, heparin and dextran.

As used herein, the term "treating" includes prophylaxis of the specific disorder or condition, or alleviation of the symptoms associated with a specific disorder or condition and/or preventing or eliminating said symptoms. For example, as used herein the term "treating diabetes" (or "treating DM") will refer in general to maintaining blood-glucose concentrations near normal levels and may include increasing or decreasing blood-glucose levels depending on a given situation.

As used herein, an "effective" amount or a "therapeutically effective amount" of an insulin analogue refers to a nontoxic but sufficient amount of an insulin analogue to provide the desired effect. For example one desired effect would be the prevention or treatment of hyperglycemia. The amount that is "effective" will vary from subject to subject, depending on the age and general condition of the individual, mode of administration, nutritional status and the like. Thus, it is not always possible to specify an exact "effective amount." However, an appropriate "effective" amount in any individual case may be determined by one of ordinary skill in the art using routine experimentation.

The term "parenteral" means not through the alimentary canal but by some other route such as intranasal, inhalation, subcutaneous (SQ), intramuscular, intraspinal, or intravenous (IV).

Throughout this application, all references to a particular amino-acid position by letter and number (e.g., position A5) refer to the amino acid at that position of either the A chain (e.g., position A5 with respect to SEQ ID NO: 2) or the B chain (e.g., position B5 with respect to SEQ ID NO: 4) or the corresponding amino-acid position in any insulin analogues thereof. For example, a reference herein to "position B28" absent any further elaboration could mean residue $Pro^{B28}$ in WT insulin or the corresponding position 27 of a variant B chain in an insulin analogue in which the first amino acid of SEQ ID NO: 4 has been deleted (des-B1). Similarly, amino acids added to the N-terminus of the native B chain are numbered starting with B0, followed by numbers of increasing negative value (e.g., B−1, B−2 . . . ) as amino acids are added to the N-terminus.

As used herein, the term "native human insulin peptide" is intended to designate the 51 amino-acid heteroduplex comprising the A chain of SEQ ID NO: 2 and the B chain of SEQ ID NO: 4, as well as single-chain insulin (SCI) analogues that comprise SEQ ID NOS: 2 and 4 (i.e., as an A domain and a B domain). The term "insulin polypeptide" or "insulin peptide" as used herein, absent further descriptive language is intended to encompass the 51 amino-acid heteroduplex comprising the A chain of SEQ ID NO: 2 and the B chain of SEQ ID NO: 4; single-chain insulin analogues containing the native C domain of proinsulin, foreshortened C domains, novel connecting peptides, or non-peptidic linkers between the C terminus of the B chain and N-terminis of the A chain are herein collectively designated SCIs (including for example those disclosed in published international application WO96/34882 and U.S. Pat. No. 6,630,348, the disclosures of which are incorporated herein by reference). The class of SCIs thus contains homologous peptide hormones (e.g., IGF1 and IGF2) and their variants that have activity at one or both of the insulin receptor isoforms. Such modified analogues include amino-acid modifications at one or more amino positions selected from A5, A8, A9, A10, A12, A14, A15, A17, A18, A21, B1, B2, B3, B4, B5, B9, B10, B13, B14, B17, B20, B21, B22, B23, B26, B27, B28, B29 and B30 or deletions of any or all of positions B1-4 and B26-30. Insulin polypeptides as defined herein can also be analogues derived from a naturally occurring insulin by insertion or substitution of a non-peptide moiety, e.g., a retroinverso fragment, or incorporation of non-peptide bonds such as an azapeptide bond (CO substituted by NH) or pseudo-peptide bond (e.g., NH substituted with $CH_2$) or an ester bond (e.g., a depsipeptide, wherein one or more of the amide (—CONHR—) bonds are replaced by ester (COOR) bonds).

As used herein, the term "insulin A chain," absent further descriptive language is intended to encompass the 21 amino-acid sequence of SEQ ID NO: 2 as well as functional analogues and derivatives thereof known to those skilled in the art, including modification of the sequence of SEQ ID NO: 2 by one or more amino-acid substitutions at positions selected from A4, A5, A8, A9, A10, A12, A14, A15, A17, A18, A21.

As used herein, the term "insulin B chain," absent further descriptive language is intended to encompass the 30 amino-acid sequence of SEQ ID NO: 4, as well as modified functional analogues of the native B chain, including one or more amino-acid substitutions at positions selected from B1, B2, B3, B4, B5, B9, B10, B13, B14, B17, B20, B21, B22, B23, B25, B26, B27, B28, B29 and B30 or deletions of any or all of positions B1-4 and B26-30.

As used herein, the term "derivative" is intended to encompass chemical modification to a compound (e.g., an amino acid), including chemical modification in vitro, e.g., by introducing a group in a side chain in one or more positions of a polypeptide, e.g., a nitro group in a tyrosine residue or iodine in a tyrosine residue, or by conversion of a free carboxylic group to an ester group or to an amide group, or by converting an amino group to an amide by acylation, or by acylating a hydroxy group rendering an ester, or by alkylation of a primary amine rendering a secondary amine or linkage of a hydrophilic moiety to an amino-acid side chain. Other derivatives are obtained by oxidation or reduction of the side chains of the amino-acid residues in the polypeptide.

The term "identity" as used herein relates to the similarity between two or more sequences. Identity is measured by dividing the number of identical residues by the total number of residues and multiplying the product by 100 to achieve a percentage. Thus, two copies of exactly the same sequence have 100% identity, whereas two sequences that have amino-acid deletions, additions, or substitutions relative to one another have a lower degree of identity. Those skilled in the art will recognize that several computer programs, such as those that employ algorithms such as BLAST (Basic Local Alignment Search Tool, Altschul et al. (1993) J. Mol. Biol. 215:403-410), are available for determining sequence identity.

As used herein, an amino-acid "modification" refers to a substitution of an amino acid, or the derivation of an amino acid by the addition and/or removal of chemical groups to/from the amino acid, and includes substitution with any of the 20 amino acids commonly found in human proteins, as well as atypical or non-naturally occurring amino acids. Commercial sources of atypical amino acids include Sigma-Aldrich (Milwaukee, WI), ChemPep Inc. (Miami, FL), and Genzyme Pharmaceuticals (Cambridge, MA). Atypical amino acids may be purchased from commercial suppliers, synthesized de novo, or chemically modified or derivatized from naturally occurring amino acids.

As used herein, an amino-acid "substitution" refers to the replacement of one amino-acid residue by a different amino-acid residue.

As used herein, the term "conservative amino-acid substitution" is defined herein as exchanges within one of the following five groups:

I. Small aliphatic, nonpolar or slightly polar residues: Ala, Ser, Thr, Pro, Gly;

II. Polar, negatively charged residues and their amides: Asp, Asn, Glu, Gln, cysteic acid and homocysteic acid;

III. Polar, positively charged residues: His, Arg, Lys; Ornithine (Orn)

IV. Large, aliphatic, nonpolar residues: Met, Leu, Ile, Val, Cys, Norleucine (Nle), homocysteine V. Large, aromatic residues: Phe, Tyr, Trp, acetyl phenylalanine As used herein, the general term "polyethylene-glycol chain" (or "PEG chain") encompasses mixtures of condensation polymers of ethylene oxide and water, in a branched or straight chain, represented by the general formula $H(OCH_2CH_2)_nOH$, wherein n is at least 2. "Polyethylene-glycol chain" (or "PEG chain") is used in combination with a numeric suffix to indicate the approximate average molecular weight thereof. For example, PEG-5,000 refers to polyethylene-glycol chain having a total molecular weight average of about 5,000 Daltons.

As used herein, the term "pegylated" and like terms include any compound that has been modified from its native state by linking a polyethylene-glycol chain to the compound. A "pegylated polypeptide" is a polypeptide that has a PEG chain covalently bound to the polypeptide.

As used herein, a "linker" is a bond, molecule or group of molecules that binds two separate entities to one another. Linkers may provide for optimal spacing of the two entities or may further supply a labile linkage that allows the two entities to be separated from each other. Labile linkages include photocleavable groups, acid-labile moieties, base-labile moieties and enzyme-cleavable groups.

As used herein, an "insulin dimer" is a complex comprising two insulin molecules (each containing an A and B chain) bound to each other through reversible non-covalent interactions, such as van der Waal interactions, electrostatic interactions and hydrogen bonds. Solutions of insulin in the absence of zinc ions at neutral pH and at protein concentrations greater than 1 μM typically exhibit an equilibrium distribution of monomeric insulin molecules, insulin dimers and higher-order oligomers. The term insulin dimer, when used absent any qualifying language, encompasses both insulin homodimers and insulin heterodimers. An insulin homodimer comprises two identical insulin polypeptides, whereas an insulin heterodimer comprises two insulin polypeptides that differ; an example of an insulin heterodimer would be provided by the association of a human insulin molecule with a bovine insulin molecule. As used herein, the term "covalent insulin dimer" designates two insulin molecules connected to each other by one or more a non-native covalent bonds; an example of such a bond would be an intermolecular disulfide bridge. Formation of covalent insulin dimers is known in the art as a mechanism of chemical degradation.

As used herein, the term "patient" without further designation is intended to encompass any warm-blooded vertebrate domesticated animal (including for example, but not limited to livestock, horses, cats, dogs and other pets) and humans.

The term "isolated" as used herein means having been removed from its natural environment. In some embodiments the analogue is made through recombinant methods wherein the analogue is isolated from the host cell, which typically may be a bacterial cell, yeast cell, inset cell or mammalian cell.

The term "purified" as used herein encompasses the isolation of a molecule or compound in a form that is substantially free of contaminants normally associated with the molecule or compound in a native or natural environment; in practice this means having been increased in purity as a result of being separated from other components of the original composition. The term "purified polypeptide" is used herein to describe a polypeptide which has been separated from other compounds including, but not limited to nucleic-acid molecules, lipids and carbohydrates.

Abbreviations

Insulin analogues will be abbreviated as follows:

The insulin A- and B chains will be designated by a capital A for the A chain and a capital B for the B chain wherein a superscript 0 (e.g., $A^0$ or $B^0$) will designate the base sequence is an insulin sequence (A chain: SEQ ID NO: 2, B chain SEQ ID NO: 4). Modifications that deviate from the native insulin are indicated in parenthesis following the designation of the A or B chain (e.g., [$B^1$(H5,H10,Y16,L17):$A^1$(H8,N18,N21)]) with the single-letter amino-acid abbreviation indicating the substitution and the number indicating the position of the substitution in the respective A or B chain, using native insulin numbering. A colon between the A and B chain indicates a two-chain insulin.

EMBODIMENTS

Figure 2A:
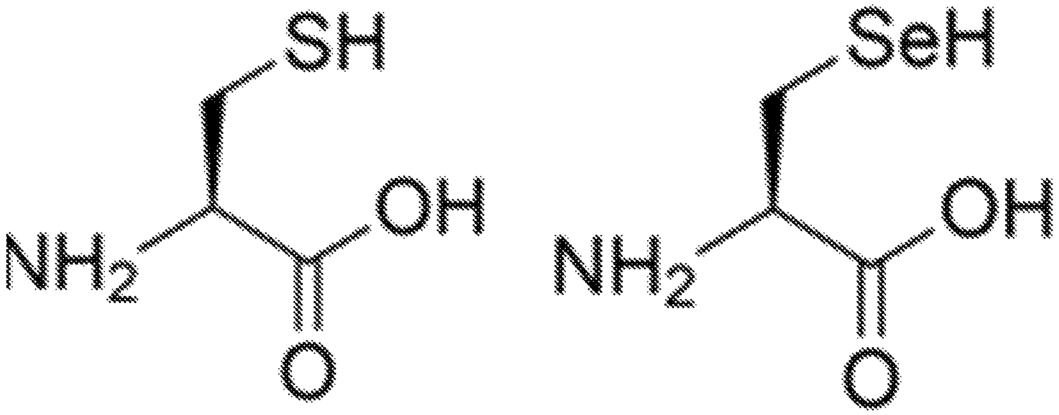
FIGS. 2A & 2B provide molecular representations of selenocysteine (Sec) versus native cysteine (Cys).
Figure 2B:
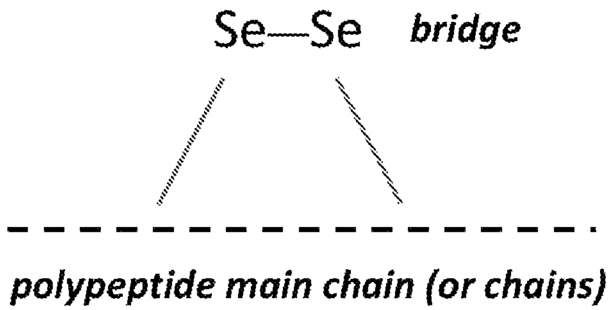
Figure 2C:
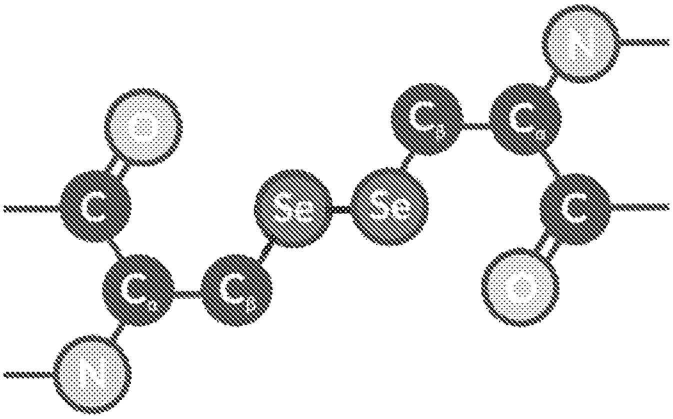
FIG. 2C provides a ball-and-stick model of a diselenide bridge.
Figure 3:
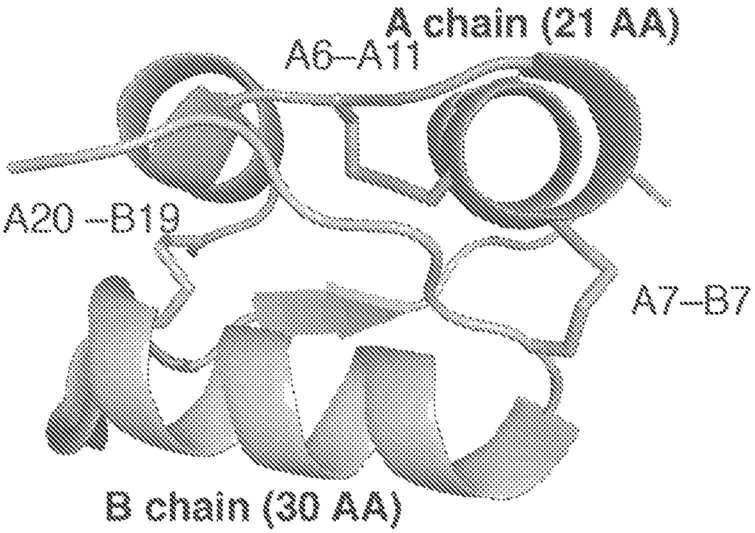
FIG. 3 presents a ribbon model of wild type (WT) insulin (a single T-state protomer as derived from the crystal structure of a zinc-stabilized hexamer) in which the protein's three disulfide bridges are highlighted: cystine A20-B19, cystine A7-B7 and cystine A6-A11 are indicated. The A-chain ribbon and B-chain ribbon are marked.
Figure 4:
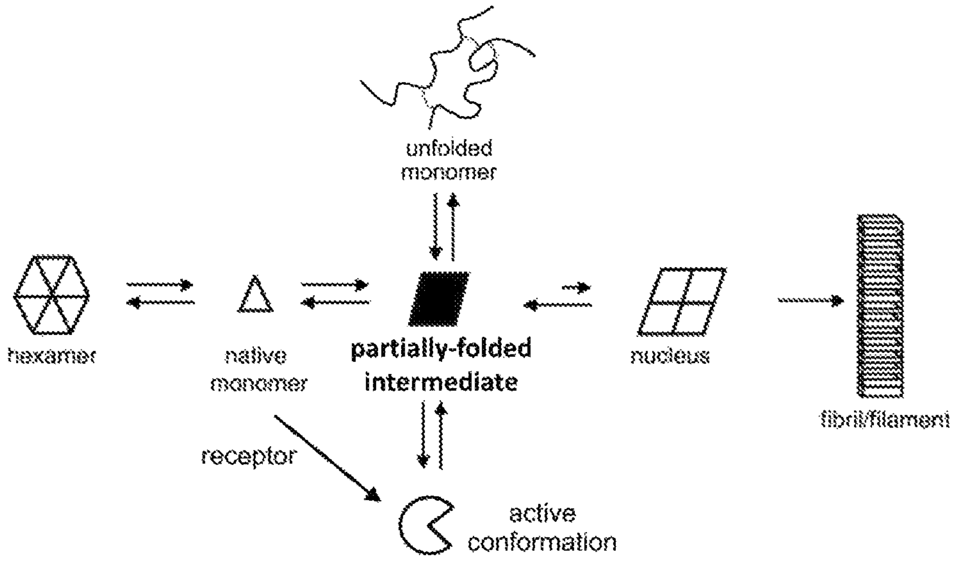
FIG. 4 provides a scheme for the mechanism of insulin fibrillation. The protective storage form of insulin as a hexamer is shown at far left, and a protofilament is shown at far right. The horizontal pathway proceeds from the hexamer to the native monomer (triangle), partially folded intermediate (trapezoid), and putative amyloidogenic nucleus (as represented by four conjoined trapezoids). Above and below this pathway are shown the fully denatured state with intact disulfide bridges (top) and the receptor-bound distorted conformation of the insulin monomer (bottom).

The present disclosure is directed toward an insulin analogue that exhibits enhanced stability in vitro due to pairwise substitution of $Cys^{A6}$ and $Cys^{A11}$ by selenocysteine (three-letter code Sec; single-letter code U) as illustrated in FIG. 2C. The replacement of an internal disulfide bridge by an internal diselenide bridge at this position enhances the efficiency of core packing within the interior of the insulin molecule. Although not wishing to be limited by theory, this larger bridge between residues A6 and A11 damps conformational fluctuations that otherwise contribute to the susceptibility of WT human insulin to chemical and physical degradation—with special attention to the mechanism of fibrillation. It is another feature of the present disclosure that a diselenide bridge between residues A6 and A11 augments the thermodynamic stability of the insulin monomer and by so doing also protects the insulin dimer and zinc insulin hexamer, even if association constants are similar or reduced.

It is yet another feature of the present disclosure that $Sec^{A6}$ and $Sec^{A11}$ may be introduced pairwise into diverse analogues of human insulin, such as insulin lispro, insulin aspart and insulin glulisine (rapid-acting insulin analogue in current clinical use by patients with DM) and likewise confer favorable stabilization and protection from degradation. Introduction of a diselenide bridge between residues A6 and A11 thereby provides a general approach to extend the shelf-life of insulin analogue products. It is a further aspect of the present disclosure that the disclosed modification to the core of insulin does not significantly alter its receptor-binding surface, such that the pharmacologic, biological and therapeutic properties of the diselenide-stabilized derivative are similar to those of the parent insulin analogue.

In accordance with one embodiment an insulin peptide analogue is provided wherein a pairwise substitution of $Cys^{A6}$ and $Cys^{A11}$ in WT human insulin by $Sec^{A6}$ and $Sec^{A11}$ is made. It is another embodiment that these substitutions are introduced into a series of insulin analogues known in the art to exhibit more rapid absorption on SQ injection than does WT insulin; examples are provided by insulin lispro ($Pro^{B28}$→Lys and $Lys^{B29}$→Pro; Eli Lilly), insulin aspart ($Pro^{B28}$→Asp; Novo-Nordisk) and insulin glulisine ($Lys^{B29}$→Glu and $Asn^{B3}$→Lys; Sanofi). Alternative embodiments may employ ornithine, diaminobutyric acid or diaminopropionic acid in place of lysine at positions B28 or B3. In yet other embodiments the parent insulin analogue is a long-acting hormone as known in the art; examples are provided by insulin detemir (Levemir®; Novo-Nordisk), insulin degludec (Tresiba®; Novo-Nordisk) and insulin glargine (Lantus® and Toujeo®; Sanofi). The present disclosure envisions that all these current insulin products can be favorably modified by the present disclosure to provide improved products, i.e., with longer shelf life. The above set of embodiments can be further modified to include amino-acid substitutions known to occur naturally among vertebrate insulins, such as $Ala^{B30}$ instead of $Thr^{B30}$ (as is characteristic of porcine insulin and bovine insulin).

Furthermore, in view of the similarity between human and animal insulins, and use in the past of animal insulins in human patients with diabetes mellitus, it is also envisioned that other minor modifications in the sequence of insulin may be introduced, especially those substitutions considered "conservative." For example, additional substitutions of amino acids may be made within groups of amino acids with similar side chains, without departing from the present invention. These include the neutral hydrophobic amino acids: Alanine (Ala or A), Valine (Val or V), Leucine (Leu or L), Isoleucine (Ile or I), Proline (Pro or P), Tryptophan (Trp or W), Phenylalanine (Phe or F) and Methionine (Met or M). Likewise, the neutral polar amino acids may be substituted for each other within their group of Glycine (Gly or G), Serine (Ser or S), Threonine (Thr or T), Tyrosine (Tyr or Y), Cysteine (Cys or C), Glutamine (Glu or Q), and Asparagine (Asn or N). Acidic amino acids are Aspartic acid (Asp or D) and Glutamic acid (Glu or E). Introduction of basic amino-acid substitutions (including Lysine (Lys or K), Arginine (Arg or R) and Histidine (His or H)) are not preferred in order to maintain the enhanced net negative charge of this class of analogues. Unless noted otherwise or wherever obvious from the context, the amino acids noted herein should be considered to be L-amino acids. Standard amino acids may also be substituted by non-standard amino acids belonging to the same chemical class.

It is a general feature of the present disclosure that pairwise substitution of $Cys^{A6}$ and $Cys^{A11}$ by $Sec^{A6}$ and $Sec^{A11}$ enhances the speed and fidelity of insulin chain combination. The B chain in such reactions may be synthetic or biosynthetic in origin; its sequence may conform to that of WT insulin or contain amino-acid substitutions intended to modify the pharmacologic, biophysical or biological properties of the final insulin analogue. It is yet another general feature of the present disclosure that pairwise substitution of $Cys^{A6}$ and $Cys^{A11}$ by $Sec^{A6}$ and $Sec^{A11}$ likewise enhances the speed and fidelity of oxidative folding of single-chain insulin analogues, as exemplified by Des-Di (a 49-residue polypeptide containing substitution $Pro^{B28}$→Lys and a peptide bond between $Lys^{B28}$ and $Gly^{A1}$ with deletion of residues B29 and B30). A diselenide bridge at positions A6 and A11 is also anticipated to enhance the folding of longer single-chain insulin precursor polypeptides, including proinsulin itself (86 residues).

In one embodiment the presently disclosed insulin analogues have been reduced to practice as illustrated by a molecular embodiment in the context of insulin lispro, insulin aspart, insulin glulisine and insulin glargine The first three examples (prandial analogues in current clinical use; respectively known as Humalog® [Eli Lilly and Co.], Novolog® [Novo-Nordisk] and Apidra® [Sanofi])) demonstrate the utility of paired selenocysteine substitutions at positions A6 and A11 within a prototypical rapid-acting insulin in current clinical use, including in pumps. The fourth analogue is the active ingredient of basal insulin analogue formulation in current clinical use (Lantus® and Toujeo®; Sanofi).

As background, an analogue of WT human insulin containing pairwise substitution of $Cys^{A6}$ and $Cys^{A11}$ by $Sec^{A6}$ and $Sec^{A11}$ was prepared by insulin chain combination. This protocol employs a synthetic A chain and a WT B chain, obtained either by oxidative sulfitolysis of biosynthetic human insulin (as employed herein) or chemical peptide synthesis. The general protocol for solid-phase synthesis is as described (Merrifield et al., 1982. *Biochemistry* 21: 5020-5031).

As described in the Examples, the [C6U$^{A}$, C11U$^{A}$] analogue of WT human insulin exhibited native-like structure and function with enhanced stability (relative to WT insulin). Examples are provided based on diselenide-based protection of three prandial insulin analogues in current clinical use: insulin lispro, insulin aspart and insulin glulisine.

The present disclosure provides the basis for improved products to treat DM by means of a pharmaceutical formulation intended for SQ injection. In still another example, the insulin analogue is administered by an external or implantable insulin pump. A pharmaceutical composition may comprise such insulin analogues and may optionally include zinc. In one embodiment zinc ions may not be needed to stabilize a pharmaceutical formulation due to the intrinsic stability conferred by the presently disclosed diselenide bridge at positions A6 and A11. Zinc ions may nonetheless be included in such a composition at a level of a molar ratio of between 2.2 and 3.0 per hexamer of the insulin analogue; higher concentrations of zinc ions may be present in acidic formulations of pI-shifted insulin analogues such as insulin glargine. In such formulations the concentration of the insulin analogue would typically be between about 0.1 and about 3 mM; concentrations up to 3 mM may be used in the reservoir of an insulin pump. Modifications of meal-time insulin analogues may be formulated as described for (a) "regular" formulations of Humulin® (Eli Lilly and Co.), Humalog® (Eli Lilly and Co.), Novalin® (Novo-Nordisk), and Novolog® (Novo-Nordisk) and other rapid-acting insulin formulations currently approved for human use, (b) "NPH" formulations of the above and other insulin analogues, and (c) mixtures of such formulations. (c) Yet another class of pharmaceutical formulations encompass long-acting insulin products as exemplified by U-100 and U-300 strengths of insulin glargine under acidic conditions (Sanofi) and acylated insulin analogues such as insulin detemir and insulin degludec at neutral pH (Novo-Nordisk).

Excipients may include glycerol, glycine, other buffers and salts, and anti-microbial preservatives such as phenol and meta-cresol; the latter preservatives are known to enhance the stability of the insulin hexamer. Such a pharmaceutical composition may be used to treat a patient having diabetes mellitus or other medical condition by administering a physiologically effective amount of the composition to the patient.

Based upon the foregoing disclosure, it should now be apparent that [$Sec^{A6}$, $Sec^{A11}$]-substituted insulin analogues will carry out the objects set forth hereinabove. Namely, these insulin analogues exhibit enhanced thermodynamic stability, resistance to fibrillation with maintenance of potency in reducing blood-glucose levels at a level similar to that of the parent insulin analogue. It is, therefore, to be understood that any variations evident fall within the scope of the claimed invention and thus, the selection of specific component elements can be determined without departing from the spirit of the invention herein disclosed and described.

In one embodiment an insulin receptor agonist analogue is provided wherein the analogue comprises an insulin A chain and an insulin B chain wherein said A chain comprises a sequence of $GIVX_4X_5X_6CX_8X_9X_{10}X_{11}X_{12}LX_{14}X_{15}LX_{17}X_{18}YCX_{21}$—$R_{53}$ (SEQ ID NO: 10), and said B chain comprises a sequence $R_{62}$-$X_{25}LCGX_{29}X_{30}LVX_{33}X_{34}LYLVCGX_{41}X_{42}GFX_{45}$ (SEQ ID NO: 11), wherein $X_4$ is glutamic acid or aspartic acid;

$X_5$ is glutamine or glutamic acid;

$X_6$ is selenocysteine;

$X_8$ is histidine, threonine, lysine, arginine, tryptophan or phenylalanine;

$X_9$ is serine, arginine, lysine, ornithine or alanine;

$X_{10}$ is isoleucine or serine;

$X_{11}$ is selenocysteine;

$X_{12}$ is serine or aspartic acid;

$X_{14}$ is tyrosine, arginine, lysine, ornithine or alanine;

$X_{15}$ is glutamine, glutamic acid, arginine, alanine, lysine, ornithine or leucine;

$X_{17}$ is glutamic acid, aspartic acid, asparagine, lysine, ornithine or glutamine;

$X_{18}$ is methionine, asparagine, glutamine, aspartic acid, glutamic acid or threonine;

$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

$X_{25}$ is histidine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{41}$ is selected from the group consisting of glutamic acid, aspartic acid and asparagine;

$X_{42}$ is selected from the group consisting of alanine, ornithine, lysine and arginine;

$X_{45}$ is tyrosine or phenylalanine;

$R_{62}$ is selected from the group consisting of AYRPSE (SEQ ID NO: 12), FVNQ (SEQ ID NO: 13), PGPE (SEQ ID NO: 14), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal amine; and $R_{53}$ is COOH or $CONH_2$, wherein a diselenide bridge is formed between the side chains of residues A6 and A11.

In one embodiment $X_4$ is glutamic acid or aspartic acid; $X_5$ is glutamine or glutamic acid; $X_6$ is selenocysteine; $X_8$ is histidine, threonine or phenylalanine; $X_9$ is serine or arginine; $X_{10}$ is isoleucine or serine; $X_{11}$ is selenocysteine; $X_{12}$ is serine or aspartic acid; $X_{14}$ is tyrosine, arginine or alanine; $X_{15}$ is glutamine, arginine, or leucine; $X_{17}$ is glutamic acid or aspartic acid; $X_{18}$ is methionine, asparagine or threonine; $X_{21}$ is selected from the group consisting of alanine, glycine and asparagine; $X_{25}$ is histidine or threonine; $X_{29}$ is selected from the group consisting of alanine, glycine and serine; $X_{30}$ is selected from the group consisting of histidine, aspartic acid and glutamic acid; $X_{33}$ is selected from the group consisting of aspartic acid and glutamic acid; $X_{34}$ is selected from the group consisting of alanine and threonine; $X_{41}$ is selected from the group consisting of glutamic acid and aspartic acid; $X_{42}$ is arginine; and $X_{45}$ is tyrosine or phenylalanine.

In one embodiment an insulin analogue is provided wherein the insulin A chain comprises the sequence $GIVEQX_6CX_8SIX_{11}SLYQLENYCX_{21}$-$R_{53}$ (SEQ ID NO: 15) and the insulin B chain comprises the sequence $FVX_{23}QX_{25}LCGSHLVEALYLVCGERGFFYTX_{48}X_{49}X_{50}$ (SEQ ID NO: 16), wherein $X_6$ is seleno-cysteine;

$X_8$ is histidine, threonine, lysine, arginine, phenylalanine or tryptophan;

$X_{11}$ is seleno-cysteine; and $X_{21}$ is selected from the group consisting of alanine, glycine, serine, threonine, glutamine, asparagine, and aspartic acid;

$X_{23}$ is Asn or Lys:

$X_{25}$ is histidine or threonine;

$X_{48}$ is proline, lysine or aspartic acid;

$X_{49}$ is proline, lysine or glycine;

$X_{50}$ is threonine, alanine or serine; and $R_{53}$ is COOH or $CONH_2$.

In one embodiment an insulin analogue is provided wherein the A chain comprises the sequence $GIVEQX_6CX_8X_9IX_{11}SLYQLENYCX_{21}$-$R_{53}$ (SEQ ID NO: 17) and said B chain comprises the sequence $FVX_{23}QX_{25}LCGX_{29}X_{30}LVX_{33}X_{34}LYLVCGX_{41}X_{42}GFX_{45}$ (SEQ ID NO: 18), wherein $X_6$ is selenocysteine;

$X_8$ is histidine or threonine;

$X_9$ is serine, lysine, or alanine;

$X_{11}$ is selenocysteine;

$X_{21}$ is alanine, glycine or asparagine;

$X_{23}$ is asparagine or lysine;

$X_{25}$ is histidine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{41}$ is selected from the group consisting of glutamic acid, aspartic acid and asparagine;

$X_{42}$ is selected from the group consisting of alanine, ornithine, lysine and arginine;

$X_{45}$ is tyrosine or phenylalanine;

$R_{53}$ is COOH or $CONH_2$.

In a further embodiment the A chain comprises the sequence $GIVEQX_6CX_8X_9IX_{11}SLYQLENYCX_{21}$-$R_{53}$ (SEQ ID NO: 17) and said B chain comprises the sequence FVNQHLCGSHLVEALYLVCGERGFFY (SEQ ID NO: 50), or FVKQHLCGSHLVEALYLVCGERGFFY (SEQ ID NO: 51, wherein $X_6$ is selenocysteine;

$X_8$ is histidine or threonine;

$X_9$ is serine, lysine, or alanine;

$X_{11}$ is selenocysteine;

$X_{21}$ is alanine, glycine or asparagine; and $R_{53}$ is COOH or $CONH_2$.

In a further embodiment the A chain comprises the sequence GIVEQ$X_6$C$X_8$$X_9$I$X_{11}$SLYQLENYC$X_{21}$-$R_{53}$ (SEQ ID NO: 17) and said B chain comprises a sequence selected from the group consisting of FVNQHLCGSHLVEALYLVCGERGFFYTPKT (SEQ ID NO: 4), FVNQHLCGSHLVEALYLVCGERGFFYTPKT (SEQ ID NO: 4), FVNQHLCGSHLVEALYLVCGERGFFYTDKT (SEQ ID NO: 5), FVNQHLCGSHLVEALYLVCGERGFFYTKPT (SEQ ID NO: 6), FVKQHLCGSHLVEALYLVCGERGFFYTPET (SEQ ID NO: 7), FVNQHLCGSHLVEALYLVCGERGFFYTPKTRR (SEQ ID NO: 8), and FVNQHLCGSHLVEALYLVCGERGFFYTP$X_{29}$$X_{30}$ (SEQ ID NO: 9), wherein $X_6$ is selenocysteine;

$X_8$ is histidine or threonine;

$X_9$ is serine, lysine, or alanine;

$X_{11}$ is selenocysteine;

$X_{21}$ is alanine, glycine or asparagine;

$X_{29}$ is an acyl derivative of lysine or glutamic-acid-bridged acyl derivative of Lysine $X_{30}$ is Thr, Ala, Ser or absent; and $R_{53}$ is COOH or $CONH_2$.

In another embodiment the A chain comprises the sequence GIVEQ$X_6$C$X_8$SI$X_{11}$SLYQLENYC$X_{21}$-$R_{53}$ (SEQ ID NO: 15) and said B chain comprises a sequence selected from the group consisting of

```
                                   (SEQ ID NO: 4)
FVNQHLCGSHLVEALYLVCGERGFFYTPKT,

                                   (SEQ ID NO: 5)
FVNQHLCGSHLVEALYLVCGERGFFYTDKT,

                                   (SEQ ID NO: 6)
FVNQHLCGSHLVEALYLVCGERGFFYTKPT, and

                                   (SEQ ID NO: 7)
FVKQHLCGSHLVEALYLVCGERGFFYTPET,
```

wherein $X_6$ is selenocysteine;

$X_8$ is histidine or threonine;

$X_{11}$ is selenocysteine;

$X_{21}$ is alanine, glycine or asparagine; and $R_{53}$ is COOH or $CONH_2$.

In one embodiment an insulin analogue is provided wherein the A chain comprises a sequence GIVEQ$X_6$CTSI$X_{11}$SLYQLENYCN (SEQ ID NO: 30) and said B chain comprises a sequence selected from the group consisting of FVNQHLCGSHLVEALYLVCGERGFFYTPKT (SEQ ID NO: 4), FVNQHLCGSHLVEALYLVCGERGFFYTDKT (SEQ ID NO: 5), FVNQHLCGSHLVEALYLVCGERGFFYTKPT (SEQ ID NO: 6), FVKQHLCGSHLVEALYLVCGERGFFYTPET (SEQ ID NO: 7), FVNQHLCGSHLVEALYLVCGERGFFYTPKTRR (SEQ ID NO: 8), and FVNQHLCGSHLVEALYLVCGERGFFYTP$X_{29}$$X_{30}$ (SEQ ID NO: 9), wherein $X_6$ is selenocysteine;

$X_{11}$ is selenocysteine;

$X_{29}$ is an acyl derivative of lysine or glutamic-acid-bridged acyl derivative of lysine, and $X_{30}$ is Thr, Ala, Ser or absent.

In one embodiment an insulin analogue is provided wherein the A chain comprises a sequence GIVEQ$X_6$CTSI$X_{11}$SLYQLENYCN (SEQ ID NO: 30) and the B chain comprises a sequence FVNQHLCGSHLVEALYLVCGERGFFYTPKT (SEQ ID NO: 4), wherein $X_6$ is selenocysteine and $X_{11}$ is selenocysteine.

In accordance with one embodiment the insulin analogue is a two-chain analogue wherein the A and B chains are joined to one another by two disulfide (S—S) bridges whereas the A chain contains a diselenide (Se—Se) bridge.

In one embodiment an insulin analogue is provided wherein the A chain comprises the sequence GIVEQ$X_6$CTSI$X_{11}$SLYQLENYCN-$R_{53}$ (SEQ ID NO: 30) and the B chain sequence comprises the sequence FVKQ$X_{25}$LCGSHLVEALYLVCGERGFF-$R_{63}$ (SEQ ID NO: 21), or FVNQ$X_{25}$LCGSHLVEALYLVCGERGFF-$R_{63}$ (SEQ ID NO: 20), wherein $X_6$ is selenocysteine;

$X_{11}$ is selenocysteine;

$X_{25}$ is selected from the group consisting of histidine and threonine;

$R_{53}$ is COOH or $CONH_2$; and $R_{63}$ is selected from the group consisting of YT$X_{28}$KT (SEQ ID NO: 22), YTKPT (SEQ ID NO: 23), YT$X_{28}$K (SEQ ID NO: 24), YTKP (SEQ ID NO: 25), YTPK (SEQ ID NO: 26), YT$X_{28}$, YT, Y and a bond, wherein $X_{28}$ is proline, lysine, aspartic acid or glutamic acid. In a further embodiment the A chain comprises the sequence GIVEQ$X_6$CTSI$X_{11}$SLYQLENYCN-$R_{53}$ (SEQ ID NO: 30) as above and the B chain sequence comprises the sequence FVKQ$X_{25}$LCGSHLVEALYLVCGERGFFYTEKT (SEQ ID NO: 28), FVNQ$X_{25}$LCGSHLVEALYLVCGERGFFYTDKT (SEQ ID NO: 27), FVNQ$X_{25}$LCGSHLVEALYLVCGERGFFYTKPT (SEQ ID NO: 29) or FVNQ$X_{25}$LCGSHLVEALYLVCGERGFFYTPKT (SEQ ID NO: 54) wherein $X_{25}$ is selected from the group consisting of histidine and threonine, optionally wherein $X_{25}$ is histidine.

Covalently linkage of a hydrophilic moiety to the insulin analogues disclosed herein provides analogues having slower onset, extended duration and exhibit a basal profile of activity. In one embodiment, the insulin polypeptides disclosed herein are further modified to comprise a hydrophilic moiety covalently linked to the side chain of an amino acid at a position selected from the group consisting of A9, A14 and A15 of the A chain or at the N-terminal alpha amine of the B chain (e.g., at position B1 for an insulin-based B chain) or at the side chain of an amino acid at position B1, B2, B10, B22, B28 or B29 of the B chain. In exemplary embodiments, this hydrophilic moiety is covalently linked to a Lys, Cys, Orn, homocysteine, or acetyl-phenylalanine residue at any of these positions.

Exemplary hydrophilic moieties include polyethylene glycol (PEG), for example, of a molecular weight of about 1,000 Daltons to about 40,000 Daltons, or about 20,000 Daltons to about 40,000 Daltons. Additional suitable hydrophilic moieties include, polypropylene glycol, polyoxyethylated polyols (e.g., POG), polyoxyethylated sorbitol, polyoxyethylated glucose, polyoxyethylated glycerol (POG), polyoxyalkylenes, polyethylene glycol propionaldehyde, copolymers of ethylene glycol/propylene glycol, monomethoxy-polyethylene glycol, mono-(C1-C10)

alkoxy- or aryloxy-polyethylene glycol, carboxymethylcellulose, polyacetals, polyvinyl alcohol (PVA), polyvinyl pyrrolidone, poly-1, 3-dioxolane, poly-1,3,6-trioxane, ethylene/maleic anhydride copolymer, poly (beta-amino acids) (either homopolymers or random copolymers), poly(n-vinyl pyrrolidone)polyethylene glycol, propropylene glycol homopolymers (PPG) and other polyakylene oxides, polypropylene oxide/ethylene oxide copolymers, colonic acids or other polysaccharide polymers, Ficoll or dextran and mixtures thereof.

The hydrophilic moiety, e.g., polyethylene glycol chain in accordance with some embodiments has a molecular weight selected from the range of about 500 to about 40,000 Daltons. In one embodiment the hydrophilic moiety, e.g., PEG, has a molecular weight selected from the range of about 500 to about 5,000 Daltons, or about 1,000 to about 5,000 Daltons. In another embodiment the hydrophilic moiety, e.g., PEG, has a molecular weight of about 10,000 to about 20,000 Daltons. In yet other exemplary embodiment the hydrophilic moiety, e.g., PEG, has a molecular weight of about 20,000 to about 40,000 Daltons. In one embodiment the hydrophilic moiety, e.g., PEG, has a molecular weight of about 20,000 Daltons. In one embodiment an insulin polypeptide is provided wherein one or more amino acids of the analogue are pegylated, and the combined molecular weight of the covalently linked PEG chains is about 20,000 Daltons.

In one embodiment dextrans are used as the hydrophilic moiety. Dextrans are polysaccharide polymers of glucose subunits, predominantly linked by al-6 linkages. Dextran is available in many molecular weight ranges, e.g., about 1 kD to about 100 kD, or from about 5, 10, 15 or 20 kD to about 20, 30, 40, 50, 60, 70, 80 or 90 kD.

Linear or branched polymers are contemplated. Resulting preparations of conjugates may be essentially monodisperse or polydisperse, and may have about 0.5, 0.7, 1, 1.2, 1.5 or 2 polymer moieties per peptide.

In one embodiment the hydrophilic moiety is a polyethylene glycol (PEG) chain, optionally linked to the side chain of an amino acid at a position selected from the group consisting of A9, A14 and A15 of the A chain, positions B1, B2, B10, B22, B28 or B29 of the B chain, at the N-terminal alpha amine of the B chain.

In some embodiments, the insulin analogue is modified to comprise an acyl group. The acyl group can be covalently linked directly to an amino acid of the insulin polypeptide, or indirectly to an amino acid of the insulin polypeptide via a spacer, wherein the spacer is positioned between the amino acid of the insulin polypeptide and the acyl group. The insulin polypeptide may be acylated at the same amino-acid position where a hydrophilic moiety is linked, or at a different amino-acid position. For example, acylation may occur at any position including any amino acid of the A or B chains provided that the activity exhibited by the non-acylated insulin polypeptide is retained upon acylation. Nonlimiting examples include acylation at positions A14 and A15 of the A chain, or positions B10, B22, B28 or B29 of the B chain.

In one specific aspect of the disclosure, the insulin polypeptide (or derivative or conjugate thereof) is modified to comprise an acyl group by direct acylation of an amine, hydroxyl, or thiol of a side chain of an amino acid of the insulin polypeptide. In some embodiments, the insulin polypeptide is directly acylated through the side chain amine, hydroxyl, or thiol of an amino acid. In some embodiments, acylation is at position B28 or B29 (according to the amino-acid numbering of the native insulin A and B chain sequences). In this regard, an insulin polypeptide can be provided that has been modified by one or more amino acid substitutions in the A or B chain sequence, including for example at positions A14, A15, B1, B2, B10, B22, B28 or B29 (according to the amino-acid numbering of the native insulin A and B chain sequences) or at any position of the linking moiety with an amino acid comprising a side chain amine, hydroxyl, or thiol. In some specific embodiments of the disclosure, the direct acylation of the insulin polypeptide occurs through the side chain amine, hydroxyl, or thiol of the amino acid at position B28 or B29 (according to the amino acid numbering of the native insulin A and B chain sequences).

In accordance with one embodiment, the acylated insulin polypeptides comprise a spacer between the peptide and the acyl group. In some embodiments, the insulin polypeptide is covalently bound to the spacer, which is covalently bound to the acyl group. In some exemplary embodiments, the insulin polypeptide is modified to comprise an acyl group by acylation of an amine, hydroxyl, or thiol of a spacer, which spacer is attached to a side chain of an amino acid at position B28 or B29 (according to the amino-acid numbering of the A or B chain of native insulin), or at any position of the spacer moiety. The amino acid of the insulin polypeptide to which the spacer is attached can be any amino acid comprising a moiety which permits linkage to the spacer. For example, an amino acid comprising a side chain —$NH_2$, —OH, or —COOH (e.g., Lys, Orn, Ser, Asp or Glu) is suitable.

In accordance with certain embodiments the bifunctional spacer can be a synthetic or naturally occurring amino acid comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. Each amino acid of the dipeptide or tripeptide spacer attached to the insulin polypeptide can be independently selected from the group consisting of: naturally-occurring and/or non-naturally occurring amino acids, including, for example, any of the D or L isomers of the naturally-occurring amino acids.

The insulin polypeptide can be modified to comprise an acyl group by acylation of a long-chain alkane. In specific aspects, the long-chain alkane comprises an amine, hydroxyl, or thiol group (e.g., octadecylamine, tetradecanol, and hexadecanethiol) which reacts with a carboxyl group, or activated form thereof, of the insulin polypeptide. The carboxyl group, or activated form thereof, of the insulin polypeptide can be part of a side chain of an amino acid (e.g., glutamic acid, aspartic acid) of the insulin polypeptide or can be part of the peptide backbone.

With regard to these aspects of the disclosure, in which a long-chain alkane is acylated by the peptide the insulin polypeptide or the spacer, the long-chain alkane may be of any size and can comprise any length of carbon chain. The long-chain alkane can be linear or branched.

In certain aspects, the long-chain alkane is a $C_4$ to $C_{30}$ alkane. For example, the long-chain alkane can be any of a $C_4$ alkane, $C_6$ alkane, $C_8$ alkane, $C_{10}$ alkane, $C_{12}$ alkane, $C_{14}$ alkane, $C_{16}$ alkane, $C_{18}$ alkane, $C_{20}$ alkane, $C_{22}$ alkane, $C_{24}$ alkane, $C_{26}$ alkane, $C_{28}$ alkane, or a $C_{30}$ alkane. In some embodiments, the long-chain alkane comprises a $C_8$ to $C_{20}$ alkane, e.g., a $C_{14}$ alkane, $C_{16}$ alkane, or a $C_{18}$ alkane.

In accordance with one embodiment a pharmaceutical composition is provided comprising any of the novel insulin dimers disclosed herein, preferably at a purity level of at least 90%, 91%, 92%, 93%, 94%, 95%, 96%, 97%, 98% or 99%, and a pharmaceutically acceptable diluent, carrier or excipient. Such compositions may contain an insulin dimer as disclosed herein at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored contained within various package containers. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

The disclosed insulin analogues are believed to be suitable for any use that has previously been described for insulin peptides. Accordingly, the insulin analogues disclosed herein can be used to treat hyperglycemia, or treat other metabolic diseases that result from high blood-glucose levels. Accordingly, the present disclosure encompasses pharmaceutical compositions comprising an insulin analogues as disclosed herein and a pharmaceutically acceptable carrier for use in treating a patient suffering from high blood-glucose levels. In accordance with one embodiment the patient to be treated using an insulin analogue disclosed herein is a domesticated animal, and in another embodiment the patient to be treated is a human. We also envision that pairwise substitution of $Cys^{A6}$ and $Cys^{A11}$ may be useful in any member of the insulin superfamily (in which these cysteines are invariant) to enhance the efficiency, speed and fidelity of oxidative folding and to stabilize the folded state once obtained; this superfamily includes vertebrate proinsulins, vertebrate insulin-like growth factors (IGF-1 and IGF-2), vertebrate relaxins, and invertebrate insulin-like proteins and analogues thereof.

One method of treating hyperglycemia in accordance with the present disclosure comprises the steps of administering the presently disclosed insulin analogues to a patient using any standard route of administration, including parenterally, such as intravenously, intraperitoneally, subcutaneously or intramuscularly, intrathecally, transdermally, rectally, orally, nasally or by inhalation. In one embodiment the composition is administered subcutaneously or intramuscularly. In one embodiment, the composition is administered parenterally and the insulin polypeptide, or prodrug derivative thereof, is prepackaged in a syringe.

The insulin analogues disclosed herein may be administered alone or in combination with other anti-diabetic agents or anti-obesity agents. Anti-diabetic agents known in the art or under investigation include insulin, leptin, Peptide YY (PYY), Pancreatic Peptide (PP), fibroblast growth factor 21 (FGF21), Y2Y4 receptor agonists, sulfonylureas, such as tolbutamide (Orinase), acetohexamide (DYMELOR®), tolazamide (Tolinase), chlorpropamide (DIABINESE®), glipizide (GLUCOTROL®), glyburide (DIABETA®, MICRONASE®, GLYNASE®), glimepiride (AMARYL®), or gliclazide (Diamicron); meglitinides, such as repaglinide (PRANDIN®) or nateglinide (STARLIX®); biguanides such as metformin (GLUCOPHAGE®) or phenformin; thiazolidinediones such as rosiglitazone (AVANDIA®), pioglitazone (ACTOS®), or troglitazone (Rezulin), or other PPARγ inhibitors; alpha glucosidase inhibitors that inhibit carbohydrate digestion, such as miglitol (GLYSET®), acarbose (PRECOSE®/GLUCOBAY®); exenatide (BYETTA®) or pramlintide; dipeptidyl peptidase-4 (DPP-4) inhibitors such as vildagliptin or sitagliptin; SGLT (sodium-dependent glucose transporter 1) inhibitors; glucokinase activators (GKA); glucagon receptor antagonists (GRA); or FBPase (fructose 1,6-bisphosphatase) inhibitors.

Anti-obesity agents known in the art or under investigation include appetite suppressants, including phenethylamine type stimulants, phentermine (optionally with fenfluramine or dexfenfluramine), diethylpropion (TENUATE®), phendimetrazine (PRELU-2®, BONTRIL®), benzphetamine (DIDREX®), sibutramine (MERIDIA®, REDUCTIL®); rimonabant (ACOMPLIA®), other cannabinoid receptor antagonists; oxyntomodulin; fluoxetine hydrochloride (PROZAC®); Qnexa (topiramate and phentermine), EXCALIA® (bupropion and zonisamide) or CONTRAVE® (bupropion and naltrexone); or lipase inhibitors, similar to XENICAL (Orlistat) or Cetilistat (also known as ATL-962), or GT 389-255.

Pharmaceutical compositions comprising the insulin analogues disclosed herein can be formulated and administered to patients using standard pharmaceutically acceptable carriers and routes of administration known to those skilled in the art. Accordingly, the present disclosure also encompasses pharmaceutical compositions comprising one or more of the insulin analogues disclosed herein (or prodrug derivative thereof), or a pharmaceutically acceptable salt thereof, in combination with a pharmaceutically acceptable carrier. In one embodiment the pharmaceutical composition comprises a 1 mg/ml concentration of the insulin analogue at a pH of about 4.0 to about 7.0 in a phosphate buffer system. The pharmaceutical compositions may comprise the insulin analogue as the sole pharmaceutically active component, or the insulin analogue can be combined with one or more additional active agents.

In one embodiment a kit is provided with a device for administering an insulin analogue composition to a patient. The kit may further include a variety of containers, e.g., vials, tubes, bottles, and the like. Preferably, the kits will also include instructions for use. In another embodiment the kit comprises a syringe and a needle, and in one embodiment the insulin analogue composition is prepackaged within the syringe.

The compounds of this disclosure may be prepared by standard synthetic methods, recombinant DNA techniques, or any other methods of preparing peptides and fusion proteins. Although certain non-natural amino acids cannot be expressed by standard recombinant DNA techniques, techniques for their preparation are known in the art. Compounds of this disclosure that encompass non-peptide portions may be synthesized by standard organic-chemistry reactions, in addition to standard peptide-chemistry reactions when applicable.

In accordance with embodiment 1 an insulin analogue comprising an insulin A chain and an insulin B chain is provided wherein said A chain comprises a sequence of $GIVX_4X_8X_6CX_8X_9X_{10}X_{11}X_{12}LX_{14}X_{15}LX_{17}X_{18}YCX_{21}$—$R_{53}$ (SEQ ID NO: 10), and said B chain comprises a sequence $R_{62}$-$X_{25}LCGX_{29}X_{30}LVX_{33}X_{34}LYLVCGX_{41}X_{42}GFX_{45}$ (SEQ ID NO: 11), wherein $X_4$ is glutamic acid or aspartic acid; $X_5$ is glutamine or glutamic acid; $X_6$ is selenocysteine; $X_8$ is histidine, threonine, lysine, arginine, tryptophan or phenylalanine; $X_9$ is serine, arginine, lysine, ornithine or alanine; $X_{10}$ is isoleucine or serine; $X_{11}$ is selenocysteine; $X_{12}$ is serine or aspartic acid; $X_{14}$ is tyrosine, arginine, lysine, ornithine or alanine; $X_{15}$ is glutamine, glutamic acid, arginine, alanine, lysine, ornithine or leucine; $X_{17}$ is glutamic acid, aspartic acid, asparagine, lysine, ornithine or glutamine; $X_{18}$ is methionine, asparagine, glutamine, aspartic acid, glutamic acid or threonine; $X_{21}$ is selected from the group consisting of alanine, glycine, serine, valine, threonine, isoleucine, leucine, glutamine, glutamic acid, asparagine, aspartic acid, histidine, tryptophan, tyrosine, and methionine; $X_{25}$ is histidine or threonine; $X_{29}$ is selected from the group consisting of alanine, glycine and serine; $X_{30}$ is selected from the group consisting of histidine, aspartic acid, glutamic acid, homocysteic acid and cysteic acid; $X_{33}$ is selected from the group consisting of aspartic acid and glutamic acid; $X_{34}$ is selected from the group consisting of alanine and threonine; $X_{41}$ is selected from the group consisting of glutamic acid, aspartic acid and asparagine; $X_{42}$ is selected from the group consisting of alanine, ornithine, lysine and arginine; $X_{45}$ is tyrosine or phenylalanine; $R_{62}$ is selected from the group consisting of AYRPSE (SEQ ID NO: 12), FVNQ (SEQ ID NO: 13), PGPE (SEQ ID NO: 14), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal amine; and $R_{53}$ is COOH or $CONH_2$, wherein a diselenide bridge is formed between the side chains of residues A6 and A11.

In embodiment 2 an insulin analogue of embodiment 1 is provided wherein $X_4$ is glutamic acid or aspartic acid; $X_5$ is glutamine or glutamic acid; $X_6$ is selenocysteine; $X_8$ is histidine, threonine or phenylalanine; $X_9$ is serine or arginine; $X_{10}$ is isoleucine or serine; $X_{11}$ is selenocysteine; $X_{12}$ is serine or aspartic acid; $X_{14}$ is tyrosine, arginine or alanine; $X_{15}$ is glutamine, arginine, or leucine; $X_{17}$ is glutamic acid or aspartic acid; $X_{18}$ is methionine, asparagine or threonine; $X_{21}$ is selected from the group consisting of alanine, glycine and asparagine; $X_{25}$ is histidine or threonine; $X_{29}$ is selected from the group consisting of alanine, glycine and serine; $X_{30}$ is selected from the group consisting of histidine, aspartic acid and glutamic acid; $X_{33}$ is selected from the group consisting of aspartic acid and glutamic acid; $X_{34}$ is selected from the group consisting of alanine and threonine; $X_{41}$ is selected from the group consisting of glutamic acid and aspartic acid; $X_{42}$ is arginine; and $X_{45}$ is tyrosine or phenylalanine.

In embodiment 3 an insulin analogue any one of embodiments 1-2 is provided wherein said A chain comprises the sequence GIVEQ$X_6$C$X_8$SI$X_{11}$SLYQLENYC$X_{21}$-$R_{53}$ (SEQ ID NO: 15), wherein $X_6$ is seleno-cysteine; $X_8$ is histidine, threonine, lysine, arginine, or tryptophan; $X_{11}$ is selenocysteine; and $X_{21}$ is selected from the group consisting of alanine, glycine, serine, threonine, glutamine, asparagine, and aspartic acid.

In embodiment 4 an insulin analogue any one of embodiments 1-3 is provided wherein said B chain comprises the sequence FV$X_{23}$Q$X_{25}$LCGSHLVEALYLVCGERGFF-YT$X_{48}$X$X_{50}$ (SEQ ID NO: 16), wherein $X_{23}$ is Asn or Lys:

$X_{25}$ is histidine or threonine;

$X_{48}$ is proline, lysine or aspartic acid;

$X_{49}$ is proline, lysine or glycine;

$X_{50}$ is threonine, alanine or serine; and $R_{53}$ is COOH or $CONH_2$.

In embodiment 5 an insulin analogue any one of embodiments 1-4 is provided wherein said A chain comprises the sequence GIVEQ$X_6$C$X_8$$X_9$I$X_{11}$SLYQLENYC$X_{21}$-$R_{53}$ (SEQ ID NO: 17, and said B chain comprises the sequence FV$X_{23}$Q$X_{25}$LCG$X_{29}$$X_{30}$LV$X_{33}$$X_{34}$LYLVCG$X_{41}$$X_{42}$GF$X_{45}$ (SEQ ID NO: 18), wherein $X_6$ is selenocysteine; $X_8$ is histidine or threonine; $X_9$ is serine, lysine, or alanine; $X_{11}$ is selenocysteine; $X_{21}$ is alanine, glycine or asparagine; $X_{23}$ is asparagine or lysine;

$X_{25}$ is histidine or threonine; $X_{29}$ is selected from the group consisting of alanine, glycine and serine; $X_{30}$ is selected from the group consisting of histidine, aspartic acid, glutamic acid, homocysteic acid and cysteic acid; $X_{33}$ is selected from the group consisting of aspartic acid and glutamic acid; $X_{34}$ is selected from the group consisting of alanine and threonine; $X_{41}$ is selected from the group consisting of glutamic acid, aspartic acid and asparagine; $X_{42}$ is selected from the group consisting of alanine, ornithine, lysine and arginine; $X_{45}$ is tyrosine or phenylalanine; and $R_{53}$ is COOH or $CONH_2$.

In embodiment 6 an insulin analogue any one of embodiments 1-3 or 5 is provided wherein the B chain sequence comprises the sequence FVKQ$X_{25}$LCGSHLVEALYL-VCGERGFF-$R_{63}$ (SEQ ID NO: 21), or FVNQ$X_{25}$LC-GSHLVEALYLVCGERGFF-$R_{63}$ (SEQ ID NO: 20), wherein $X_{25}$ is selected from the group consisting of histidine and threonine; and $R_{63}$ is selected from the group consisting of YT$X_{28}$KT (SEQ ID NO: 22), YTKPT (SEQ ID NO: 23), YT$X_{28}$K (SEQ ID NO: 24), YTKP (SEQ ID NO: 25), YTPK (SEQ ID NO: 26), YT$X_{28}$, YT, Y and a bond, wherein $X_{28}$ is proline, lysine, aspartic acid or glutamic acid.

In embodiment 7 an insulin analogue any one of embodiments 1-6 is provided wherein the B chain sequence comprises the sequence FVKQ$X_{25}$LCGSHLVEALYLV-CGERGFFYTEKT (SEQ ID NO: 28), FVNQ$X_{25}$LC-GSHLVEALYLVCGERGFFYTDKT (SEQ ID NO: 27), FVNQ$X_{25}$LCGSHLVEALYLVCGERGFFYTKPT (SEQ ID NO: 29) or FVNQ$X_{25}$LCGSHLVEALYLVCGERG-FFYTPKT wherein $X_{25}$ is selected from the group consisting of histidine and threonine.

In embodiment 8 an insulin analogue any one of embodiments 1-7 is provided wherein $X_{25}$ is histidine.

In embodiment 9 an insulin analogue any one of embodiments 1-8 is provided wherein the A chain is an amino-acid sequence consisting of GIVEQ$X_6$CTSI$X_{11}$SLYQLENYCN-$R_{53}$ (SEQ ID NO: 30) and the B chain comprises the sequence FVNQHLCGSHLVEALYLVCGERGFFYTPKT (SEQ ID NO: 4), wherein $X_6$ is selenocysteine;

$X_{11}$ is selenocysteine and $R_{53}$ is COOH or $CONH_2$.

In embodiment 10 an insulin analogue any one of embodiments 1-9 is provided wherein said A chain comprises the sequence GIVEQ$X_6$CTSI$X_{11}$SLYQLENYCN (SEQ ID NO: 30) and said B chain comprises the sequence FVNQHLCGSHLVEALYLVCGERGFFYTPKT (SEQ ID NO: 4), wherein $X_6$ is selenocysteine and $X_{11}$ is selenocysteine.

In embodiment 11 an insulin analogue any one of embodiments 1-10 is provided wherein said A chain comprises the sequence GIVEQ$X_6$CTSI$X_{11}$SLYQLENYCN-$R_{53}$ (SEQ ID NO: 30) and said B chain comprises the sequence FVKQ$X_{25}$LCGSHLVEALYLVCGERGFFYTEKT (SEQ ID NO: 28) or FVNQ$X_{25}$LCGSHLVEALYLVCGERGF-FYTKPT (SEQ ID NO: 29), wherein $X_{25}$ is histidine; and $R_{53}$ is COOH or $CONH_2$.

In embodiment 12 an insulin analogue any one of embodiments 1-11 is provided wherein a hydrophilic moiety is covalently linked at one or more positions corresponding to A14, A15, B0, B1, B10, B22, B28, B29, optionally wherein the hydrophilic moiety is a polyethylene glycol.

In embodiment 13 an insulin analogue any one of embodiments 1-12 is provided, further comprising an acyl group or alkyl group covalently linked to an amino-acid side chain of said insulin analog, optionally wherein said acyl group or alkyl group is covalently linked to one or more positions selected from A14, A15, B0, B1, B10, B22, B28, B29 of the insulin peptide.

In embodiment 14 two or more insulin analogues any one of embodiments 1-13 are covalently linked to one another to form a dimer or multimer.

In embodiment 15 a pharmaceutical composition is provided comprising an insulin analogue any one of embodiments 1-14, or pharmaceutically acceptable salt thereof, and a pharmaceutically acceptable carrier.

In embodiment 16 a method of treating diabetes is provided, said method comprising administering an effective amount of a pharmaceutical composition of embodiment 15.

In embodiment 17, a pharmaceutical composition is provided comprising an insulin analogue of any one of embodiments 1-14, or pharmaceutically acceptable salt thereof and an excipient selected from the group consisting of triphosphate ions, trisulphate ions, and chelating agents, including (but not limited to) ethylene-diamine-tetra-acetic acid (EDTA) and ethylene glycol-bis(O-aminoethyl ether)-N,N,N',N'-tetraacetic acid (EGTA) and a pharmaceutically acceptable carrier.

Example 1

Synthesis of [C6U, C11U]-Substituted Human Insulin

In brief, the 21-residue peptide GIVEQ$X_6$CTSI$X_{11}$ SLYQLENYCN-$R_{53}$ (SEQ ID NO: 31), wherein $X_6$ and $X_{11}$ are each Se (denoted Chain A[C6U, C11U]) was prepared using an automated peptide synthesizer (CS136XT, CS Bio Inc. CA) on a 0.25 mmol scale using Fmoc-Asn(Trt)-TentaGel®R PHB resin (loading of 0.17 mmol/g). Fmoc-amino acids (2 mmol in 5 mL DMF) activated with HCTU (2 mmol in 5 mL DMF) and DIEA (4 mmol in 5 mL DMF) for 5 min and allowed to couple for 25 min, with constant shaking. Fmoc-deprotection was carried out with 20% piperidine in DMF (2×5 min). Fmoc-Sec(Mob)-OH was manually coupled for two hours using DIC/OxymaPure activation method (2.9 equiv/3.0 equiv respectively). The peptide-resin was then washed with DMF, DCM and dried under vacuum. The dried peptide-resin was cleaved in the presence of 2 equivalents of DTNP, using a TFA:water:thioanisole:triisopropylsilane:ethanedithiol (92.5:1.5:1.5:1.5:1.5) cocktail for 4 h. The cleavage mixture was filtered and TFA was evaporated with $N_2$ bubbling to minimum volume, to which 8-fold volume of cold ether was added dropwise. The precipitated crude peptide was centrifuged (5000 rpm, 10 min), ether was removed and the crude peptide dissolved in ACN-water (1:1) containing 0.1% TFA and was further diluted to ~25% ACN with water and lyophilized, giving 208 mg of crude material. The crude peptide were dissolved in 25% ACN in water containing 0.1% TFA and purified by multiple injections of 100 mg each using prep RP-HPLC (XSelect C18 column, 5 μm, 30×250 mm) using a gradient of 25%-50% B over 50 min; this step provided 49 mg of chain A[C6U, C11U] analogue (8% yield, based on resin loading). The product was characterized by UPLC using ACQUITY UPLC XSelect C18 column (3.5 μm, 130 Å, 4.6×150 mm), and a gradient of 5% B over 2 min then 5-70% B over 20 min and ESI-MS.

Analytical reverse-phase HPLC (rp-HPLC) was performed using a Waters UPLC H-Class or Waters Alliance HPLC with 220 nm UV detection using a XSelect C18 column (3.5 μm, 130 Å, 4.6×150 mm) or XBridge BEH300 C4 (3.5 μm, 130 Å, 4.6×150 mm). Preparative and semi-preparative rp-HPLC was performed on a Waters LCQ150 system using a XBridge C8 column (5 μm, 10×150 mm) or XSelect C18 column (5 μm, 130 Å, 30×250 mm). Linear gradients of ACN (with 0.1% TFA, eluent B) in water (with 0.1% TFA, eluent A) were used for all systems to elute bound peptides. The flow rates were 1 mL/min (analytical), 3.35 mL/min (Semi-preparative), and 20 mL/min (preparative). ESI-MS was performed on LCQ Fleet Ion Trap mass spectrometer (Thermo Scientific). Peptide masses were calculated from the experimental mass to charge (m/z) ratios from the observed multiply charged species of a peptide. The HR-MS were recorded on a Q-ExactivePlus Orbitrap mass spectrometer (Thermo Scientific) with a ESI source and 140'000 FWHM, in a method with AGC target set to 1E6, and scan range was 400-2800 m/z. Deconvolution of the raw experimental MS data was performed with the help of MagTran v1.03 software.

A solution of chain A[C6U, C11U] analogue (3.5 mg) was dissolved in a glycine buffer (0.1 M, pH 10.6) and mixed with a solution of sulfitolized chain B (4.85 mg). The final concentration of each chain was 1.2 mM in the same buffer. To initiate chain combination, DTT was added in quantity stoichiometric to the concentration of S-sulfonate groups (2.4 mM in this case). The reaction was carried out at 4° C. with open sample reaction to permit air oxidation. To control the reaction progress, small aliquots (10 μL) were taken from the reaction solution, quenched by addition of water containing 0.1% TFA (15 μL) and analyzed by injecting 20 μL of the sample onto the analytical rp-HPLC (XSelect C4 column, 3.5 μm, 130 Å, 4.6×150 mm); the HPLC protocol employed a gradient of 5% eluent B in eluent A for 1 min then 5-70% eluent B over 21 min, with detection at 220 nm. At the end of the recombination reaction, the Se-insulin [C6$U^A$, C11$U^A$] was isolated through a XBridge BEH300 analytical C4 column (3.5 μm, 130 Å, 4.6×150 mm) and lyophilized to yield 31% (2.6 mg) based on the amounts of the chains used.

TABLE 1

Summary of [C6U, C11U] Insulin Analogues (Example 2)

| parent analogue | [C6U, C11U]-modified analogue |
|---|---|
| insulin lispro | [$Sec^{A6}$, $Sec^{A11}$, $Lys^{B28}$, $Pro^{B29}$]-insulin |
| insulin glulisine | [$Sec^{A6}$, $Sec^{A11}$, $Lys^{B3}$, $Glu^{B29}$]-insulin |
| insulin aspart | [$Sec^{A6}$, $Sec^{A11}$, $Asp^{B28}$]-insulin |
| insulin glargine | [$Sec^{A6}$, $Sec^{A11}$, $Gly^{A21}$, $Arg^{B31}$, $Arg^{B32}$]-insulin |
| insulin lispro analogue 1 | [$Sec^{A6}$, $Sec^{A11}$, $His^{A8}$, $Lys^{B28}$, $Pro^{B29}$]-insulin |
| insulin lispro analogue 2 | [$Sec^{A6}$, $Sec^{A11}$, $Glu^{A14}$, $Lys^{B28}$, $Pro^{B29}$]-insulin |
| insulin lispro analogue 3 | $Sec^{A6}$, $Sec^{A11}$, $His^{A8}$, $Glu^{A14}$, $Lys^{B28}$, $Pro^{B29}$]-insulin |
| insulin lispro analogue 4 | [$Sec^{A6}$, $Sec^{A11}$, $Asp^{B10}$, $Lys^{B28}$, $Pro^{B29}$]-insulin |

Example 2

[C6U, C11U] Insulin Analogues

Eight insulin analogues containing [C6U, C11U](and so containing a diselenide bridge between positions A6 and A11) were prepared to exemplify the compatibility and utility of this bridge with standard amino-acid substitutions known in the art to alter the PK/PD properties of insulin or to augment its stability. These analogues are listed in Table 1. The first four represent [C6U, C11U]-reinforced versions of insulin analogues in current clinical use for the treatment of DM (insulins lispro, glulisine, aspart and glargine); the remaining four were prepared to investigate whether the gain in stability conferred by the A6-A11 diselenide bridge would be additive to mechanisms of stabilization known in the art to be conferred by standard amino-acid substitutions as exemplified by $His^{A8}$, $Gu^{A14}$ and $Asp^{B10}$. Each of these eight insulin analogues was mono-component as evaluated by analytical reversal-phase HPLC and exhibited its predicted mass as evaluated by mass spectrometry. Native-like folding was in each case verified by far ultra-violet circular dichroism (CD).

An analogue of insulin lispro containing pairwise substitution of $Cys^{A6}$ and $Cys^{A11}$ by $Sec^{A6}$ and $Sec^{A11}$ was prepared essentially as described in Example 1, except that the WT B chain (obtained from commercial insulin) was replaced by a synthetic analogue containing the paired substitutions $Pro^{B28}$→Lys and $Lys^{B29}$→Pro. Technical differences pertained to instrumentation. LC-MS analyses were performed on LCQ Advantage Ion Trap Mass Spectrometer System coupled with Agilent 1100 Series HPLC system. Analytical rp-HPLC was performed using a Waters 1525 Binary HPLC system. All chromatographic separations were performed on a C8 Proto (4.6×250 mm) 300 Å, 5 μm, Higgins Analytical Inc. column, using 25-50% Solvent B in Solvent A over 35 minutes (solvent A=0.1% TFA in water, solvent B=0.1% TFA in acetonitrile) at a flow rate of 1.0 mL/min with detection by UV absorption at 215 nm. Preparative rp-HPLC employed the Waters 2545 Quaternary pumping system equipped with FlexInject.

As described in detail below, the [$C6U^{A}$, $C11U^{A}$] analogue of insulin lispro exhibited native-like structure and function with enhanced stability (relative to insulin lispro).

The second approach was designed to exploit a 48-residue single-chain insulin (SCI) precursor, prepared by an automated solid-phase peptide synthesizer (Tribute 2-Channel peptide synthesizer using 6C1-HOBt/DIC mediated coupling protocols). The synthetic protocol was as described by DiMarchi and colleagues (Zykov, A. N., et al. (2014) *ACS Chem. Biol.* 9, 683-91). Residues 1-28 of SCI precursor corresponded to insulin B-chain residues B1-B28, except that residue 28 was Lys instead of Pro; this Lysine (unique in the SCI sequence) provided a specific cleavage site for Endo-Lys C. Residues 29-48 of the SCI precursor corresponded to A-chain residues A1-21; the critical $Sec^{A6}$ and $Sec^{A11}$ substitutions thus were placed at peptide residues 34 and 39 in the SCI precursor. The reduced polypeptide underwent oxidative folding to form the A6-A11 diselende bond and cystines A7-B7 and B20-A19 essentially as described by Zykov, A. N., et al. (2014).

The folded SCI analogue was digested with trypsin to liberate a large fragment, designated des-octapeptide[B23-B30]-insulin-A[C6U, C11U]; DOI-A[C6U, C11U]. This fragment thus contained a truncated B-chain fragment (residues B1-B22) and intact A-chain analogue (A[$C6U^{A}$, $C11U^{A}$] as above). The two native disulfide bridges and novel A6-A11 diselenide bridge were contained within this fragment. An octapeptide of sequence Gly-Phe-Phe-Tyr-Thr-Lys-Pro-Thr was in parallel prepared by automated peptide synthesis. The desired analogue of insulin lispro containing a A6-A11 diselenide bridge will then be obtained by trypsin-mediated semi-synthesis as described (Kubiac, T. and Cowburn, D. (1986) *Int. J. Pept. Protein Res.* 27, 514-21). In brief, the formation of a peptide bond between $Arg^{B22}$ and the synthetic octapeptide will be mediated by trypsin (in a mixed solvent system containing 1,4-butanediol and dimethylacetamide). Insulin analogues will be purified by preparative C4 rp-HPLC (Higgins Analytical Inc, Proto 300 C4 10 μM, 250×20 mm), and their purity assessed by analytical rp-C4 HPLC (Higgins C4 5 μM, 250×4.6 mm). Molecular masses of purified intermediates and analogues were verified using mass spectrometry as above.

An analogue of insulin glulisine likewise containing pairwise substitution of $Cys^{A6}$ and $Cys^{A11}$ by $Sec^{A6}$ and $Sec^{A11}$ was prepared by chain combination essentially as described above in Example 2, except that the WT B chain (obtained from commercial insulin) was replaced by a synthetic analogue containing the paired substitutions $Asn^{B3}$→Lys and $Lys^{B29}$→Glu. A control analogue with native disulfide bridges was also prepared by chemical synthesis and chain combination.

An analogue of insulin aspart likewise containing pairwise substitution of $Cys^{A6}$ and $Cys^{A11}$ by $Sec^{A6}$ and $Sec^{A11}$ was prepared by chain combination essentially as described above in Example 2, except that the WT B chain (obtained from commercial insulin) was replaced by a synthetic analogue containing the paired substitutions $Pro^{B28}$→Asp. A control analogue with native disulfide bridges was also prepared by chemical synthesis and chain combination.

An analogue of insulin glargine likewise containing pairwise substitution of $Cys^{A6}$ and $Cys^{A11}$ by $Sec^{A6}$ and $Sec^{A11}$ was prepared by chain combination by a modified procedure. The reaction employed a variant [$Sec^{A6}$, $Sec^{A11}$, $Glu^{A21}$]A chain and variant B chain containing C-terminal extension $Arg^{B31}$-$Arg^{B32}$. Under the "standard" reaction conditions above, the yield was about threefold lower than that of chain combination reactions with the WT B chain, presumably due to the $Arg^{B31}$-$Arg^{B32}$ extension, which shifts the isoelectric point of the peptide and so its pH-dependent solubility. This effect was largely mitigated by raising the pH of the reaction from pH 10.6 to 11.2 (which enhanced the solubility of the variant B chain) and by extending the reaction time; in addition, the synthetic [$C6U^{A}$, $C11U^{A}$]-modified A chain was pre-dialyzed to remove ammonium salts prior to its use in the chain-combination reaction. This modified protocol enabled the efficiency of chain combination to be almost as high as was observed in the preparation of [$C6U^{A}$, $C11U^{A}$]-modified WT insulin. A control analogue with native disulfide bridges (i.e., native insulin glargine) was obtained from commercial sources.

Four additional analogues of insulin lispro likewise containing pairwise substitution of $Cys^{A6}$ and $Cys^{A11}$ by Sec and further modified by either substitution $Thr^{A}$→His, substitution $Tyr^{A14}$→Glu, paired substitutions [$Thr^{A8}$→His, $Tyr^{A14}$→Glu], or $His^{B10}$→Asp were prepared by chain combination essentially as described in Example 1 and listed in Table 1. Each of these four analogues of [C6U, C11U]-modified insulin lispro thus contains additional standard amino-acid substitutions that are known in the art to augment the thermodynamic stability of insulin.

Example 3

Characterization of [$C6U^{A}$, $C11U^{A}$] Insulin Analogues

Figure 7:
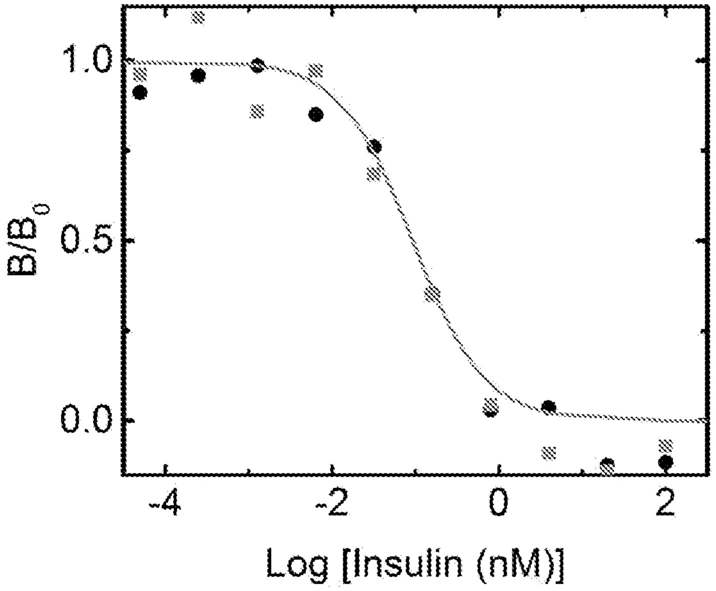
FIG. 7 illustrates a receptor-binding assay for insulin receptor (IR) based on competitive displacement of prebound $^{125}I$-$Tyr^{A14}$-human insulin. The IR-binding affinity of the Se-insulin analogue (Se-insulin[$C6U^A$, $C11U^A$], ■) was indistinguished from the affinity of a semisynthetic version of WT-insulin ($Orn^{B29}$-insulin, ●). Modeling yielded the estimate $K_d$=0.08±0.02 nM.

Receptor-Binding Affinities. Affinities of insulin or insulin analogues for the lectin-purified insulin receptor were evaluated using a microtiter plate antibody assay; representative studies of the [$C6U^{A}$, $C11U^{A}$] analogue of WT human insulin (Example 1 and 2 above) are shown in FIG. 7 in relation to $Orn^{B29}$-human insulin, a conservative analogue of human insulin. The assay exploited competitive displacement of $^{125}$I-Tyr$^{A14}$-insulin. Data were corrected for nonspecific binding (amount of radioactivity remaining membrane associated in the presence of 1 μM human insulin. Microtiter strip plates (Nunc Maxisorb) were incubated overnight at 4° C. with AU5 IgG (100 μl/well of 40 mg/ml in phosphate-buffered saline). Binding data were analyzed by a two-site sequential model. Binding data were analyzed by non-linear regression using a heterologous competition model (Wang, Z. X. (1995) *FEBS Lett.* 360, 111-114) to obtain dissociation constants. In all assays the percentage of tracer bound in the absence of competing ligand was less than 15% to avoid ligand-depletion artifacts.

The affinities of the two insulin analogues containing paired Sec$^{A6}$ and Sec$^{A11}$ substitutions were indistinguishable from that of WT insulin or insulin lispro (see FIG. 7). Similar results were obtained on comparison of insulin glulisine versus insulin [C6U, C11U]-modified glulisine and on comparison of insulin aspart versus insulin [C6U, C11U]-modified aspart.

Figure 8A:
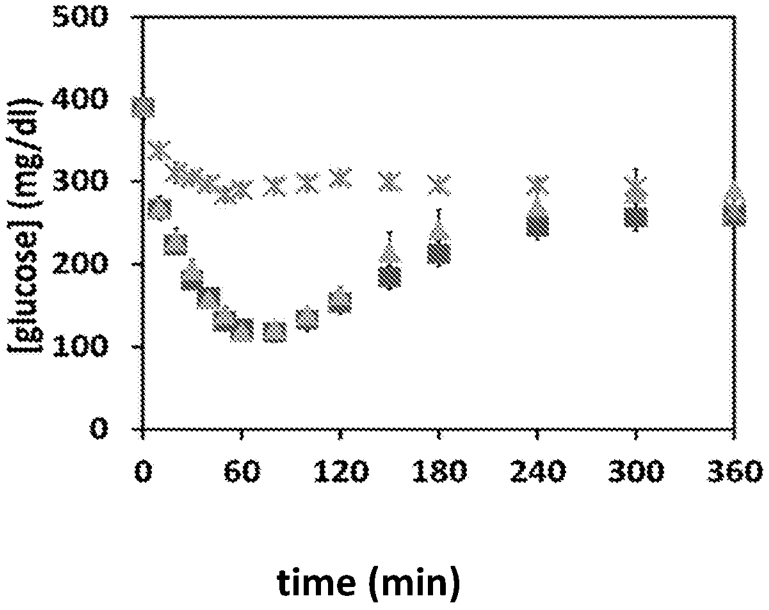
FIG. 8A-8E are graphs presenting data for insulin analogues.
Figure 8B:
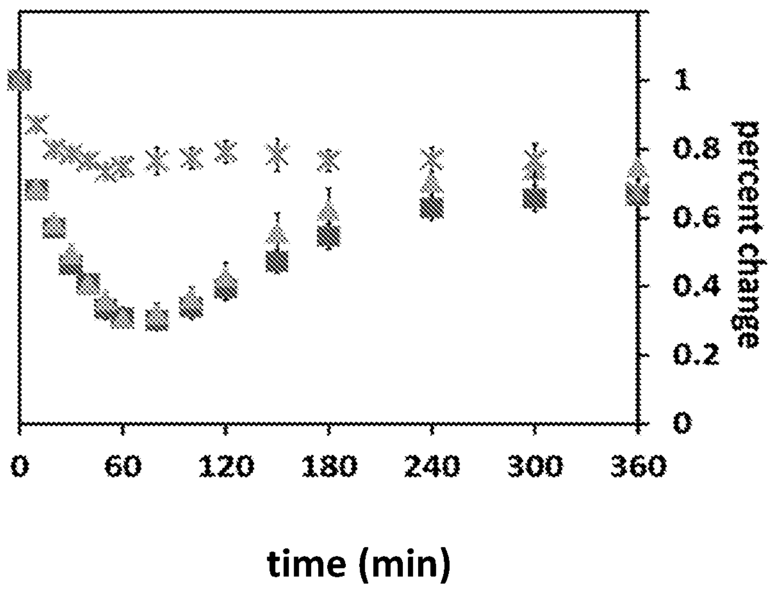

Potency in Diabetic Rats. The biological activities of insulin or insulin analogues were evaluated in Sprague-Dawley rats rendered diabetic through the action of beta-cell poison streptozotocin as described (Yang, Y., et al. (2010) *J. Biol. Chem.* 285: 10806-21). The rats exhibited a mean body mass of ca. 300 grams and a mean level of glycemia of ca. 400 mg/dL. Representative studies of the [C6U$^{A}$, C11U$^{A}$] analogue of insulin lispro (Example 2 above) are shown in FIGS. 8A & 8B in relation to insulin lispro; their potencies (evaluated as the ability to reduce the blood-glucose concentration on subcutaneous injection) were indistinguishable. Similar results were obtained on comparative rat studies of insulin glulisine versus insulin [C6U, C11U]-modified glulisine and on comparison of insulin aspart versus insulin [C6U, C11U]-modified aspart.

Figure 8C:
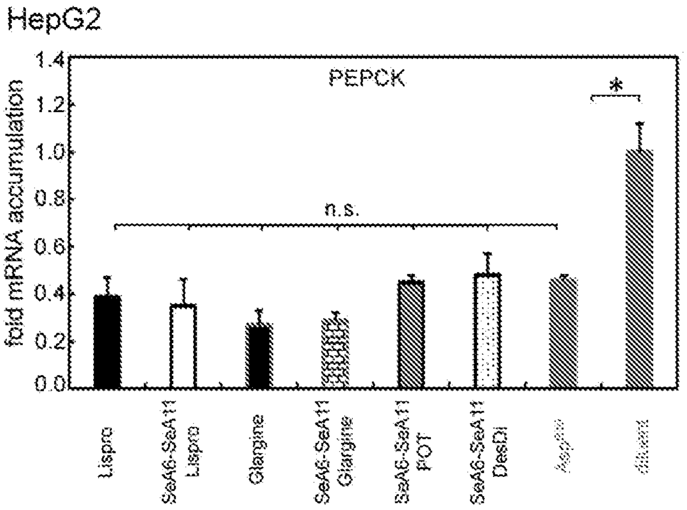
Figure 8D:
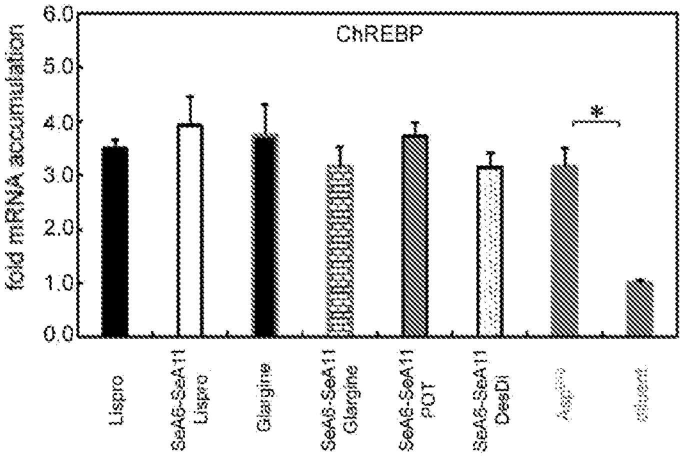
Figure 8E:
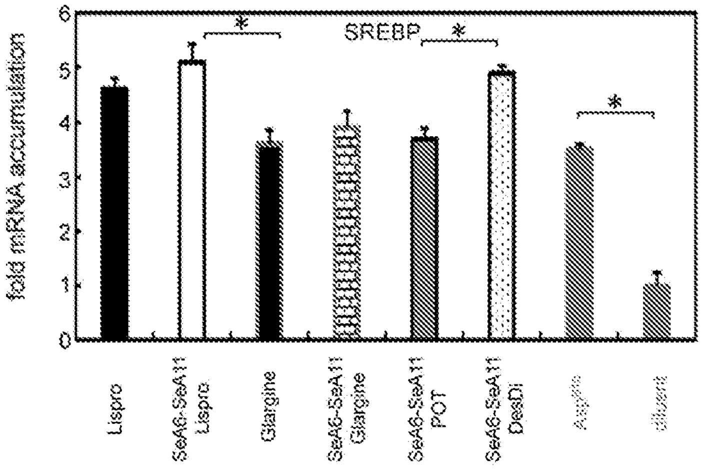

The biological activities of representative insulin analogues in current clinical use were further evaluated in a human liver-derived cell line, HepG2 (hepatoma), chosen as a cell-culture model of the insulin-regulated signaling pathways in the liver. An assay of gene expression (quantitative real-time reverse-transcriptase polymerase chain reaction; q-RT-rtPCR) was employed to probe how the binding of insulin analogues to insulin receptors on the surface of these cells might alter the accumulation of mRNAs respectively encoding a key enzyme in the pathway of glucogeneosis (PEPCK) and key regulatory factors in the pathway of cholesterol or lipid synthesis (ChREBP and SREBP). In these assays the transcriptional regulatory activities of [C6U, C11U]-modified insulin lispro were indistinguishable from those of native insulin lispro, and similarly the transcriptional regulatory activities of [C6U, C11U]-modified insulin glargine were indistinguishable from those of native insulin glargine (FIGS. 8C-8E).

Figure 9A:
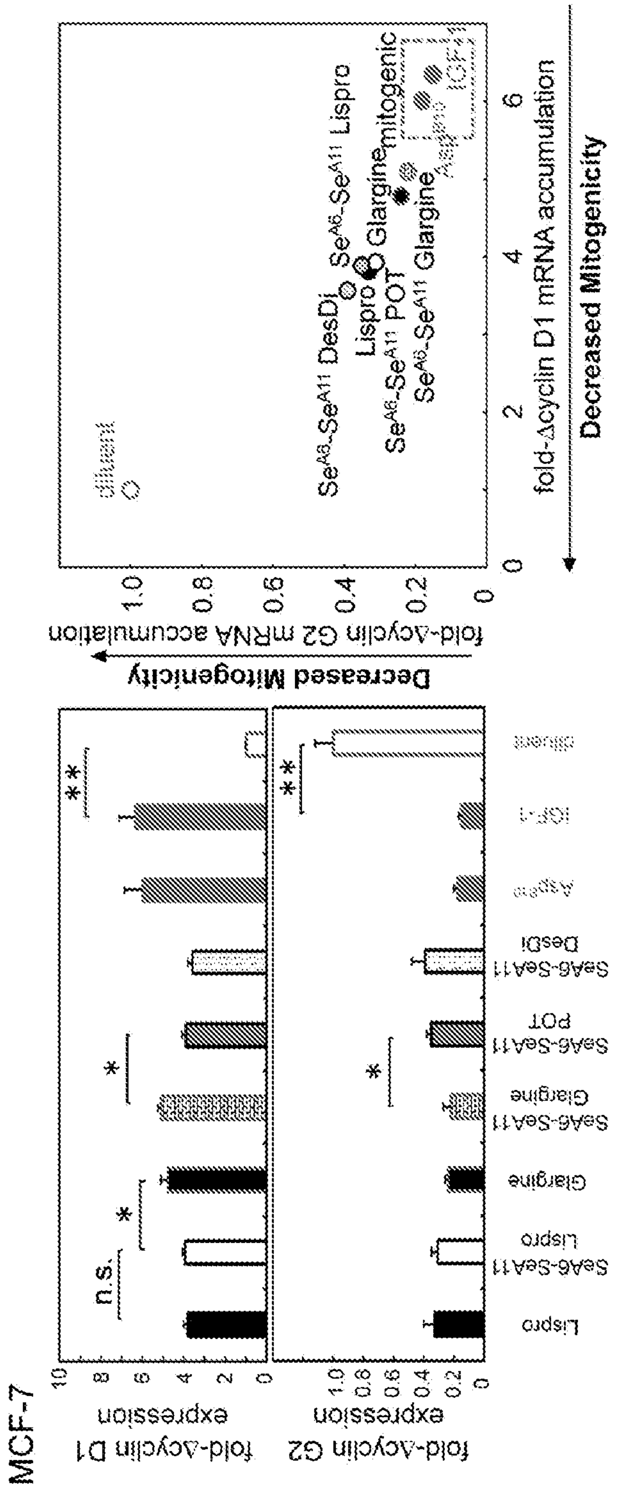
FIGS. 9A & 9B document responses of insulin analogues in cell proliferation and insulin receptor signaling in human breast-cancer cell line MCF-7.

Mitogenicity. An undesirable biological activity of an insulin analogue would be any increase in mitogenicity relative to WT insulin. Enhanced mitogenicity in the case of Asp$^{B10}$-insulin is known in the art to be associated with an excess of mammary tumors on long-term treatment of rats (Hansen, B. F., et al. (2011) *Diabetologia* 54: 2226-31). An assay for relative mitogenicity among insulin analogues is provided by transcriptional signaling leading to reciprocal regulation of the genes encoding cyclin D1 and cyclin G2 (Glidden, M. D., et al. (2018) *J. Biol. Chem.* 293: 47-68). As in the above studies of HepG2 cells in culture, an analogous q-RT-rtPCR assay was performed to probe mRNA accumulation in human breast-cancer cell line MCF-7; this cell line expresses the Type 1 IGF receptor (IGF-1R) as well as IR-A and IR-B. In this assay the signature of a mitogenic protein was provided by IGF-1 and Asp$^{B10}$-insulin. Treatment of MCF-7 cells with these proteins stimulates cyclin D1 transcription and inhibits cyclin G2 transception to a more marked extent than does treatment with insulin lispro or Orn$^{B29}$-insulin (the latter contains conservative substitution Lys$^{B29}$→Orn and so provides a model of WT insulin). Results are summarized in gene-specific histograms (FIG. 9A, left) and are highlighted in a two-dimensional map (FIG. 9A, right). In these assays the mitogenic signature of [C6U, C11U]-modified insulin lispro was indistinguishable from that of native insulin lispro, and similarly the mitogenic signature of [C6U, C11U]-modified insulin glargine was indistinguishable from that of native insulin glargine. We note in passing that the glargine signature in both dimensions (cyclin D1 activation and cyclin G2 repression) is intermediate between insulin lispro or Orn$^{B29}$-insulin and Asp$^{B10}$-insulin as is known in the art.

Figure 9B:
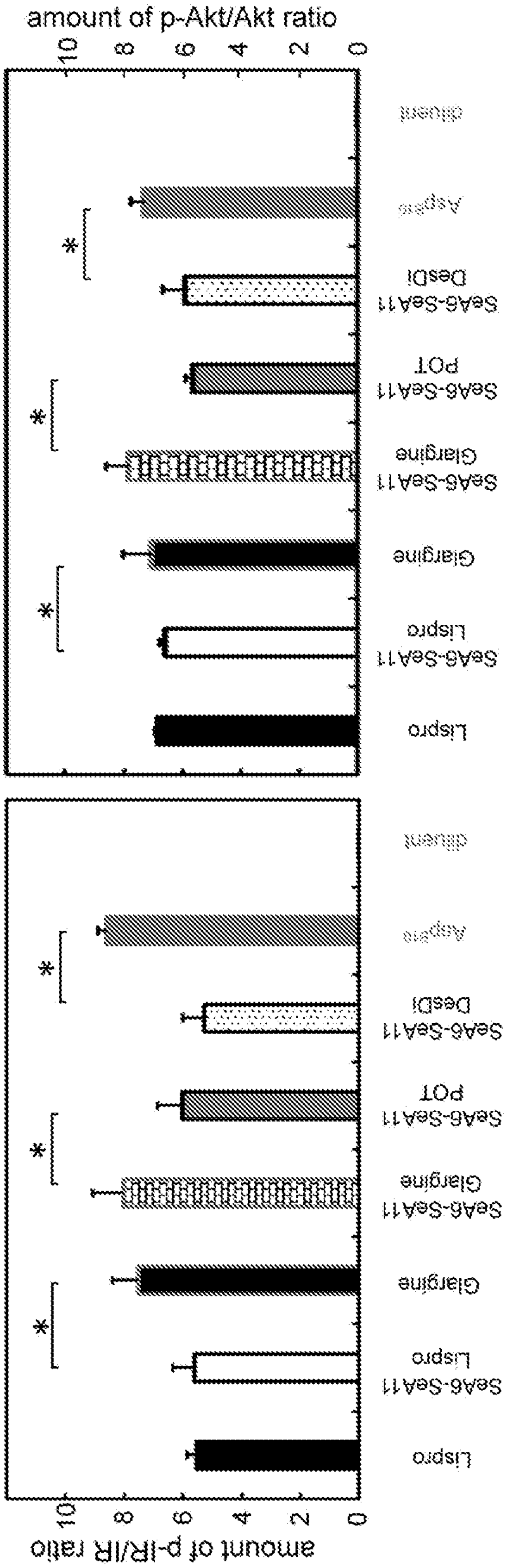

The studies of insulin signaling in MCF-7 breast-cancer cells were extended through Western blots to probe the extent of hormone-induced autophosphorylation of the insulin receptor (FIG. 9B, left) and hormone-induced downstream phosphorylation of the AKT kinase (FIG. 9B, right). In these assays the stimulatory activities of [C6U, C11U]-modified insulin lispro was indistinguishable from the stimulatory activities of native insulin lispro; the stimulatory activities of [C6U, C11U]-modified insulin glargine was indistinguishable from the stimulatory activities of native insulin glargine; the stimulatory activities of [C6U, C11U]-modified Des-Di (defined above) was indistinguishable from the stimulatory activities of native Des-Di; and the stimulatory activities of [C6U, C11U]-modified Orn$^{B29}$-insulin was indistinguishable from the stimulatory activities of native Orn$^{B29}$-insulin. In these assays insulin glargine and Asp$^{B10}$-insulin exhibited greater activity than insulin lispro (or WT-like controls Des-Di and Orn$^{B29}$-insulin) as is known in the art. The pairwise comparison of unmodified and [C6U, C11U]-modified analogues provides evidence that the diselenide bridge does not augment or attenuate hormone-triggered IR autophosphorylation or downstream AKT phosphorylation.

Figure 10A:
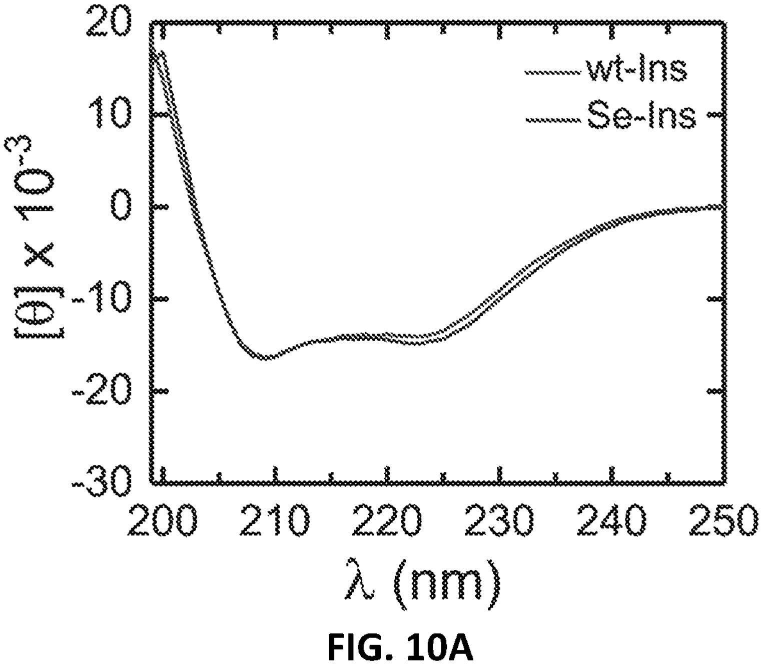
FIGS. 10A-10F are graphs presenting data for far-ultraviolet CD spectra and CD-detected chemical denaturation studies for wild type and various insulin analogs.
Figure 10B:
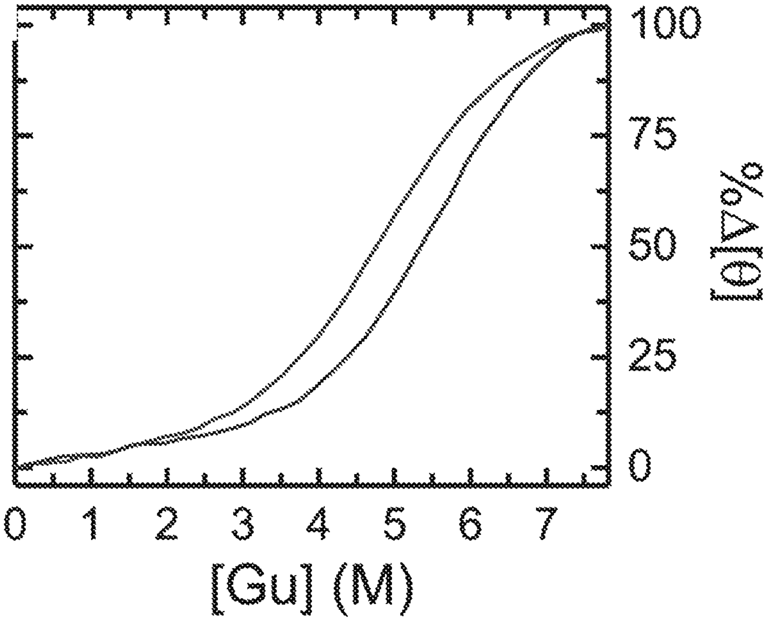
Figure 10C:
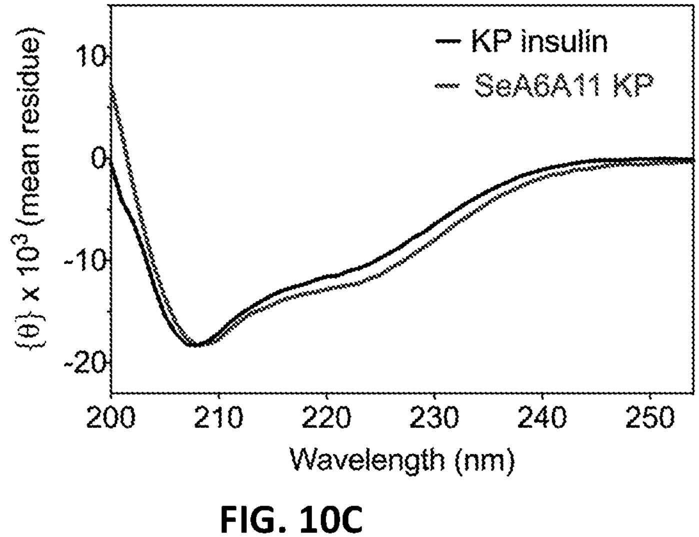
Figure 10D:
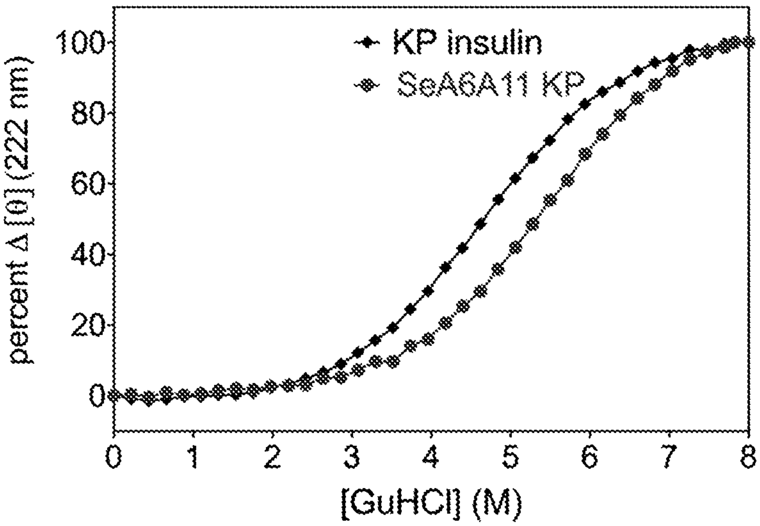
Figure 10E:
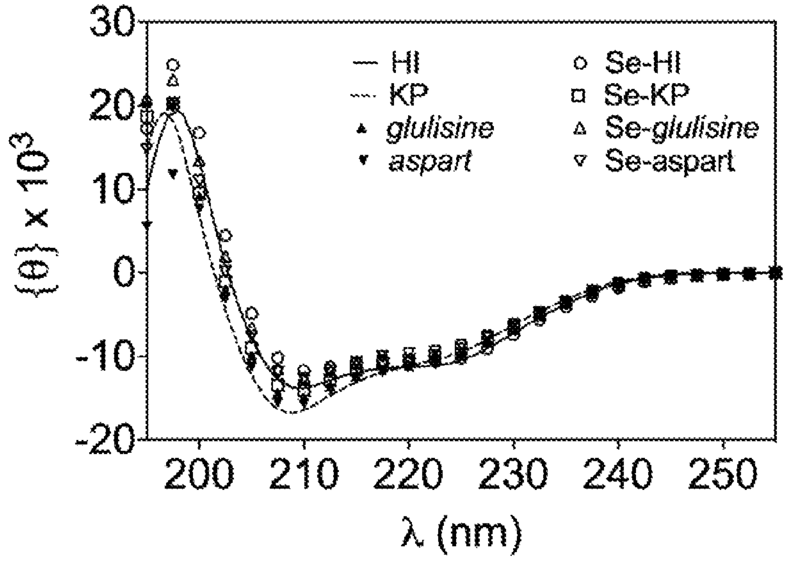

Secondary Structure. Far-ultraviolet circular dichroism (CD) spectra were obtained at 4° C. and 25° C. using an Aviv spectropolarimeter (Weiss et al. (2000) *Biochemistry* 39: 15429-15440). Samples contained ca. 25 μM WT insulin or analogues in 50 mM potassium phosphate (pH 7.4). Comparison of the spectra of WT human insulin and its [C6U$^{A}$, C11U$^{A}$] analogue demonstrated similar features indicative of substantial alpha-helix content (FIG. 10A); the paired Sec substitutions were associated with a slight accentuation of alpha-helix content. Corresponding CD studies of insulin lispro and its [C6U$^{A}$, C11U$^{A}$] analogue likewise demonstrated similar features but with more marked diselenide-associated accentuation (FIG. 10C). The latter difference represents a partial restoration of alpha-helix content that is perturbed in insulin lispro (relative to WT human insulin) due to its paired B-chain substitutions (Pro$^{B28}$→Lys and Lys$^{B29}$→Pro). The CD studies were repeated using a Jasco CD spectropolarimeter and extended to enable comparison of insulin glulisine versus its [C6U$^{A}$, C11U$^{A}$] analogue and comparison of insulin aspart versus its [C6U$^{A}$, C11U$^{A}$] analogue (FIG. 10E). Similar trends were in each case observed.

Thermodynamic Stability. Samples of insulin or insulin analogues were diluted to 1 μM for guanidine-induced denaturation studies at 25° C. To extract free energies of unfolding, denaturation transitions were fitted by non-linear least squares to a two-state model as described by Sosnick et al. (2000) *Methods Enzymol.* 317: 393-409. In brief, CD data θ(x), where x indicates the concentration of denaturant, were fitted by a nonlinear least-squares program according to $$\theta(x) = \frac{\theta_A + \theta_B e^{\left(-\Delta G^o_{H_2O} - mx\right)/RT}}{1 + e^{-\left(\Delta G^o_{H_2O} - mx\right)/RT}}$$

where x is the concentration of guanidine and where $\theta_A$ and $\theta_B$ are baseline values in the native and unfolded states. Baselines were approximated by pre- and post-transition lines $$\theta_A(x) = \theta_A^{H_2O} + m_A x \text{ and } \theta_B(x) = \theta_B^{H_2O} + m_B x.$$

Figure 10F:
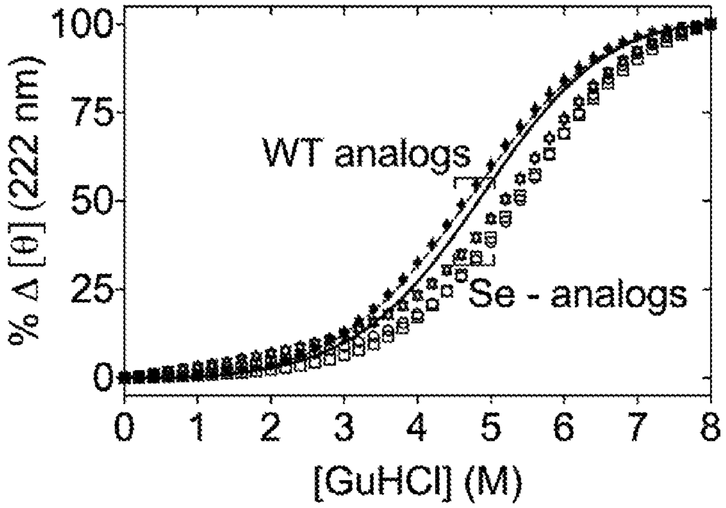

The m values obtained in fitting the variant unfolding transitions are lower than the m value obtained in fitting the wild-type unfolding curve. Such CD-monitored chemical denaturation studies (shown in FIGS. 10B and 10D) demonstrated that the A6-A11 diselenide bridge augmented the stability of the parent analogues in Examples 1 and 2 (i.e., WT human insulin and insulin lispro, respectively) by ca. 1 kcal/mole. This marked stabilization is similar in magnitude to that achieved by favorable amino-acid substitutions on the surface of the protein known in the art to stabilize the insulin molecule (Kaarsholm, N., et al. (1993) *Biochemistry* 32: 10773-8). The CD-detected guanidine-denaturation studies were repeated using a Jasco CD spectropolarimeter and extended to enable comparison of insulin glulisine versus its [C6U$^A$, C11U$^A$] analogue and comparison of insulin aspart versus its [C6U$^A$, C11U$^A$] analogue (FIG. 10F). Similar trends were in each case observed (Table 2). In addition, corresponding guanidine denaturation studies of the bottom four insulin analogues in Table 1, wherein the A6-A11 diselenide bridge was introduced in combination with a stabilizing standard amino-acid substitution, demonstrated that the thermodynamic effects were generally additive. This implies that the mechanism by which the diselenide bridge stabilizes the insulin monomer is complementary to and independent of that associated with standard substitutions on the surface of alpha-helices as known in the art: Asp$^{B10}$, His$^{A8}$ or Glu$^{A14}$. These findings therefore provide evidence that the stability of an insulin analogue may be optimized by combination of standard amino-acid substitutions with the presently disclosed diselenide bridge.

CD-detected guanidine-denaturation studies were likewise performed at pH 4.0 (as in the pharmaceutical formulation of Lantus® and Toujeo®) to evaluate the effect of the A6-A11 diselenide bridge on the thermodynamic stability of insulin glargine. Whereas the parent analogue is less stable than WT insulin (presumably due in large part to the destabilizing Gly$^{A21}$ substitution), WT-like stability is restored by the paired Cys→Sec substitutions (Table 3).

Figure 11A:
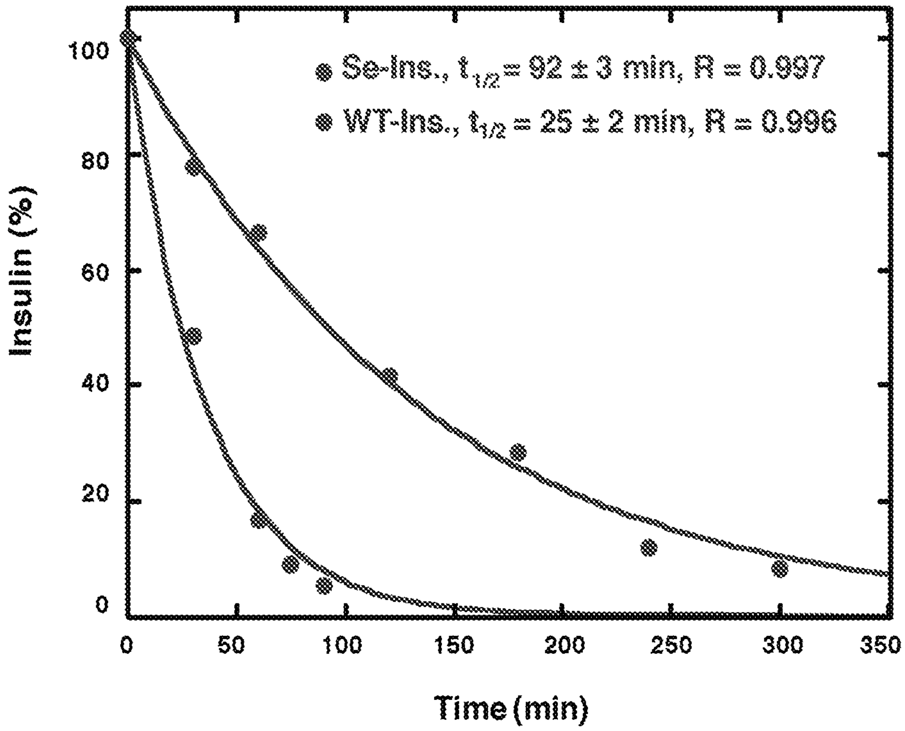
FIGS. 11A-11C provide three distinct assays of protein stability.

Resistance to Proteolysis by Glu-V8protease. To test whether the paired Sec substitutions might enhance the resistance of the insulin fold to peptide bond cleavage by Glu-V8 protease, stock solutions of WT human insulin and Se-insulin[C6U$^A$, C11U$^A$] (1.0 mg/mL) were prepared in 0.1 M $NH_4HCO_3$ buffer and the protease was dissolved in water to obtain a concentration of 1.0 mg/mL. The reaction was initiated by adding 5 μL of the protease solution to a volume of 250 μL of insulin solution. The reaction was incubated at 37° C. To monitor the degradation progress, 30 μL of the reaction aliquots were taken and quenched with 20 μL 0.1% TFA in water and were placed in ice to stop the reaction. The aliquots were analyzed by analytical HPLC XSelect C18 column (3.5 μm, 130 Å, 4.6×150 mm) and eluted using a gradient of 10% B in eluent A for 2 min then 10-60% B over 20 min. The results demonstrated marked stabilization of the protein by the A6-A11 diselenide bridge in this assay (FIG. 11A).

Figure 11B:
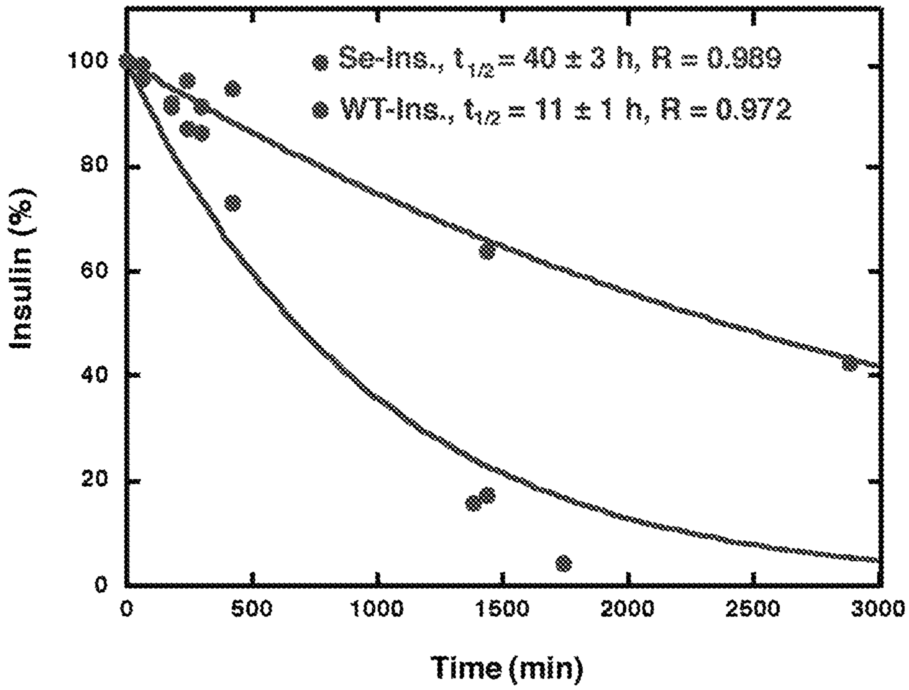

Resistance to reduction by glutathione (GSH). To test whether the paired Sec substitutions protected the disulfide bridges and diselenide bridge in the folded state from reduction by GSH, stock solutions of WT human insulin and Se-insulin[C6U$^A$, C11U$^A$](1 mg/mL) were prepared in phosphate buffer (20 mM, pH 7.4, 0.1 M NaCl), and a stock solution of reduced glutathione was prepared in the same buffer (1.62 mM). The reaction was initiated by adding 92.6 μL of the GSH in 125 μL of protein solution; buffer was added to a volume of 500 μL. Concentration of insulin was 0.25 mg/mL and 300 μM for GSH. Denaturation was carried out at 37° C. To monitor the reductive unfolding progress, 60 μL of the reaction aliquots were taken and quenched with 5 μL 0.1% TFA in water. The aliquots were analyzed by analytical HPLC XSelect C4 column (3.5 μm, 130 Å, 4.6×150 mm) and eluted using a gradient of 5% B in eluent A for 2 min then 5-70% B over 20 min. The results demonstrated marked stabilization of the protein by the A6-A11 diselenide bridge in this assay (FIG. 11B).

Figure 11C:
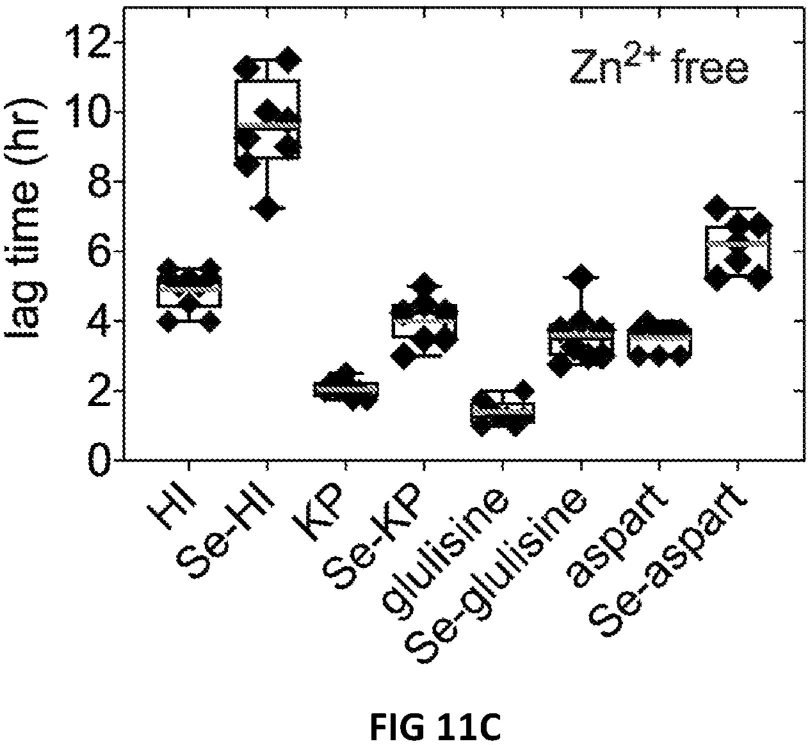

Resistance to onset of fibrillation. To test whether the paired Sec substitutions protected the prandial insulin analogues in current clinical use (insulin lispro, insulin glulisine and insulin aspart) from fibrillation, lag times were measured as described (Vinther, T. N., et al. (2013) Protein Sci. 22: 296-305). These studies employed an instrument that vibrates a 96-well-plate under a defined temperature; the read-out was provided by Thioflavin T (ThT) flourescence. The results demonstrated marked stabilization of the protein by the A6-A11 diselenide bridge in this assay at 37° C. (FIG. 11C). Indeed, whereas the paired B-chain substitutions in insulin lispro (Pro$^{B28}$→Lys and Lys$^{B29}$→Pro) foreshorten the lag time, i.e., hastening the onset of fibrillation as is known in the art, the A6-A11 diselenide bridge repairs this defect. The lag time of [C6U$^A$, C11U$^A$]-repaired insulin lispro is in fact longer than that of WT human insulin; similar results were obtained in studies of insulin aspart and insulin glulisine (Table 2).

In these fibrillation assays WT insulin or analogues were made 60 μM in phosphate-buffered saline (pH 7.4) with 0.02% sodium azide and 16 μM ThT. Samples were plated in a Costar® plate (250 μl/well) and incubated at 37° C. with continuous shaking at 960 revolutions per minute in a Synergy HIM Biotek plate reader. ThT fluorescence at 480 nm (following excitation at 450 nm) was assessed at 15-minute intervals. The time of initial ThT fluorescence just prior to enhancement of ThT emission intensity was defined as fibrillation lag time as in known in the art.

TABLE 2

Thermodynamic and fibrillation studies of [C6U$^A$, C11U$^A$]-modified insulin analogues

| Analog | $\Delta G_u$[a] (kcal mol−1) | $C_{mid}$[b] (M) | m[c] (kcal mol$^{-1}$ M$^{-1}$) | $\Delta\Delta G_u$ (kcal mol$^{-1}$) | fibrillation lag times[d] hours (N) |
|---|---|---|---|---|---|
| human insulin | 3.6 ± 0.1 | 4.9 ± 0.1 | 0.74 ± 0.01 | | 4.93 ± 0.57 (10) |
| Se-human insulin | 4.4 ± 0.1 | 5.7 ± 0.1 | 0.77 ± 0.01 | 0.8 ± 0.1 | 9.56 ± 1.40 (8) |
| insulin lispro | 2.8 ± 0.1 | 4.8 ± 0.1 | 0.58 ± 0.01 | | 1.88 ± 0.27 (8) |
| Se-insulin lispro | 3.8 ± 0.1 | 5.4 ± 0.1 | 0.69 ± 0.01 | 1.0 ± 0.1 | 4.00 ± 0.69 (7) |
| glulisine | 2.9 ± 0.1 | 4.8 ± 0.1 | 0.61 ± 0.01 | | 1.38 ± 0.35 (8) |
| Se-glulisine | 4.3 ± 0.1 | 5.5 ± 0.1 | 0.78 ± 0.01 | 1.4 ± 0.1 | 3.59 ± 0.80 (8) |
| insulin aspart | 2.8 ± 0.1 | 4.8 ± 0.1 | 0.58 ± 0.01 | | 3.53 ± 0.40 (9) |
| Se-insulin aspart | 3.9 ± 0.1 | 5.6 ± 0.1 | 0.71 ± 0.01 | 1.1 ± 0.1 | 6.18 ± 0.79 (7) |

[a]Parameters were inferred from CD-detected guanidine denaturation data (FIG. 10F) by application of a two-state model; uncertainties represent fitting errors for a given data set.
[b]The m-value (slope Δ(G)/Δ(M)) correlates with extent of hydrophobic surfaces exposed on denaturation.
[c]$C_{mid}$ is the guanidine denaturant concentration at which 50% of the protein is in the unfolded state.
[d]Fibrillation lag times pertain to zinc-free insulin and analogs (in a monomer-dimer equilibrium); each protein was made 60 μM in phosphate-buffered saline (pH 7.4). Samples were agitated via continuous shaking at 37 °C. The time of initial Thioflavin T (ThT) fluorescence defined the lag time.

TABLE 3

Thermodynamic stabilities of pI-shifted insulin analogs at pH 4.0

| Analog | $\Delta G_u$[a] (kcal mol$^{-1}$) | $C_{mid}$[b] (M) | m[c] (kcal mol$^{-1}$ M$^{-1}$) | $\Delta\Delta G_u$ (kcal mol$^{-1}$) |
|---|---|---|---|---|
| human insulin | 3.8 ± 0.1 | 5.0 ± 0.1 | 0.76 ± 0.01 | |
| Glargine | 2.8 ± 0.1 | 4.9 ± 0.1 | 0.57 ± 0.01 | −1.0 ± 0.1 |
| Se-glargine | 3.8 ± 0.1 | 6.0 ± 0.1 | 0.63 ± 0.01 | +1.0 ± 0.1 |

[a]Parameters were inferred from CD-detected guanidine denaturation data by application of a two-state model; uncertainties represent fitting errors for a given data set.
[b]The m-value (slope Δ(G)/Δ(M)) correlates with extent of hydrophobic surfaces exposed on denaturation.
[c]$C_{mid}$ is the guanidine denaturant concentration at which 50% of the protein is in the unfolded state.

TABLE 4

Statistics pertaining to the solution structure of [Sec$^{A6}$, Sec$^{A11}$]-insulin lispro

| parameter | SA ensemble[a] |
|---|---|
| **RMSD values from experimental distance and dihedral-angle restraints** | |
| all (866) | 0.038 ± 0.002 |
| intraresidue, i = j (285) | 0.044 ± 0.003 |
| sequential, \|i − j\| = 1 (240) | 0.034 ± 0.002 |
| medium range, 1 < \|i − j\| < 5 (169) | 0.036 ± 0.005 |
| long range, \|i − j\| ≥ 5 (172) | 0.032 ± 0.004 |
| dihedral angles (°, 77) | 0.96 ± 0.07 |
| **RMSD values from idealized covalent geometry** | |
| bonds (Å) | 0.0069 ± 0.0008 |
| angles (°) | 0.99 ± 0.01 |
| impropers (°) | 2.42 ± 0.12 |
| $E_{L\text{-}J}$ (kcal/mol)[b] | −209.6 ± 7.6 |
| **Coordinate precision of native insulin-like region**[c] | |
| rmsd of backbone atoms to the mean (Å) | 0.28 ± 0.06 |
| rmsd of all heavy atoms to the mean (Å) | 0.93 ± 0.16 |

[a]Mean ± standard error where applicable.
[b]Lennard-Jones potential energy function, calculated with CHARMM19 (27) empirical energy parameters.
[c]Based on residues A2-A20 and B5-B26.

2D-NMR studies of Se-insulin[C6U$^A$, C11U$^A$] demonstrate native-like structure. Samples of WT-insulin and Se-insulin[C6U$^A$, C11U$^A$] were prepared under identical conditions. Proteins were dissolved in 286 μL distilled $H_2O$, and the pH was corrected to ~3.6 using solutions of NaOH 0.1 M and HCl 0.15 M. Acetonitrile-$d_3$ (ACN-$d_3$) was added to get a final ratio 65%:35%, $H_2O$:ACN-$d_3$. The final concentration of the Se-insulin[C6U$^A$, C11U$^A$] was 0.93 mM and that of the WT-insulin 0.72 mM. NMR experiments were performed on a Bruker AVII 500 MHz spectrometer operating at the proton frequency of 500.13 MHz, using a 5-mm selective probe equipped with a self-shielded xyz-gradient coil at 27.2° C. The transmitter frequency was set on the water signal and calibrated at 4.811 ppm. Correlation spectroscopy (COSY) experiments were acquired using gradients for water saturation under identical conditions. Spectra were processed and analyzed with TopSpin (Bruker Analytische Messtechnik GmbH) and SPARKY3 software. The resulting spectra (not shown) were similar to those of WT human insulin under the same conditions. Changes in $^1$H-NMR chemical shifts were observed near the sites of Sec substitution as expected.

Figure 12A:
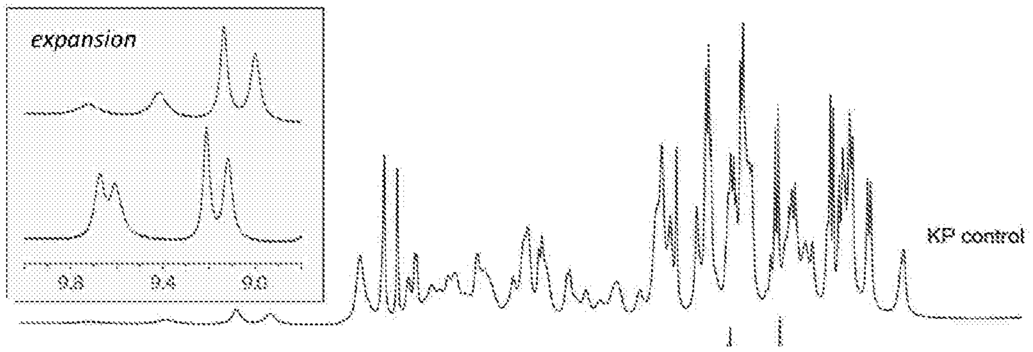

1D- and 2D-NMR studies of [C6U$^A$, C11U$^A$]-modified insulin lispro imply native-like structure with a subtle dynamic change. To test whether the A6-A11 diselenide bridge influences conformational fluctuations in an insulin monomer in the absence of an organic cosolvent (such as the 35% deuterated acetonitrile used above), $^1$H-NMR studies were undertaken of [C6U$^A$, C11U$^A$]-"repaired" insulin lispro relative to insulin lispro. Spectra were obtained in 10 mM deuterioacetic acid at pH 3.0 in 90% $H_2O$ and 10% $D_2O$ as described (Hua, X. Q., et al. (2011) *Frontiers in Endocrinology* doi: 10.3389/fendo.2011.00048). One-dimensional (1D) spectra in the amide-aromatic region are similar but not identical (FIGS. 12A and 12B); inset at upper left in the FIG. 12A are expansions of two amide downfield protons (9.4-9.8 ppm region) and two His HE resonances (9.0-9.4 ppm region). These amide resonances are sharper in the [C6U$^A$, C11U$^A$]-"repaired" insulin lispro (lower inset spectrum) relative to the corresponding resonances in the spectrum of insulin lispro (upper inset spectrum). The latter are broadened by millisecond motions on the intermediate NMR time scale. Such sharpening may be due to a change in time scale in either of two directions: faster or slower. Measurement of amide proton exchange (not shown) demonstrated slower exchange at this site, providing evidence of dynamic stabilization in accordance with the above four independent assays (chemical denaturation, resistance to proteolytic cleavage, resistance to reduction and resistance to fibrillation). Similar trends were observed on comparison of the $^1$H-NMR spectra under these conditions of insulin glargine versus [C6U$^A$, C11U$^A$]-modified insulin glargine (FIGS. 12C and 12D).

Figure 13A:
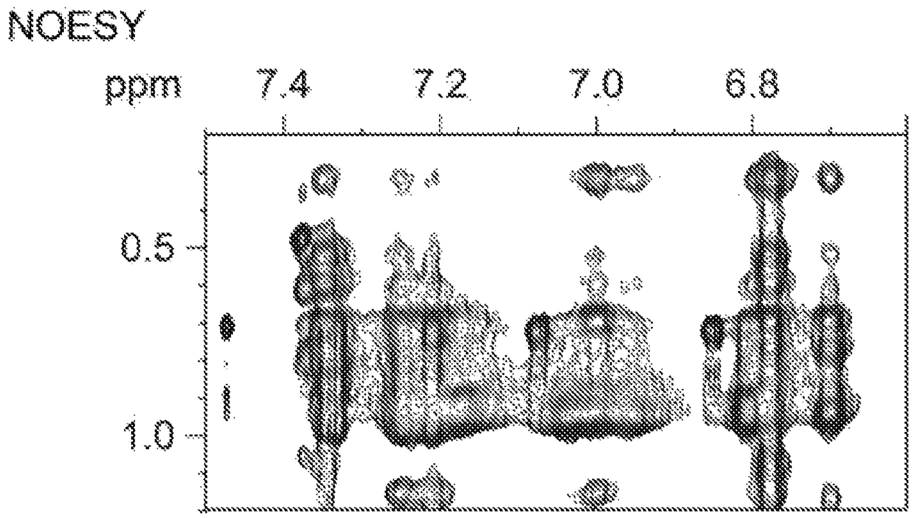
FIGS. 13A-13E provide two-dimensional (2D)$^{1}$H-NMR spectra of insulin lispro (FIGS. 13A and 13B) versus its [C6U$^{A}$, C11U$^{A}$] analogue (FIGS. 13C and 13D) in 10 mM deuterio-acetic acid at pH 3.0 and 25° C.
Figure 13B:
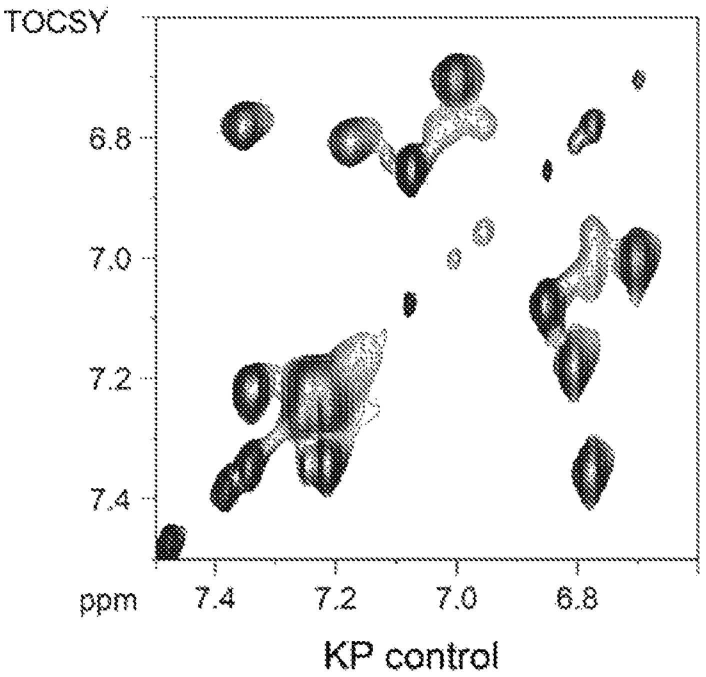
Figure 13C:
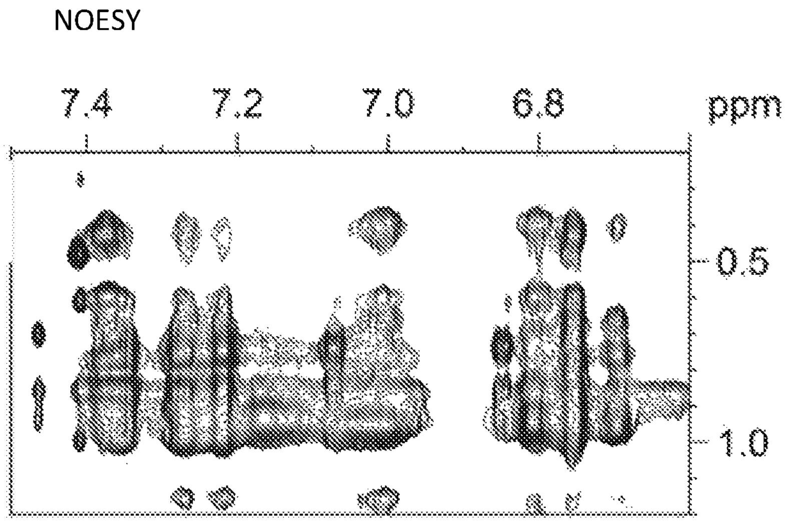
Figure 13D:
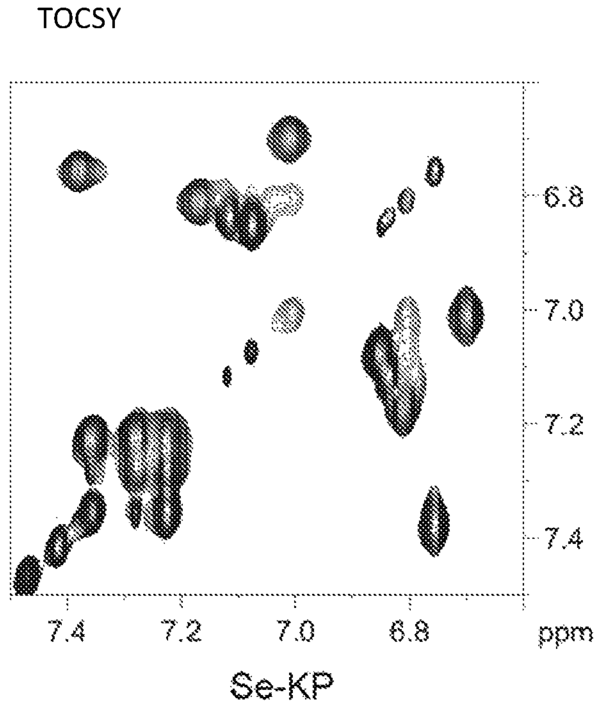
Figure 13E:
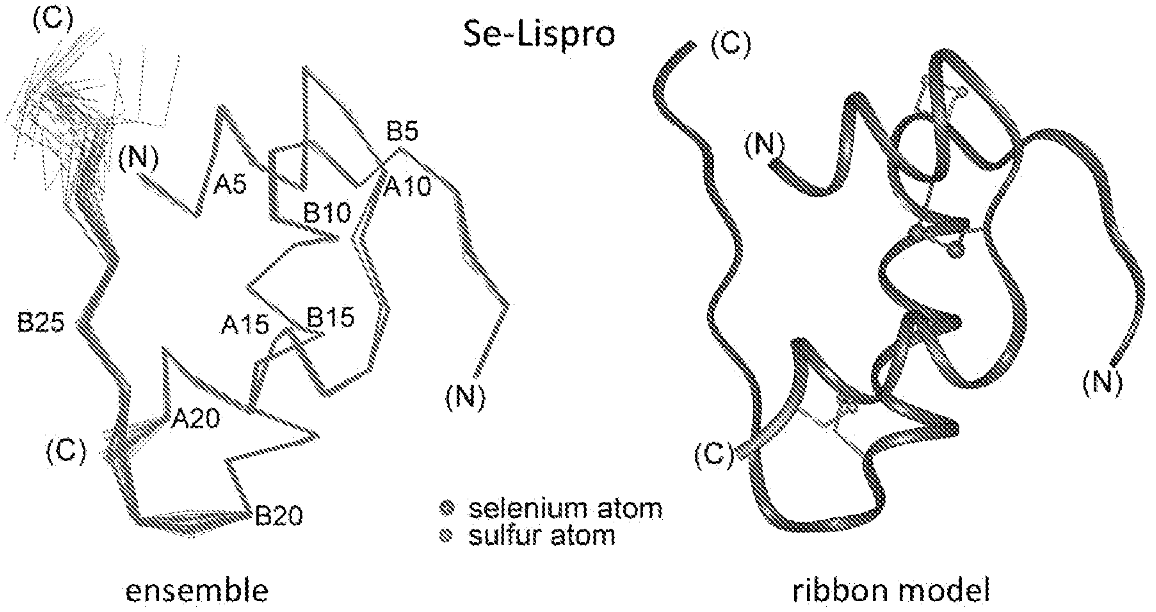

2D NMR studies of [C6U$^A$, C11U$^A$]-modified insulin lispro under these conditions provided evidence for similar overall structures as indicated by nonlocal nuclear Overhauser effects (FIGS. 13A and 13C) and patterns of aromatic spin systems (four tyrosines and three phenylalanines; FIGS. 13B and 13D). Complete resonance assignment and analysis of NOEs and a subset of J-coupling constants enabled calculation of an ensemble of solution structures (FIG. 13E). The solution structure of [C6U$^A$, C11U$^A$]-modified insulin lispro is similar to that of unmodified insulin lispro as previously reported (Hua, X. Q., et al. (2011) *Frontiers in Endocrinology doi:* 10.3389/fendo.2011.00048).

Figure 14A:
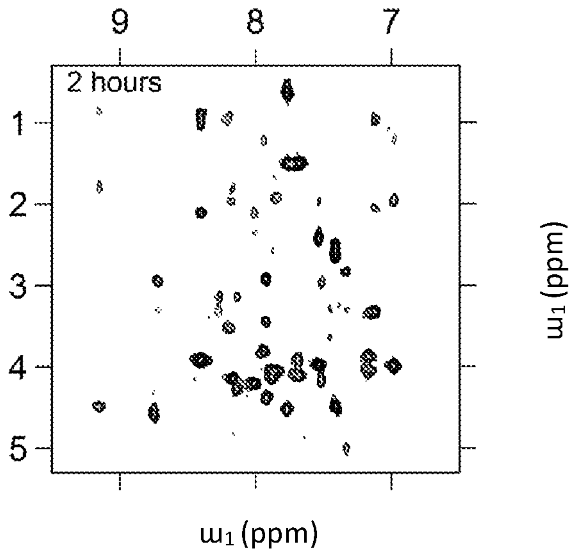
FIGS. 14A-14F provide $^{1}$H-$^{2}$H amide-proton exchange studies of insulin lispro versus its [C6U$^{A}$, C11U$^{A}$] analogue as a probe of thermodynamic stability.
Figure 14B:
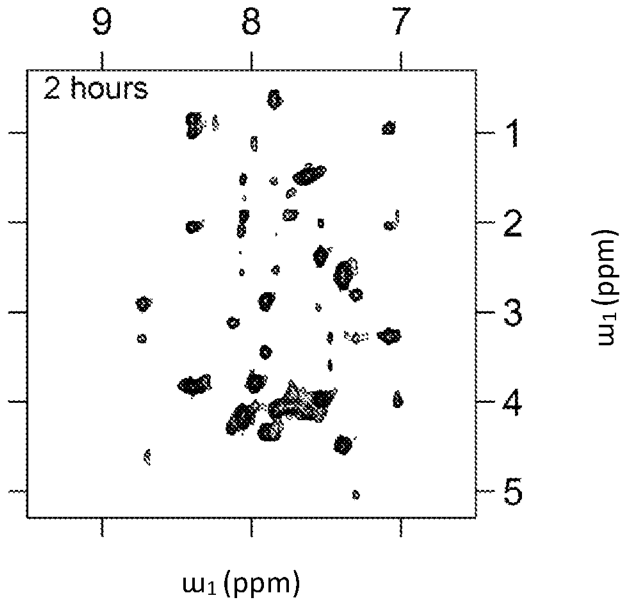
Figure 14C:
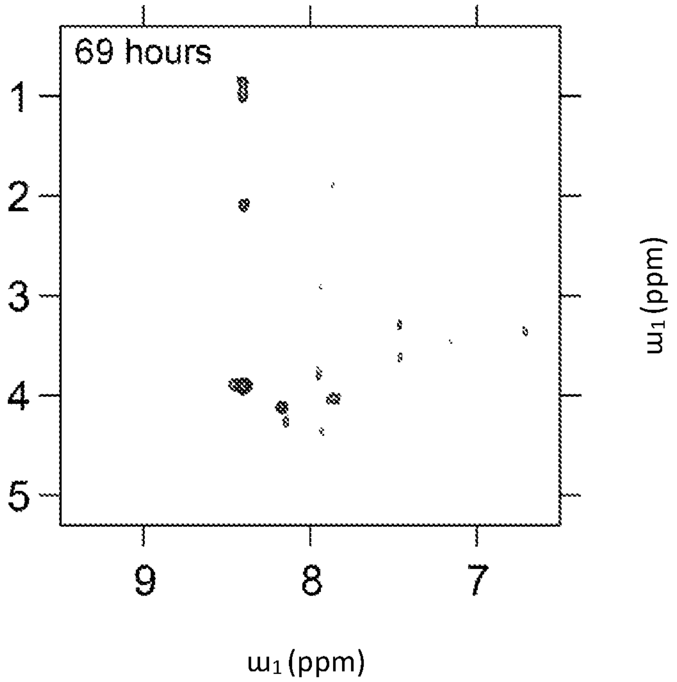
Figure 14D:
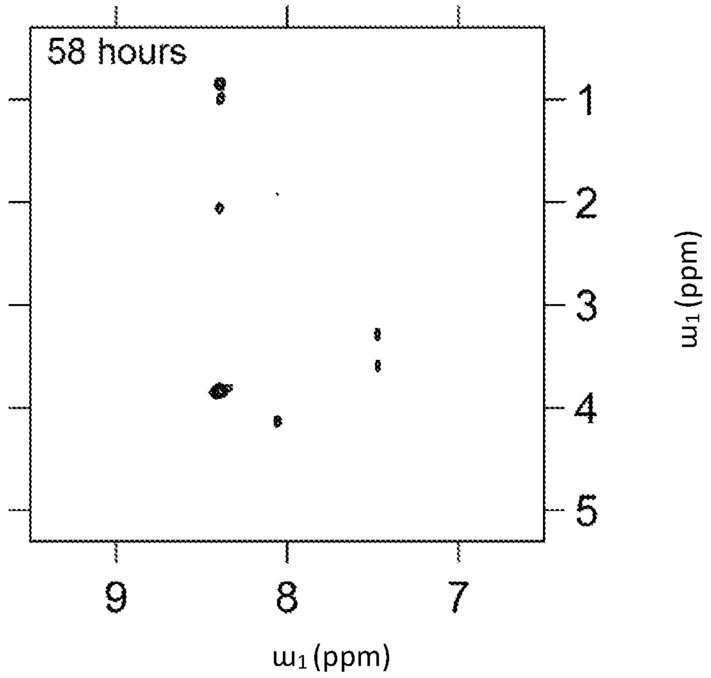
Figure 14E:
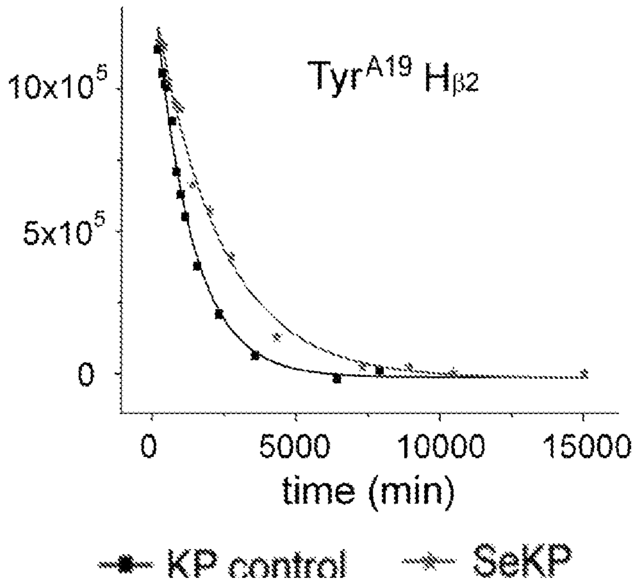
Figure 14F:
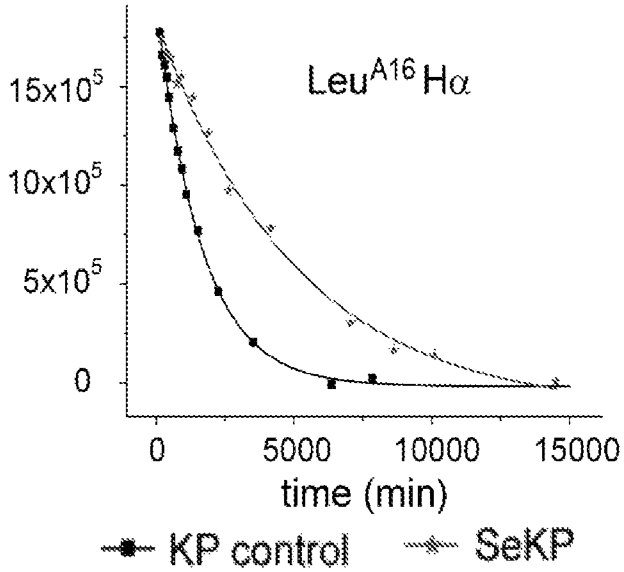

$^1$H-NMR-based Assessment of Thermodynamic Stability in $D_2O$. The kinetics of $^1$H-$^2$H amide proton exchange can be used to measure the thermodynamic stability of a protein and to evaluate changes in such stability on modification. This method exploits amide protons whose exchange in $D_2O$ solution requires global unfolding of the protein. Application to insulin lispro has previously been described (Hua, X. Q., et al. (2011) *Frontiers in Endocrinology* doi: 10.3389/fendo.2011.00048). This experimental protocol pertains to solutions of insulin or insulin analogues at pD 3.0 (in a buffer containing 10 mM deuterated acetic acid) to avoid base-catalyzed amide-proton exchange and so make feasible the measurement of local exchange, subglobal exchange and global exchange kinetics on an accessible time scale. Comparison of the kinetics of $^1$H-$^2$H amide proton exchange in insulin lispro versus [C6U$^A$, C11U$^A$]-modified insulin lispro under these conditions corroborated the overall results of the above CD-detected guanidine denaturation assays at neutral pH. 2D TOCSY spectra of residual cross peaks between main-chain amide resonances and carbon-bound resonances are shown at designated time points in [C6U$^A$, C11U$^A$]-modified (FIGS. 14A and 14C) versus unmodified insulin lispro (FIGS. 14B and 14D). Comparison of two sites of global exchange in the respective A chains (residues Tyr$^{A19}$ and Leu$^{A16}$) demonstrated in each case delayed exchange due to the A6-A11 diselenide bridge (FIG. 14E). Quantitative analysis of the degree of protection (the "protection factor") at each site indicated an increase in stability ($\Delta\Delta G_u$) of 0.4-0.5 kcal/mole under these conditions (pH 3.0 and 25° C. in a $D_2O$ solution). Although this gain in stability is less marked than that inferred above by CD-based guanidine denaturation experiments at neutral pH and in an $H_2O$ solution, the general trends are the same.

Figure 15A:
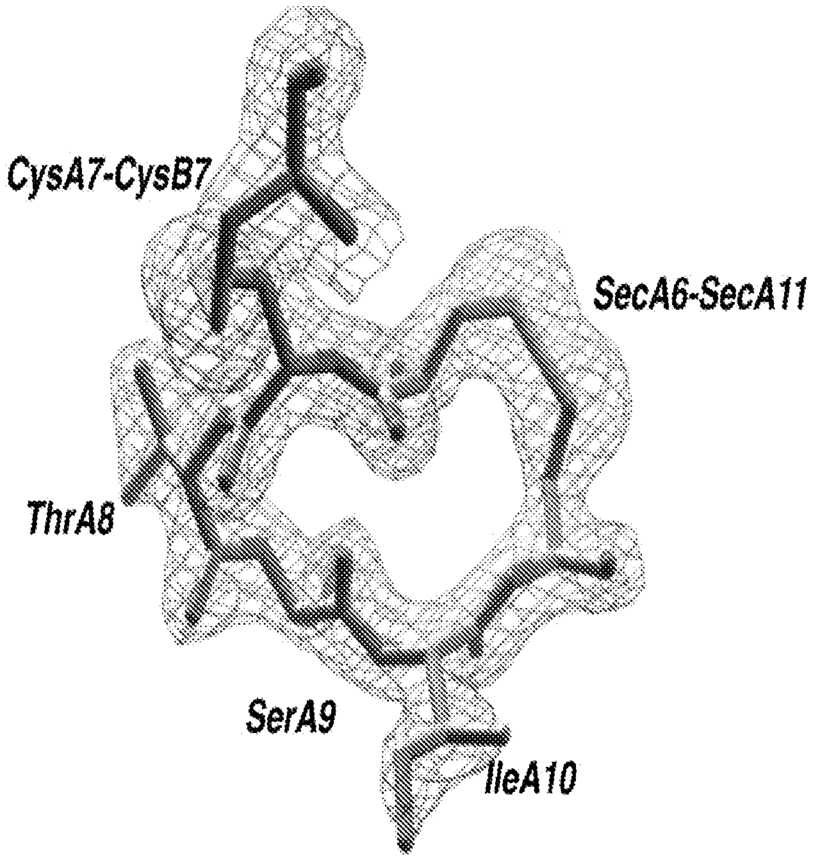
FIGS. 15A & 15B depict structural representations of Se-insulin monomer.
Figure 15B:
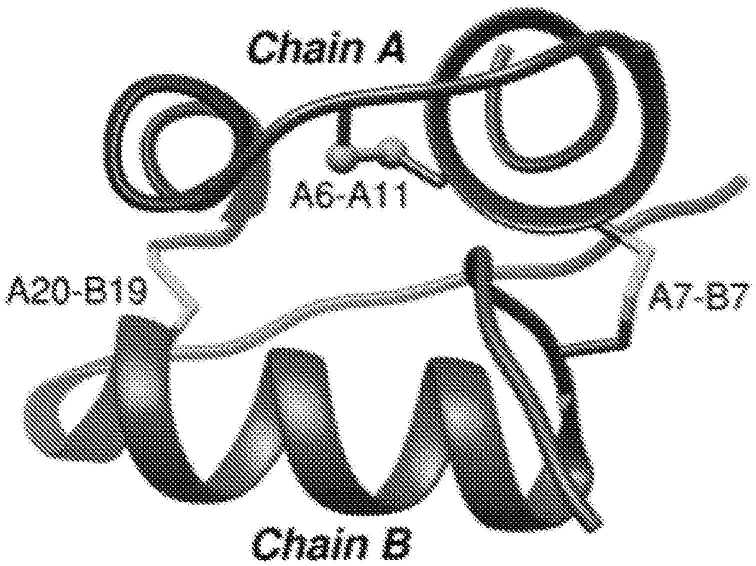

X-ray crystallography. To obtain single crystals suitable for X-ray diffraction, lyophilized human insulin containing the A6-A11 diselenide bridge was dissolved in 20 mM HCl to obtain an ~8 mg/mL protein solution, which was used subsequently for crystallization trials. Crystals, obtained through the hanging-drop vapor diffusion method, appeared after ~3 weeks in drops containing 2 μl protein and 1 μl reservoir, equilibrated over a 500 μl reservoir solution containing 1.5 M NaCl, 35 mM NaCitrate, 0.5 mM ZnAcetate, and 0.3 M Tris pH 7.5. The crystals were then soaked for ~10 sec in a cryogenic solution containing 20% glycerol and 80% reservoir solution prior to their flash-freezing in liquid nitrogen for X-ray diffraction data collection. X-ray diffraction data were collected at the Se peak (λ=0.976 Å, T=100 K) using a Pilatus 6M detector in the ID29 beamline of the ESRF synchrotron (Grenoble, France). The raw diffraction images were processed, integrated, and scaled with the XDS software, indicating a complete data set to 1.82 Å resolution belonging to the P1 space group. These data allowed the structure determination by the single anomalous dispersion (SAD) methodology, using the anomalous data that was obtained from the two Sec residues incorporated into the protein. The AutoSol software identified 20 Se atoms with a figure of merit of 0.379, producing phases of sufficient quality to automatically build 213 residues in the asymmetric unit, corresponding to respective $R_{work}$ and $R_{free}$ values of 36.00% and 37.84%. This initial structure was later on improved by iterative cycles of manual building with the program Coot, and concomitant refinement with the program phenix.refine. The final structure was shown to contain only 16 Se atoms, corresponding to 8 independent insulin analogue monomers in the asymmetric unit and 402 modeled protein residues, producing final $R_{work}$ and $R_{free}$ values of 18.96% and 22.92%, respectively. Geometric validation of the structure was conducted with Procheck and Molprobity, confirming a model of good structural and stereochemistry parameters, as demonstrated by root-mean-square deviation (RMSD) values of 0.013 Å and 1.491° for the bond lengths and bond angles, respectively. The final Se-Insulin structure was deposited in the RCSB protein data bank under accession code 6H3M. Representative electron density is shown in FIG. 15A; a representative molecule is shown as a ribbon diagram in FIG. 15B. The A6-A11 disulfide bridge is formed in the core at a position and within a structural environment similar to that of the native disulfide bridge in WT insulin. The secondary structure of this molecule is identical to that of WT position; the A20-B19 and A7-B7 disulfide bridges are essentially identical to the corresponding bridges in WT insulin.

Figure 16A:
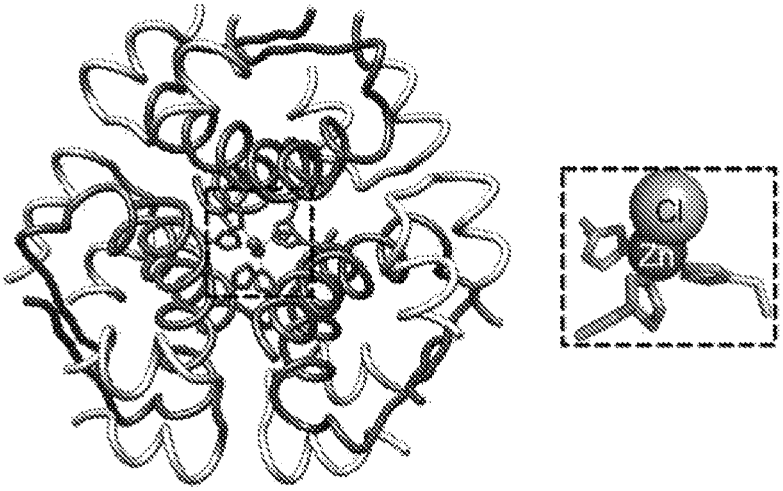
FIGS. 16A-16D provides the visible absorption spectra of $Co^{2+}$-substituted insulin analogue hexamers and illustrates kinetic studies of their dissociation.
Figure 16B:
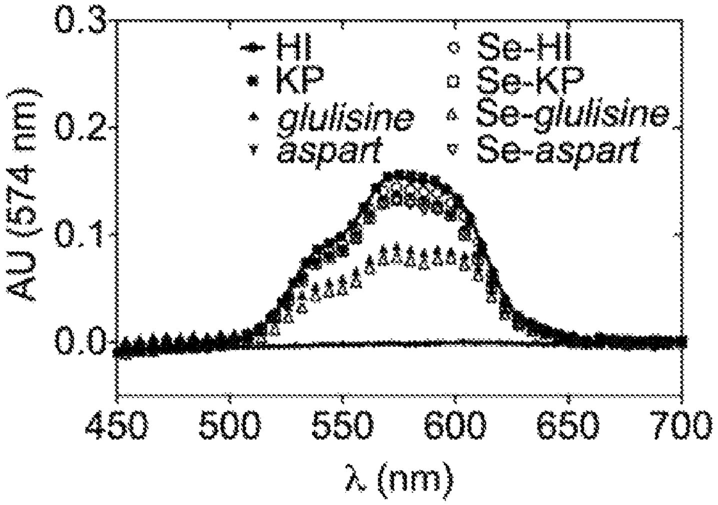
Figure 16C:
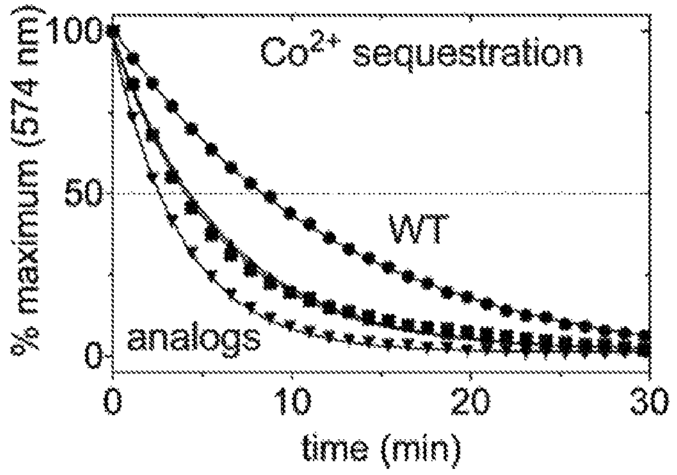
Figure 16D:
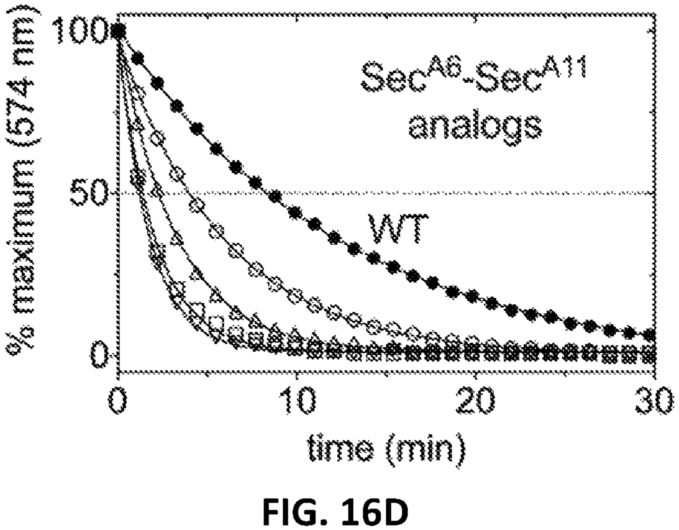

Kinetics of insulin hexamer disassembly. The prandial insulin analogues in current clinical use exhibit more rapid absorption from a SQ depot. This property, critical to their therapeutic benefit, is due to more rapid dissociation of insulin hexamers relative to WT human insulin. It is therefore critical to evaluate whether the augmented stability of [C6U$^A$, C11U$^A$]-modified prandial analogs might delay their dissociation from a hexameric assembly and thereby compromise their clinical efficacy as rapid-actinining formulations. A model was provided by $R_6$ metal-ion-stabilized insulin hexamers wherein $Co^{2+}$ ions were substituted for the two axial zinc ions (FIG. 16A). This assay exploits the visible absorption spectrum of the tetrahedrally coordinated metal ion, which in the case of $Co^{2+}$ contains an incomplete d-electronic shell and so exhibits d-d optical transitions (FIG. 16A) as described (Rege, N., et al. (2018) *J. Biol. Chem.* 293: 10895-10910). The kinetic assay is triggered by addition of a high concentration of ethylene-diamine-tetra-acetic acid (EDTA) to sequester the metal ions on release from a dissociated insulin hexamer. Because the competing $Co^{2+}$/EDTA complex is octahedral (and not tetrahedral) the d-d transitions are negligible; and because the affinity of $Co^{2+}$ for EDTA is much stronger than its affinity for insulin, addition of excess EDTA leads to sequestration of $Co^{2+}$ that is essentially irreversible. Baseline kinetic studies of the unmodified insulin analogs are shown in FIG. 16C, and companion studies of the [C6U$^A$, C11U$^A$]-modified prandial analogs in FIG. 16D. Remarkably, the diselenide bridge is associated with accelerated hexamer diassaembly despite its general stabilizing effect on the insulin analogue monomer. Mono-exponential curve fitting of these kinetic transitions indicates that the A6-A11 diselenide bridge leads, in each pair of cognate analogues (e.g., insulin lispro versus [C6U$^A$, C11U$^A$]-modified insulin lispro), to a ca. twofold reduction in estimated half-life at 25° C.

Figure 5:
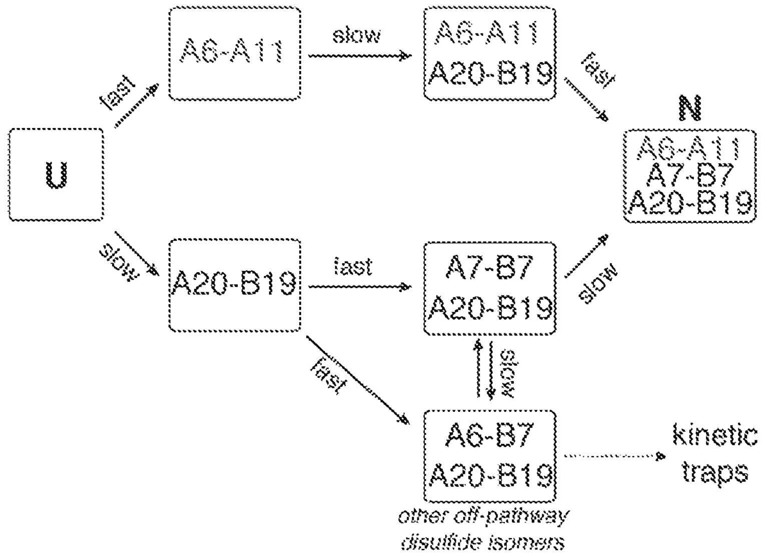
FIG. 5 provides a scheme for the mechanism of disulfide pairing in insulin-chain combination. The role of cystine A6-A11 is indicated in the upper pathway. Native pairing can be reached by the upper or lower pathways of the insulin molecule (top) and modifications pertaining to the present disclosure. At bottom are off-pathway steps that may in principle lead to formation of non-native disulfide isomers. Individual steps are labeled "fast" or "slow" in relation to the kinetic properties of these reactions.
Figure 6:
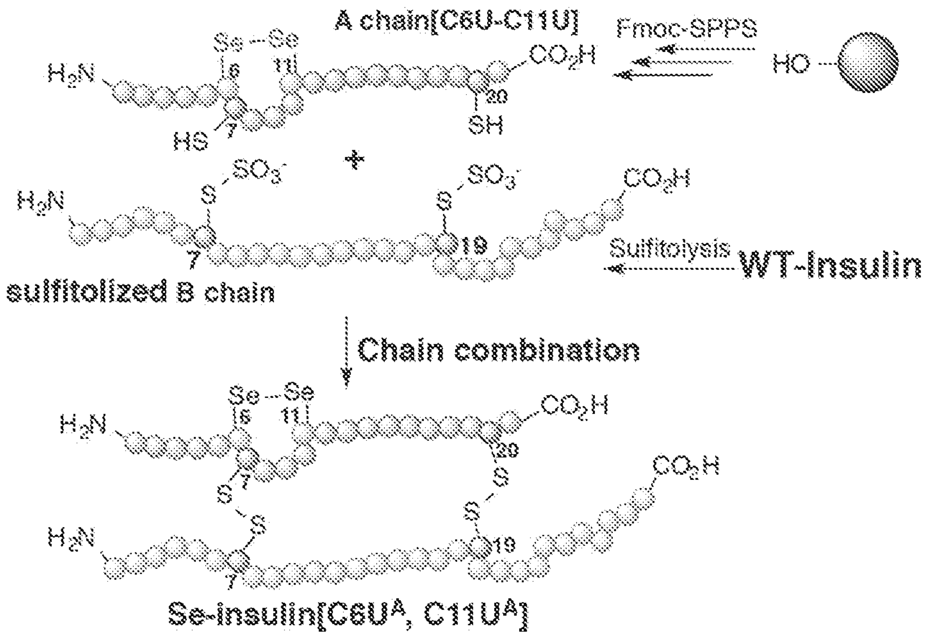
FIG. 6 illustrates the expedited mechanism of insulin chain combination envisaged to occur on pair-wise substitution of $Cys^{A6}$ and $Cys^{A11}$ by Sec, leading to rapid initial formation of an A6-A11 diselenide bridge (at top). In the example shown, chemical semi-synthesis of Se-insulin (WT human insulin with $Sec^{A6}$ and $Sec^{A11}$; designated Se-insulin [$C6U^A$, $C11U^A$] employed a synthetic A chain and biosynthetic B chain (obtained from commercial insulin by oxidative sulfitolysis).

The present modification of insulin and known insulin analogues provides a method to enhance the speed and fidelity of insulin chain combination, a reaction known in the art leading to specific disulfide pairing between the A- and B chains of insulin (FIG. 5). Because this method employs modification of only one of the two chains employed in this reaction (FIG. 6), this scheme represents a significant improvement relative to alternative strategies that would require substitution of selenocysteine in each of the two chains (Arai, K., et al. 2017). Further, the utility of exploiting an internal bridge (as distinct from an external bridge) is surprising given that the Selenium atom is larger than the Sulfur atom and given that the Se—Se bond is longer than the S—S bond—thereby in principle introducing a steric perturbation into the hydrophobic core of a globular protein. The present disclosure is also unrelated to the prior art by which the efficiency of insulin chain combination has been enhanced through use of a single-chain precursor (Zaykov, A. N., et al., 2014) or A4-B30 side-chain ester linkage (Sohma, Y., and Kent, S. B., 2009). Whereas the paired B-chain substitutions in insulin lispro are known in the art to impair the efficiency of insulin chain combination, we have demonstrated that this perturbation can be mitigated and indeed overcome via introduction of selenocysteines at positions A6 and A11.

Although the Embodiments presented herein as examples were obtained by chemical synthesis, it is envisioned that the insulin analogues of the present disclosure may also be derived from Lys-directed proteolysis of a precursor polypeptide in yeast biosynthesis in *Pichia pastoris, Saccharomyces cerevisciae*, or other yeast expression species or strains. Such strains may be engineered to insert Sec at positions A6 and A11 by means of an engineered tRNA synthetase and orthogonal nonsense suppression.

The invention claimed is:

1. An insulin analogue comprising an insulin A chain and an insulin B chain wherein said A chain comprises a sequence of GIVEQ$X_6$C$X_8$ $X_9$I$X_{11}$SLYQLENYC$X_{21}$-$R_{53}$ (SEQ ID NO: 17); and said B chain comprises the sequence $R_{62}$-$X_{25}$LCG$X_{29}X_{30}$LV$X_{33}X_{34}$LYLVCG$X_{41}X_{42}$GF$X_{45}$ (SEQ ID NO: 11), or FV$X_{23}$Q$X_{25}$LCG$X_{29}X_{30}$ LV$X_{33}X_{34}$LYLVCG$X_{41}X_{42}$GF$X_{45}$ (SEQ ID NO: 18), wherein $X_6$ is selenocysteine;

$X_8$ is histidine, threonine, lysine, arginine, or tryptophan;

$X_9$ is serine, lysine, or alanine;

$X_{11}$ is selenocysteine;

$X_{21}$ is selected from the group consisting of alanine, glycine, serine, threonine, glutamine, asparagine, and aspartic acid $X_{23}$ is Lys;

$X_{25}$ is histidine, arginine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{41}$ is selected from the group consisting of glutamic acid, aspartic acid and asparagine;

$X_{42}$ is selected from the group consisting of alanine, ornithine, lysine and arginine;

$X_{45}$ is tyrosine or phenylalanine;

$R_{53}$ is COOH or $CONH_2$; and $R_{62}$ is selected from the group consisting of PGPE (SEQ ID NO: 14), a tripeptide valine-asparagine-glutamine, a dipeptide asparagine-glutamine, glutamine, and an N-terminal amine, wherein, an internal diselenide bridge between positions A6 and A11 is larger than a disulfide bridge formed between the positions A6 and A11, and wherein the internal diselenide bridge between the positions A6 and A11 enhances efficiency of core packing within the interior of the insulin analogue.

2. The insulin analogue of claim 1, wherein said A chain comprises the sequence of GIVEQ$X_6$C$X_8$SI$X_{11}$SLYQLENYC$X_{21}$-$R_{53}$ (SEQ ID NO: 15), and said B chain comprises the sequence FV$X_{23}$Q$X_{25}$LCGSHLVEALYLVCGERGFFYT$X_{48}X_{49}X_{50}$ (SEQ ID NO: 16), wherein $X_6$ is selenocysteine;

$X_8$ is histidine, arginine or threonine;

$X_{11}$ is selenocysteine;

$X_{21}$ is alanine, glycine or asparagine;

$X_{23}$ is Lys;

$X_{25}$ is histidine or threonine;

$X_{48}$ is proline, lysine or aspartic acid;

$X_{49}$ is proline, lysine or glycine;

$X_{80}$ is threonine, alanine or serine; and $R_{53}$ is COOH or $CONH_2$.

3. The insulin analogue of claim 1, wherein the B chain sequence comprises the sequence FVKQ$X_{25}$LCGSHLVEALYLVCGERGFF-$R_{63}$ (SEQ ID NO: 21), wherein $X_{25}$ is selected from the group consisting of histidine and threonine; and $R_{63}$ is selected from the group consisting of YT$X_{28}$KT (SEQ ID NO: 22), YTKPT (SEQ ID NO: 23), YT$X_{28}$K (SEQ ID NO: 24), YTKP (SEQ ID NO: 25), YTPK (SEQ ID NO: 26), YT$X_{28}$, YT, Y and a bond, wherein $X_{28}$ is proline, lysine, aspartic acid or glutamic acid.

4. The insulin analogue of claim 3, wherein the B chain sequence comprises the sequence FVKQ$X_{25}$LCGSHLVEALYLVCGERGFFYTEKT (SEQ ID NO: 28), wherein $X_{25}$ is selected from the group consisting of histidine and threonine.

5. The insulin analogue of claim 4, wherein $X_{25}$ is histidine.

6. The insulin analogue of claim 1, wherein the A chain comprises a sequence GIVEQ$X_6$CTSI$X_{11}$SLYQLENYCN (SEQ ID NO: 30) and said B chain comprises a sequence FVKQHLCGSHLVEALYLVCGERGFFYTPET (SEQ ID NO: 7), wherein $X_6$ is selenocysteine;

$X_{11}$ is selenocysteine;

$X_{59}$ is an acyl derivative of lysine or glutamic-acid-bridged acyl derivative of lysine, and $X_{60}$ is Thr, Ala, Ser or absent.

7. The insulin analogue of claim 4 wherein, said A chain comprises the sequence GIVEQ$X_6$CTSI$X_{11}$SLYQLENYCN-$R_{53}$ (SEQ ID NO: 30) and said B chain comprises the sequence FVKQ$X_{25}$LCGSHLVEALYLVCGERGFFYTEKT (SEQ ID NO: 28), wherein $X_{25}$ is histidine; and $R_{53}$ is COOH or $CONH_2$.

8. The insulin analogue of claim 6, wherein a hydrophilic moiety is covalently linked at one or more positions corresponding to A14, A15, B0, B1, B10, or B22, and wherein, if the B chain comprises FVKQHLCGSHLVEALYLVCGERGFFYTPET (SEQ ID NO: 7), the hydrophilic moiety is covalently linked at one or more positions corresponding to A14, A15, B0, B1, B10, B22, B28, or B29 wherein $X_6$ is selenocysteine;

$X_{11}$ is selenocysteine;

$X_{59}$ is an acyl derivative of lysine or glutamic-acid-bridged acyl derivative of lysine, and $X_{60}$ is Thr, Ala, Ser or absent.

9. The insulin analogue of claim 8, wherein the hydrophilic moiety is a polyethylene glycol.

10. The insulin analogue of claim 6, further comprising an acyl group or alkyl group covalently linked to an amino-acid side chain of said insulin analogue.

11. The insulin analogue of claim 10, wherein said acyl group or alkyl group is covalently linked to one or more positions selected from A14, A15, B0, B1, B10, B22, B28, B29 of the insulin analogue.

12. A non-covalent dimer or multimer comprising two or more insulin analogues claim 1.

13. A pharmaceutical composition comprising an insulin analogue of claim 1, or pharmaceutically acceptable salt thereof, and a pharmaceutically acceptable carrier.

14. A pharmaceutical composition, wherein augmented intrinsic stabilities of the insulin analogue of claim 7 makes unnecessary the inclusion of zinc ions in a formulation and so enable inclusion of excipients associated with rapid absorption of insulin analogues from a subcutaneous depot, but that would otherwise sequester zinc ions, comprising triphosphate ions, trisulphate ions, chelating agents, ethylene-diamine-tetra-acetic acid (EDTA) or ethylene glycol-bis (β-aminoethyl ether)-N,N,N',N'-tetraacetic acid (EGTA).

15. A method of treating diabetes in a subject, said method comprising administering an effective amount of a pharmaceutical composition of claim 13 to the subject.

16. An insulin analogue comprising an insulin A chain and an insulin B chain wherein said A chain is a sequence of GIVEQ$X_6$C$X_8$ $X_9$I$X_{11}$SLYQLENYC$X_{21}$-$R_{53}$ (SEQ ID NO: 17); and said B chain is a sequence $R_{62}$-$X_{25}$LCG$X_{29}X_{30}$LV$X_{33}$ $X_{34}$LYLVCG$X_{41}X_{42}$GF$X_{45}$ (SEQ ID NO: 11), or FV$X_{23}$Q$X_{25}$LCG$X_{29}X_{30}$LV$X_{33}X_{34}$LYLVCG$X_{41}X_{42}$ GF$X_{45}$ (SEQ ID NO: 18), wherein $X_6$ is selenocysteine;

$X_8$ is histidine, threonine, lysine, arginine, or tryptophan;

$X_9$ is serine, lysine, or alanine;

$X_{11}$ is selenocysteine;

$X_{21}$ is selected from the group consisting of alanine, glycine, serine, threonine, glutamine, asparagine, and aspartic acid $X_{23}$ is Asn or Lys;

$X_{25}$ is histidine, arginine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{41}$ is selected from the group consisting of glutamic acid, aspartic acid and asparagine;

$X_{42}$ is selected from the group consisting of alanine, ornithine, lysine and arginine;

$X_{45}$ is tyrosine or phenylalanine;

$R_{53}$ is COOH or $CONH_2$; and $R_{62}$ is selected from the group consisting of FVNQ (SEQ ID NO: 13), PGPE (SEQ ID NO: 14), a tripeptide valine-asparagine-glutamine, a dipeptide asparagine-glutamine, glutamine, and an N-terminal amine, wherein, an internal diselenide bridge between positions A6 and A11 is larger than a disulfide bridge formed between the positions A6 and A11, and wherein the internal diselenide bridge between the positions A6 and A11 enhances efficiency of core packing within the interior of the insulin analogue.

17. A pharmaceutical composition comprising an insulin analogue of claim 16, or pharmaceutically acceptable salt thereof, and a pharmaceutically acceptable carrier.

* * * * *